(12) United States Patent
Vu et al.

(10) Patent No.: US 7,285,550 B2
(45) Date of Patent: Oct. 23, 2007

(54) TRIAZOLOTRIAZINES AND PYRAZOLOTRIAZINES AND METHODS OF MAKING AND USING THE SAME

(75) Inventors: Chi Vu, Arlington, MA (US); Russell C. Petter, Stow, MA (US); Gnanasambandam Kumaravel, Westford, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 10/552,303

(22) PCT Filed: Apr. 9, 2004

(86) PCT No.: PCT/US2004/011005

§ 371 (c)(1),
(2), (4) Date: Jul. 26, 2006

(87) PCT Pub. No.: WO2004/092170

PCT Pub. Date: Oct. 28, 2004

(65) Prior Publication Data

US 2006/0276475 A1   Dec. 7, 2006

Related U.S. Application Data

(60) Provisional application No. 60/461,356, filed on Apr. 9, 2003.

(51) Int. Cl.
| | |
|---|---|
| C07D 487/04 | (2006.01) |
| C07D 403/04 | (2006.01) |
| C07D 403/06 | (2006.01) |
| C07D 403/14 | (2006.01) |
| A61K 31/53 | (2006.01) |
| A61P 25/16 | (2006.01) |

(52) U.S. Cl. ............... 514/245; 544/206; 544/207; 544/211; 544/212

(58) Field of Classification Search ........... 544/206, 544/207, 211, 212; 514/245
See application file for complete search history.

(56) References Cited

U.S. PATENT DOCUMENTS

| | | | |
|---|---|---|---|
| 4,739,053 A | 4/1988 | Albert et al. | |
| 5,204,353 A | 4/1993 | Meier | |
| 5,356,894 A | 10/1994 | Rodney et al. | |
| 5,458,135 A | 10/1995 | Patten et al. | |
| 5,747,496 A | 5/1998 | Cox et al. | |
| 6,005,109 A | 12/1999 | Faraci et al. | |
| 6,107,301 A | 8/2000 | Aldrich et al. | |
| 6,197,788 B1 | 3/2001 | Fletcher et al. | |
| 6,583,156 B1 | 6/2003 | Gillespie et al. | |
| 6,608,085 B1 | 8/2003 | Gillespie et al. | |
| 6,787,541 B1 | 9/2004 | Gillespie et al. | |

FOREIGN PATENT DOCUMENTS

| | | |
|---|---|---|
| EP | 0390112 | 10/1990 |
| EP | 0459702 A2 * | 5/1991 |
| EP | 0459702 | 12/1991 |
| EP | 0515107 A2 * | 5/1992 |
| EP | 0496617 | 7/1992 |
| EP | 0515107 | 11/1992 |
| EP | 0666079 | 8/1995 |
| EP | 0667349 | 8/1995 |
| EP | 0976753 | 2/2000 |
| EP | 0976755 | 2/2000 |
| EP | 0992510 | 4/2000 |
| EP | 1221444 | 1/2001 |
| EP | 1116722 | 7/2001 |
| EP | 1300147 | 4/2003 |
| FR | 223066 | 5/1974 |
| JP | 56131586 | 10/1981 |
| JP | 56131587 | 10/1981 |
| JP | 59062595 | 4/1984 |
| JP | 60140335 | 7/1985 |
| JP | 04036284 | 2/1992 |
| WO | WO9320078 | 10/1993 |
| WO | WO9413643 | 6/1994 |
| WO | WO9413677 | 6/1994 |

(Continued)

OTHER PUBLICATIONS

Baraldi et al., European Journal of Medicinal Chemistry 38: 367-382, 2003.*

(Continued)

*Primary Examiner*—Venkataraman Balasubramanian
(74) *Attorney, Agent, or Firm*—Fish & Richardson P.C.

(57) ABSTRACT

The invention is based on the discovery that compounds of formula (I) possess unexpectedly high affinity for the $A_{2a}$ adenosine receptor, and can be useful as antagonists thereof for preventing and/or treating numerous diseases, including Parkinson's disease. In one embodiment, the invention features a compound of formula I: (I)

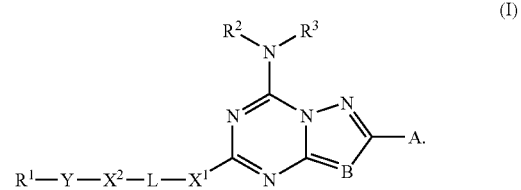

36 Claims, No Drawings

FOREIGN PATENT DOCUMENTS

| WO | WO9417803 | 8/1994 |
|---|---|---|
| WO | WO9713676 | 4/1997 |
| WO | WO9901439 | 1/1999 |
| WO | WO9901454 | 1/1999 |
| WO | WO9943678 | 2/1999 |
| WO | WO9921617 | 5/1999 |
| WO | WO9940091 | 8/1999 |
| WO | WO9948903 | 9/1999 |
| WO | WO9962518 | 12/1999 |
| WO | WO0017201 | 3/2000 |
| WO | WO0061586 | 10/2000 |
| WO | WO0102400 | 1/2001 |
| WO | WO0102409 | 1/2001 |
| WO | WO0162233 | 8/2001 |
| WO | WO03020723 | 3/2003 |
| WO | WO03048163 | 6/2003 |
| WO | WO03068776 | 8/2003 |
| WO | WO2004029056 | 4/2004 |

OTHER PUBLICATIONS

Koretskaya et al., Khim.-Farm. Zh. I (1968) 2(6) 5-12.
Mamaev et al., Getertsikl, Soedin, (1971) 7, 535.
Pendergast et al., J. Chem. Soc. Perkin. Trans. (1973) 1, 2759-2763.
Machon et al., J. Pharmacol. Pharm. (1976) 28, 511.
Higashino et al., Chem Pharm Bull 24, 238-52 (1976).
Higashino et al., Chem Pharm Bull 24, 3120-34 (1976).
Hayashi et al., Yakugaku Zasshi 98, 891 (1978) Abstract.
Robev et al., Dokl. Bolg. Akad. Nauk. (1978) 31, 1131-1134.
Higashino et al., Chem. Pharm. Bull. (1979) 27, 2431.
Higashino et al., Chem. Pharm. Bull. (1979) 27, 3176.
Higashino et al., Fukusokan Kagaku Toronkai Koen Yoshishu, 12th, 1979, 171-5 (Japanese language Conference Report).
Press et al., J. Org. Chem. 48, 4605 (1983).
Schechter et al (1985) J Clin Pharmacol 25, 276.
Higashino et al., Chem Pharm Bull 33, 950 (1985).
Bruns et al., (1986) Mol. Pharmacol. 29: 331-346.
Higashino et al., Chem Pharm Bull 34, 4352 (1986).
Higashino et al., Chem Pharm Bull 34, 4569 (1986).
Molina et al., Tetrahedron Letters (1987) 28, 4451-4454.
Higashino et al., Chem Pharm Bull 35, 4078 (1987).
Jaskolski et al., Acta Crystallogr Sect. C, (1987) C43, 2110-2113.
Molina et al., J. Org. Chem., (1988) 53, 4653-63.
Miyashita et al., Chem Pharm Bull 38, 230(1990).
Hamamichi et al., J. Heterocycl. Chem (1990) 31, 321.
Hamamichi et al., J. Heterocycl. Chem (1990) 27, 835.
Skalski et al., Can. J. Chem (1990) 68, 2164-2170.
Jacobsen et al., J. Med. Chem. (1992) 35(3), 407-423.
Chemical Abstracts, V. 118, No. 3 (1993) Abstract # 22077 Suzuki, Hitomi et al (J. Org. Chem (1993) 58(1) 241-4).
Chemical Abstracts, V. 121, No. 9 (1994) Abstract # 108677 Bouillon et al (Heterocycles (1994) 37(2) 915-32).
Gunderson, Tetrahedron Lett (1994) 35, 3155.
Colotta et al., Eur. J. Jed. Chem. (1995) 30(2), 133-139.
Gundersen et al., Tetrahedron Letters (1995) 36(11), 1945-1948.
Stevenson et al., Tetrahedron Lett. (1996) 37, 8375-8378.
Langli et al., Tetrahedron, vol. 52, Issue 15, Apr. 8, 1996, pp. 5625-5638.
Bertorelli et al (1996) Drug Development Research 37, Issue 2, pp. 65-72.
Prassad et al., Tetrahedron (1997) 53, 7237-7254.
Chebib et al., Bioorganic & Med. Chem Lett (1997) 5(2) 311-322.
Biraldi et al., J. Med. Chem. (1998) 41, 2126-2133.
Francis et al., J. Med. Chem. (1998) 31, 1014-1020.
Monopoli et al. (1998) J Pharmacol Exp Ther 285 (1): 9.
Kim et al., Arch. Pharmacal. Res. (1998) 21, 458-464.
Molina et al., J. Org. Chem. (1998) 53, 4653-4663.
Suzuki et al., Chem Pharm Bull 46, 199 (1998).
Monopoli et al (1998) NeuroReport 9, 3955-3959.
Strappaghetti et al, Eur. J. Med. Chem (1998) 33, 501-508.
Chorvat et al., J. Med. Chem. (1999) 42(5), 833-848.
Betti et al., *Eur. J. Med Chem* (1999) 34(10) 867-875.
Cocuzza et al., Bioorganic & Med. Chem Lett (1999) 9(7) 1063-1066.
Fredholm et al., (1999) Pharmacol Rev. 51, 83-133.
Kopf et al. (1999) Psychopharmacol., 146, 214-219.
Li et al (1999) Experimental Eye Research 68, 9-17.
Svenningsson et al (1999) Progress in Neurobiology 59, 355-396.
Alarcon et al, Tetrahedron Lett (2000) 41, 7211-7215.
Alarcon et al, Bioorg Med Chem Lett (2001) 11, 1855-1858.
Stone et al., (2001) Drug Development Research 52, 323.
Scammell et al., (2001) Neuroscience 107, 653.
El Yacoubi et al., (2001) British Journal of Pharmacology 134, 68-77.
Kase (2001) Bioscience, Biotechnology, and Biochemistry 65, 1447-1457.
Behan et al., (2002) British Journal of Pharmacology (2002) 135, 1435-1442.
Ikeda et al (2002) J Neurochem. 80, 262-70.
Bastia et al., (2002) Neuroscience Letters 328, 241-244.
Hauser et al (2003) Neurology 61 297.
Urade et al (2003) Neurology 2003;61:S94-S96.
Varani et al. (2003) FASEB J. 17, 2148-2150.
Dall'lgna et al., (2003) Br J Pharmacol 138: 1207-1209.
Chase et al., (2003) Neurology 2003;61:S107-S111.
Bara-Jimenez et al., Neurology 2003 61: 293-296.
Bailey et al. J. Neurosci. 22 (21): 9210-9220.

\* cited by examiner

TRIAZOLOTRIAZINES AND PYRAZOLOTRIAZINES AND METHODS OF MAKING AND USING THE SAME

This application is 371 of PCT/US04/11005, filed Apr. 09, 2004, which claims benefit of U.S. Provisional Application No. 60/461,356, filed on Apr. 09, 2003.

BACKGROUND OF THE INVENTION

Adenosine is a ubiquitous biochemical messenger. Adenosine binds to and activates certain seven transmembrane-spanning G-protein coupled receptors, eliciting a variety of physiological responses. Adenosine receptors are divided into four known subtypes (i.e. $A_1$, $A_{2a}$, $A_{2b}$, and $A_3$). These receptor subtypes mediate different and sometimes opposing effects. In general, activation of the adenosine $A_{2a}$ or $A_{2b}$ receptor leads to an increase in cellular cAMP levels, while activation of the adenosine $A_1$ or $A_3$ receptor leads to a decrease in cellular cAMP levels. $A_{2a}$ adenosine receptors are abundant in the basal ganglia, a region of the brain associated with the pathphysiology of Parkinson's disease. For reviews concerning $A_{2a}$ adenosine receptors, see, e.g., Moreau et al., Brain Research Reviews 31:65-82 (1999) and Svenningsson et al., Progress in Neurobiology 59:355-396 (1999). For a discussion of the role and regulation of adenosine in the central nervous system, see, e.g., Dunwiddie et al., Ann. Rev. Neuroscience 24:31-55 (2001).

SUMMARY OF THE INVENTION

The invention is based on the discovery that compounds of formula (I) are inexpectedly potent antagonists of the $A_{2a}$ subtype of adenosine receptors. Many compounds of formula (I) also selectively inhibit the $A_{2a}$ adenosine receptors. Adenosine antagonists of the present invention are useful in the prevention and/or treatment of various diseases and disorders related to modulation of $A_{2a}$ adenosine receptor signaling pathways. Such a disease or disorder can be, e.g., neurodegenerative diseases such as Parkinson's disease and Parkinson's-like syndromes such as progressive supranuclear palsy and multiple system atrophy, senile dementia such as Alzheimer's disease, depression, AIDS encephalopathy, multiple sclerosis, amyotrophic lateral sclerosis, migraine, attention deficit disorder, narcolepsy, sleep apnea or other disorders that cause excessive daytime sleepiness, Huntington's disease, cerebral ischemia, brain trauma, hepatic fibrosis, cirrhosis, and fatty liver.

In one aspect, the invention features compounds of formula (I):

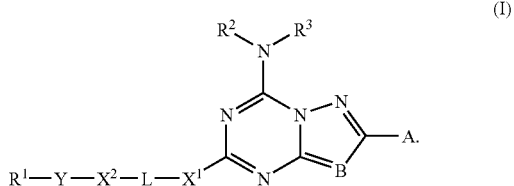

A can be aryl or heteroaryl. B can be N or $CR^2$. Each of $R^2$ and $R^3$, independently, can be hydrogen, alkyl, cycloalkyl, cycloalkenyl, aryl, aralkyl, neterocycloalkyl, heterocycloalkenyl, heteroaryl, or heteroaralkyl. Each of $X^1$ and $X^2$, independently, can be $C_{1-6}$ alkylene, $C_{2-6}$ alkenylene, $C_{2-6}$ alkynylene, or a bond. L can be a bond or a linker selected from the group consisting of:

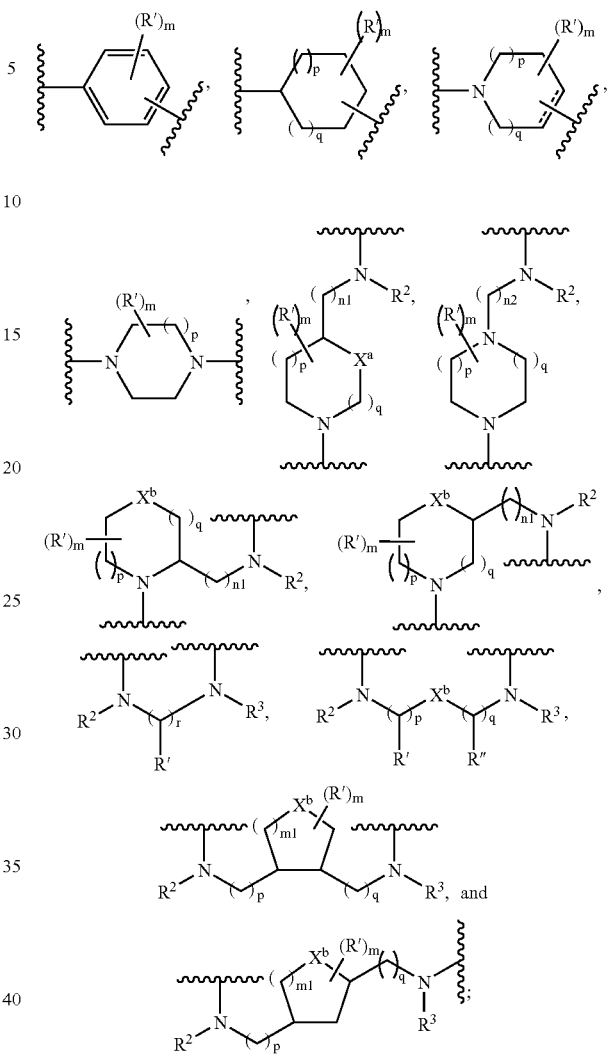

wherein each of R' and R", independently, can be hydrogen, alkyl, alkenyl, alkynyl, alkoxy, acyl, halo, hydroxy, amino, nitro, oxo, thioxo, cyano, guanadino, amidino, carboxy, sulfo, sulfoxy, mercapto, alkylsulfanyl, alkylsulfinyl, alkylsulfonyl, aminocarbonyl, alkylcarbonylamino, alkylsulfonylamino, alkoxycarbonyl, alkylcarbonyloxy, urea, thiourea, sulfamoyl, sulfamide, carbamoyl, cycloalkyl, cycloalkyloxy, cycloalkylsulfanyl, heterocycloalkyl, heterocycloalkyloxy, heterocycloalkylsulfanyl, aryl, aryloxy, arylsulfanyl, aroyl, heteroaryl, heteroaryloxy, heteroarylsulfanyl, or heteroaroyl; provided that two adjacent R' groups can join together to form a 4- to 8-membered optionally substituted cyclic moiety; $X^a$ can be —$C(R^2)(R^3)$—, —S—, —SO—, or —$SO_2$—; $X^b$ can be —$C(R^2)(R^3)$—, —$NR^2$, —O—, —S—, —SO—, or —$SO_2$—; each of p, q, m, and m1, independently, can be 0-3; r can be 1 or 2; n1 can be 0-6; and n2 can be 2-6. Y can be —$C(R^2)(R^3)$—, —O—, —S—, —SO—, —$SO_2$—, —CO—, —$CO_2$—, or a bond. $R^1$ can be alkyl, alkenyl, alkynyl, cycloalkyl, cycloalkylalkyl, cycloalkenyl, cycloalkenylalkyl, aryl, aralkyl, heterocyclyl, or heterocyclylalkyl. It is provided that when $X^1$ is a bond and L is

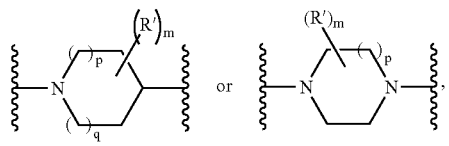

then $X^2$ is alkylene and $R^1$ is heteroaryl. It is further provided that when L is a bond, $X^1$ is an alkynylene.

In one embodiment, L can be

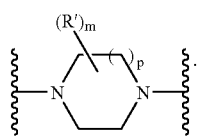

For example, p can be 1 or 2; m can be 0 or m can be 1 and R' is $C_{1-4}$ alkyl. In one embodiment, $X^1$ can be a bond and $X^2$ can be an alkylene. In one embodiment, $R^1$ can be furyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, triazinyl, quinolinyl, isoquinolinyl, indolyl, isoindolyl, benzofuryl, benzothiophenyl, benzimidazolyl, benzthiazolyl, furopyridyl, or thienopyridyl. $R^1$ can be optionally (i.e., $R^1$ can be unsubstituted or substituted) substituted with $C_{1-4}$ alkyl, halo, hydroxy, $C_{1-4}$ alkoxy, or $C_{1-4}$ alkylthio. Some examples of the optional $R^1$ substituents are methyl, ethyl, propyl, fluoro, chloro, bromo, hydroxy, methoxy, ethoxy, propoxy, trifluoromethyl, hydroxymethyl, hydroxyethyl, hydroxypropyl, methylthio, ethylthio, or propylthio.

In one embodiment, L is

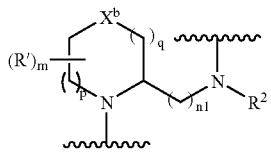

and n1 is 0-2. For example, $X^b$ can be —C($R^2$)($R^3$)— (e.g., —CH$_2$—); p can be 0-1; and q can be 1. In one embodiment, $X^1$ can be a bond. In one embodiment, $X^2$ can be an alkylene that is optionally substituted with $C_{1-4}$ alkyl, halo, hydroxy, $C_{1-4}$ alkoxy, or $C_{1-4}$ alklylthio. In one embodiment, $R^2$ can be hydrogen or $C_{1-4}$ all. In one embodiment, $R^1$ can be alkyl, aryl, or heteroaryl. Some examples of $R^1$ are phenyl, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, triazinyl, quinolinyl, isoqinolinyl, indolyl, isoindolyl, benzofuryl, benzothiophenyl, benzimidazolyl, benzthiazolyl, furopyridyl, or thienopyridyl; each of these groups can be optionally substituted with $C_{1-4}$ alkyl, halo, hydroxy, $C_{1-4}$ alkoxy, or $C_{1-4}$ alkylthio. As another example, $X^b$ can be —N$R^2$—, —O—, —S—, —SO—, or —SO$^2$—; p can be 0-1; and q can be 1.

In one embodiment, L can be

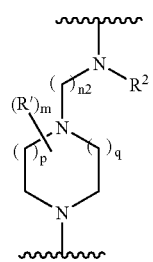

and n2 can be 2-3. For example, p can be 0 or 1, q can be 1, R' can be hydrogen or $C_{1-4}$ alkyl, and m can be 1-2. In one embodiment, $X^1$ can be a bond. In one embodiment, $X^2$ can be a bond or an alkylene that is optionally substituted with $C_{1-4}$ alkyl, halo, hydroxy, $C_{1-4}$ alkoxy, or $C_{1-4}$ alkylthio. In one embodiment, $R^1$ can be alkyl, aryl, or heteroaryl. Some examples of $R^1$ are phenyl, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, triazinyl, quinolinyl, isoquinolinyl, indolyl, isoindolyl, benzofuryl, benzothiophenyl, benzimidazolyl, benzthiazolyl, furopyridyl, or thienopyridyl; each of these groups is optionally substituted with $C_{1-4}$ alkyl, halo, hydroxy, $C_{1-4}$ alkoxy, or $C_{1-4}$ alkylthio.

In one embodiment, L can be a bond and $R^1$ can be alkyl, cycloalkyl, aryl, or heterocyclyl.

In one embodiment, $X^1$ can be a bond or an alkynylene. For example, $X^1$ is a bond.

In one embodiment, $X^2$ can be a bond or an alkylene; and $X^1$ can be an $C_{1-4}$ alkylene that is optionally substituted with $C_{1-4}$ alkyl.

In one embodiment, Y can be —SO$_2$—, —CO—, —CO$_2$—, or a bond.

In one embodiment, $R^1$ can be alkyl, aryl, or heteroaryl. For example, $R^1$ can be $C_{1-4}$ alkyl, phenyl, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, triazinyl, quinolinyl, isoquinolinyl, indolyl, isoindolyl, benzofuryl, benzothiophenyl, benzimidazolyl, benzthiazolyl, furopyridyl, or thienopyridyl.

Some examples of a compound of formula (I) are shown in Examples 1-214 below.

An N-oxide derivative or a pharmaceutically acceptable salt of each of the compounds of formula (I) is also within the scope of this invention. For example, a nitrogen ring atom of the triazolotriazine or the pyrazolotriazine core ring or a nitrogen-containing heterocyclyl substituent can form an oxide in the presence of a suitable oxidizing agent such as m-chloroperbenzoic acid or $H_2O_2$.

A compound of formula (I) that is acidic in nature (e.g., having a carboxyl or phenolic hydroxyl group) can form a pharmaceutically acceptable salt such as a sodium, potassium, calcium, or gold salt. Also within the scope of the invention are salts formed with pharmaceutically acceptable amines such as ammonia, alkyl amines, hydroxyalkylamines, and N-methylglycamine. A compound of formula (I) can be treated with an acid to form acid addition salts. Examples of such an acid include hydrochloric acid, hydrobromic acid, hydroiodic acid, sulfuric acid, methanesulfonic acid, phosphoric acid, p-bromophenyl-sulfonic acid, carbonic acid, succinic acid, citric acid, benzoic acid, oxalic acid, malonic acid, salicylic acid, malic acid, fumaric acid, ascorbic acid, maleic acid, acetic acid, and other mineral and organic acids well known to a skilled person in the art. The acid addition salts can be prepared by treating a compound of formula (I) in its free base form with a sufficient amount of an acid (e.g., hydrochloric acid) to produce an acid addition salt (e.g., a hydrochloride salt). The acid addition salt can be converted back to its free base form by treating the salt with a suitable dilute aqueous basic solution (e.g., sodium hydroxide, sodium bicarbonate, potassium carbonate, or ammonia). Compounds of formula (I) can also be, e.g., in a form of achiral compounds, racemic mixtures, optically active compounds, pure diastereomers, or a mixture of diastereomers.

Compounds of formula (I) exhibit surprisingly high affinity to the $A_{2a}$ subtype of adenosine receptors, e.g., with $K_i$ values of less than 10 µM under conditions as described in Example 215. Some compounds of formula (I) exhibit $K_i$ values of below 1 µM. Many compounds of formula (I) are selective inhibitors of the $A_{2a}$ adenosine receptors (e.g., these compounds inhibit the $A_{2a}$ adenosine receptors at least 10 times better than other subtypes of adenosine receptors, e.g., the $A_1$ adenosine receptors or the $A_3$ adenosine receptors).

Compounds of formula (I) can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom-substitution in aromatic rings.

In another aspect, the present invention features a pharmaceutical composition comprising a compound of formula (I) (or a combination of two or more compounds of formula (I)) and a pharmaceutically acceptable carrier. Also included in the present invention is a medicament composition including any of the compounds of formula (I), alone or in a combination, together with a suitable excipient.

In a further aspect, the invention features a method of inhibiting the $A_{2a}$ adenosine receptors (e.g., with an $K_i$ value of less than 10 µM; preferably, less than 1 µM) in a cell, including the step of contacting the cell with an effective amount of one or more compounds of formula (I). Also with the scope of the invention is a method of modulating the $A_{2a}$ adenosine receptor signaling pathways in a cell or in a subject (e.g., a mammal such as human), including the step of contacting the cell with or administering to the subject an effective amount of one or more of a compound of formula (I).

Also within the scope of the present invention is a method of treating a subject or preventing a subject suffering from a condition or a disease wherein the causes or symptoms of the condition or disease are associated with an activation of the $A_{2a}$ adenosine receptor. The method includes the step of administering to the subject an effective amount of one or more of a compound of formula (I). The conditions or diseases can be, e.g., neurodegenerative diseases such as Parkinson's disease and Parkinson's-like syndromes such as progressive supranuclear palsy and multiple system atrophy, senile dementia such as Alzheimer's disease, depression, AIDS encephalopathy, multiple sclerosis, amyotrophic lateral sclerosis, migraine, attention deficit disorder, narcolepsy, sleep apnea or other disorders that cause excessive daytime sleepiness, Huntington's disease, cerebral ischemia, brain trauma, hepatic fibrosis, cirrhosis, and fatty liver.

Compounds of formula (I) may be utilized as sedatives, muscle relaxants, antipsychotics, antidepressants, anxiolytics, analgesics, respiratory stimulants, antiepileptics, anticonvulsants, and cardioprotective agents.

Also within the scope of the invention is a method of treating or preventing a condition or a disease characterized by or resulted from an over-activation of the $A_{2a}$ adenosine receptor by administering to a subject in need of such a treatment an effective amount of any of compounds of formula (I) in combination with one or more known $A_{2a}$ antagonists. For example, a patient suffering from Parkinson's disease can be treated by administering an effective amount of a compound of formula (I) in combination with an agent such as L-DOPA, a dopaminergic agonist, an inhibitor of monoamine oxidase (type B), a DOPA decarboxylase inhibitor, or a catechol-O-methyltransferase inhibitor. The compound of formula (I) and the agent can be administered to a patient simultaneously or in sequence. The invention also includes a pharmaceutical composition containing one or more of a compound of formula (I) one or more of a known $A_{2a}$ antagonist, and a suitable excipient.

As used herein, an "alkyl" group refers to a saturated aliphatic hydrocarbon group containing 1-8 (e.g., 1-6 or 1-4) carbon atoms. An alkyl group can be straight or branched. Examples of an alkyl group include, but are not limited to, methyl, ethyl, propyl, isopropyl, butyl, isobutyl, sec-butyl, tert-butyl, n-pentyl, n-heptyl, and 2-ethylhexyl. An alkyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy. An "alkylene" is a divalent alkyl group, as defined herein.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy. An "alkenylene" is a divalent alkenyl group, as defined herein.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, alkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy. An "alkynylene" is a divalent alkynyl group, as defined herein.

As used herein, an "amino" group refers to —NR$^X$R$^Y$ wherein each of R$^X$ and R$^Y$ is independently hydrogen, alkyl, cycloalkyl, (cycloalkyl)alkyl, aryl, aralkyl, heterocycloalkyl, (heterocycloalkyl)alkyl, heteroaryl, or heteroaralkyl. When the term "amino" is not the terminal group (e.g., alkylcarbonylamino), it is represented by —NR$^X$—. R$^X$ has the same meaning as defined above.

As used herein, an "aryl" group refers to phenyl, naphthyl, or a benzofused group having 2 to 3 rings. For example, a benzofused group includes phenyl fused with one or two $C_{4-8}$ carbocyclic moieties, e.g., 1, 2, 3, 4-tetrahydronaphthyl, indanyl, or fluorenyl. An aryl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl.

As used herein, a "cycloalkyl" group refers to an aliphatic carbocyclic ring of 3-10 (e.g., 4-8) carbon atoms. Examples of cycloalkyl groups include cyclopropyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, and bicyclo[3.2.3]nonyl. A "cycloalkenyl" group, as used herein, refers to a non-aromatic carbocyclic ring of 3-10 (e.g., 4-8) carbon atoms having one or more double bond. Examples of cycloalkenyl groups include cyclopentenyl, 1,4-cyclohexadi-enyl, cycloheptenyl, cyclooctenyl, hexahydro-indenyl, octahydro-naphthyl, bicyclo[2.2.2]octenyl, and bicyclo[3.3.1]nonenyl,. A cycloalkyl or cycloalkenyl group can be optionally substituted with one or more substituents such as alkyl (including-carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, a "heterocycloalkyl" group refers to a 3- to 10-membered (e.g., 4- to 8-membered) saturated ring structure, in which one or more of the ring atoms is a heteroatom, e.g., N, O, or S. Examples of a heterocycloalkyl group include piperidinyl, piperazinyl, tetrahydropyranyl, tetrahydrofuryl, dioxolanyl, oxazolidinyl, isooxazolidinyl, morpholinyl, octahydro-benzofuryl, octahydro-chromenyl, octahydro-thiochromenyl, octahydro-indolyl, octahydro-pyrindinyl, decahydro-quinolinyl, octahydro-benzo[b]thiophenyl, 2-oxa-bicyclo[2.2.2]octyl, 1-aza-bicyclo[2.2.2]octyl, 3-aza-bicyclo[3.2.1]octyl, anad 2,6-dioxa-tricyclo[3.3.1.0$^{3,7}$]nonyl. A "heterocycloalkenyl" group, as used herein, refers to a 3- to 10-membered (e.g., 4- to 8-membered) non-aromatic ring stracture having one or more double bonds, and wherein one or more of the ring atoms is a heteroatom, e.g., N, O, or S. A heterocycloalkyl or heterocycloalkenyl group can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

A "heteroaryl" group, as used herein, refers to a monocyclic, bicyclic, or tricyclic ring structure having 5 to 15 ring atoms wherein one or more of the ring atoms is a heteroatom, e.g., N, O, or S and wherein one ore more rings of the bicyclic or tricyclic ring structure is aromatic. Some examples of heteroaryl are pyridyl, furyl, pyrrolyl, thienyl, thiazolyl, oxazolyl, imidazolyl, indolyl, tetrazolyl, benzofuryl, benzthiazolyl, xanthene, thioxanthene, phenothiazine, dihydroindole, and benzo[1,3]dioxole. A heteroaryl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl. A "heteroaralkyl" group, as used herein, refers to an alkyl group (e.g., a $C_{1-4}$ alkyl group) that is substituted with a heteroaryl group. Both "alkyl" and "heteroaryl" have been defined above.

As used herein, "cyclic moiety" includes cycloalkyl, heterocycloalkyl, cycloalkenyl, heterocycloalkenyl, aryl, or heteroaryl, each of which has been defined previously.

As used herein, an "acyl" group refers to a formyl group or alkyl-C(═O)— where "alkyl" has been defined previously. Acetyl and pivaloyl are examples of acyl groups.

As used herein, a "carbamoyl" group refers to a group having the structure —O—CO—NR$^X$R$^Y$ or —NR$^X$—CO—O—R$^Z$ wherein R$^X$ and R$^Y$ have been defined above and R$^Z$ is alkyl, cycloalkyl, (cycloalkyl)alkyl, aryl, aralkyl, heterocycloalkyl, (heterocycloalkyl)alkyl, heteroaryl, or heteroaralkyl.

As used herein, a "carboxy" and a "sulfo" group refer to —COOH and —SO$_3$H, respectively.

As used herein, an "alkoxy" group refers to an alkyl-O— group where "alkyl" has been defined previously.

As used herein, a "sulfoxy" group refers to —O—SO—R$^X$ or —SO—O—R$^X$, where R$^X$ has been defined above.

As used herein, a "halogen" or "halo" group refers to fluorine, chlorine, bromine or iodine.

As used herein, a "sulfamoyl" group refers to the structure —SO$_2$—NR$^X$R$^Y$ or —NR$^X$—SO$_2$—R$^Z$ wherein R$^X$, R$^Y$, and R$^Z$ have been defined above.

As used herein, a "sulfamide" group refers to the structure —NR$^X$—S(O)$_2$—NR$^Y$R$^Z$ wherein R$^X$, R$^Y$, and R$^Z$ have been defined above.

As used herein, a "urea" group refers to the structure —NR$^X$—CO—NR$^Y$R$^Z$ and a "thiourea" group refers to the structure —NR$^X$—CS—NR$^Y$R$^Z$. R$^X$, R$^Y$, and R$^Z$ have been defined above.

As used herein, an effective amount is defined as the amount which is required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height-and weight of the patient. See, e.g., Scientific Tables, Geigy Pharmaceuticals, Ardsley, N.Y., 537 (1970). As used herein, "patient" refers to a mammal, including a human.

An antagonist is a molecule that binds to the receptor without activating the receptor. It competes with the endogenous ligand(s) or substrate(s) for binding site(s) on the receptor and, thus inhibits the ability of the receptor to transduce an intracellular signal in response to endogenous ligand binding.

As compounds of formula (I) are antagonists of the A$_{2a}$ subtype of the adenosine receptors, these compounds are useful in inhibiting the consequences of signal transduction through the adenosine A$_{2a}$ receptor. Thus, compounds of formula (I) possess the therapeutical utility of treating and/or preventing disorders or diseases for which inhibition of the adenosine A$_{2a}$ receptor signaling pathways is desirable (e.g. Parkinson's disease or depression).

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In addition, the materials, methods, and examples are illustrative only and not intended to be limiting.

Other features and advantages of the invention will be apparent from the following detailed description, and from the claims.

DETAILED DESCRIPTION OF THE INVENTION

Unless otherwise defined, all technical and scientific terms used herein have the same metang as commonly understood by one of ordinary skill in the art to whlch this invention belongs. Although methods and materials similar or equivalent to those described herein can be used in the practice or testing of the present invention, suitable materials and methods are described below. All publications, patent applications, patents, and other references mentioned herein are incorporated by reference in their entirety. In addition, the materials, methods, and examples are illustrative only and are not intended to be limiting Synthesis of the Adenosine Antagonist Compounds Compounds of formula (I) may be prepared by a number of known methods from commercially available or known starting materials.

In one method, a compound of formula (I) is prepared according to the method outlined in Scheme 1 below. Specifically, the method utilizes a sulfone starting material (II). This starting material, wherein X$^1$ is a bond, can be prepared according to known methods, e.g., see Caulkett et al., *J. Chem. Soc. Perkin Trans I.* 801-808 (1995) and de Zwart et al., *Drug Dev. Res.* 48:95-103 (1999). Note that one can also employ a starting material containing a halo (e.g., a chloro, see compound (III) in Scheme 1) instead of a sulfone group. See, e.g., U.S. Pat. No. 6,222,035, which can be modified to produce the starting material (III). Starting materials wherein X$^1$ is not a bond (e.g., X$^1$ is an alkynylene) can be prepared in many known methods. For example, one can react compound (II) wherein X$^1$ is a bond (e.g., 2-furan-2-yl-5-methanesulfonyl-[1,2,4]triazolo[1,5-a][1,3,5]triazin-7-ylamine) with an appropriate nucleophile (e.g., methylsulfanylethyne or chloroethyne in the presence of a palladium catalyst such as palladium tetrakistriphenylphosphine) to form an intermediate, which can be followed by further modifications such as oxidation of the methylsulfanyl group to methylsulfonyl group to form a starting material (II) wherein X$^1$ is an alkynylene.

According to the method depicted in Scheme 1, the starting material (II) or (III) can react with a nucleophilic compound L (as defined above). When L is a symmetrical diamine (e.g., piperidine), it is unnecessary to use a protecting group, and an excess of unprotected L (e.g., 3 to 5 molar equivalents) can directly react with the starting material (II) or (III) to form an intermediate (IV). The reaction can be carried out in an appropriate solvent such as acetonitrile (CH$_3$CN), dimethyl sulfoxide (DMSO), or N,N-dimethylformamide (DMF) at a temperature ranging from about 80° C. to about 120° C. The intermediate (IV) can further react, via the free amino group of moiety L, with a compound of the formula R$^1$—Y—X$^2$-LG (where R$^1$, Y, and X$^2$ have been defined above and LG represents an appropriate leaving group such as halide, mesylate, or tosylate) to form a desired compound of formula (I). See Route (A) below and Examples 2 and 3.

Alternatively, the intermediate (IV) can react with an appropriate aldehyde or carboxylic acid to form an amide, which can then undergo reductive amination to form a desired compound of formula (I). Examples of a typical reducing agentused in this reaction are sodium triacetoxyborohydride, sodium cyanoborohydride, and borane THF. See Route (B) below and Example 1.

Still another alternative involves reacting the intermediate (IV) with an appropriate epoxide to form a desired compound of formula (I). See Route (C) below. Note that the reaction between moiety L and the epoxide ring leads to opening of the ring, thus forming a hydroxy-containing moiety $X^2$. Moiety $X^{2a}$ and hydroxyethylene group (from the epoxide ring) together form moiety $X^2$ (see route (C) shown in Scheme 1 below).

a hydroxyalkyl substituted piperidine or piperazine, which can coupled to moiety $X^1$ or the fused core ring (when $X^1$ is a bond) of the starting material to form the intermediate (V).

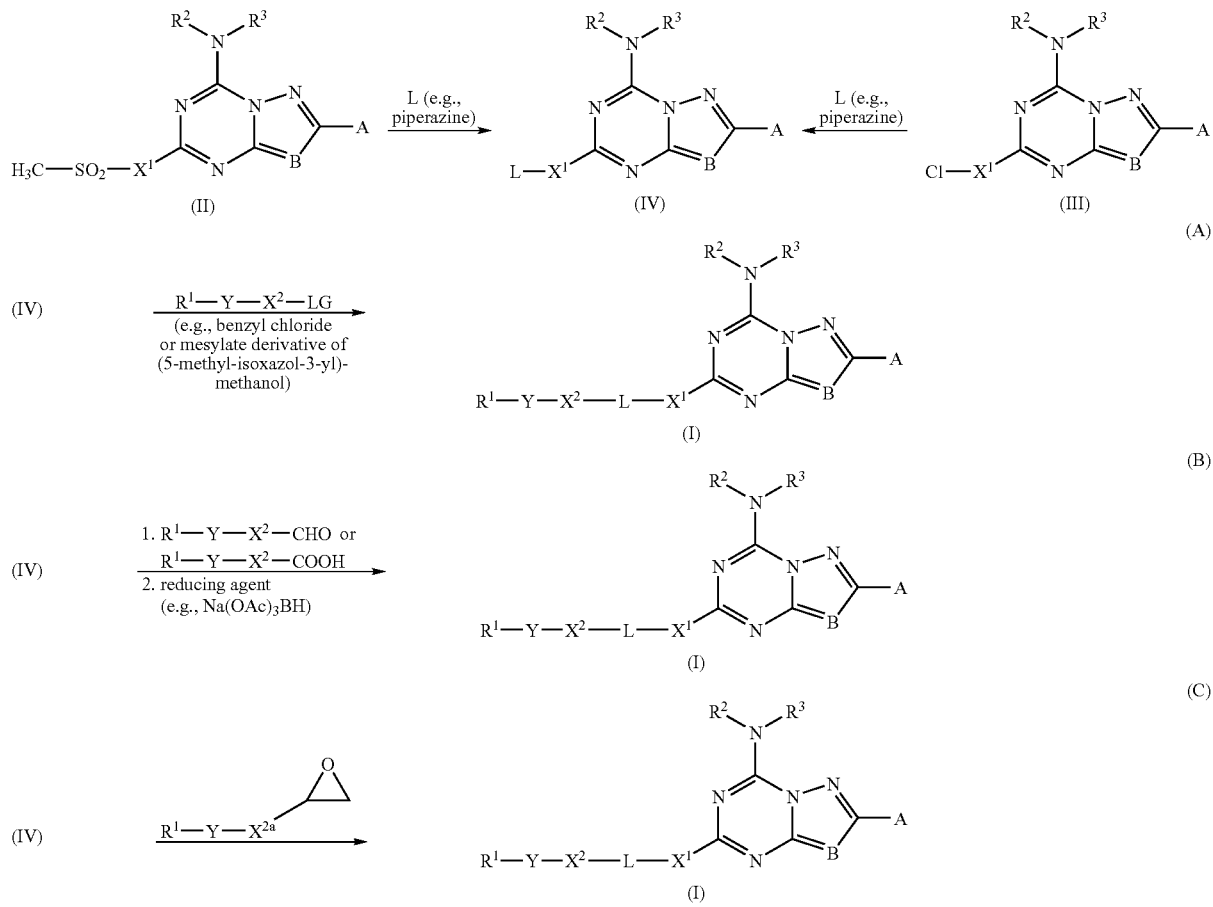

As apparent to a skilled person in the art, in the reaction between L and a starting material of formula (II) or formula (III), if L is an asymmetrical diamine (i.e., coupling at one amino group versus the other amino group yields a different compound), the amino group not intended to be connected to $X^1$ or the fused core ring (when $X^1$ is a bond) should be protected (e.g., with an amino protecting group such as tert-butoxycarbonyl (BOC)). The protected compound of formula (IVa) (e.g., 4-(7-amino-2-furan-2-yl-[1,2,4]triazolo[1,5-a][1,3,5]triazin-5-yl)-piperazine-1-carboxylic acid tert-butyl ester) can then undergo deprotection before further reaction with a compound of the formula $R^1$—Y—$X^2$-LG, or an appropriate aldehyde or carboxylic acid, or an appropriate epoxide, as shown in Scheme 1 routes (A), (B), and (C), respectively. See, e.g., Example 6. For reference on protecting groups, see, e.g., Greene and Wutts: *Protective Groups in Organic Synthesis*, $3^{rd}$ edition, John Wiley & Sons (1999).

In another method, a compound of formula (I) can be prepared by reacting the starting material of formula (II) or formula (III) with a compound of the formula L', where L' is the precursor of moiety L. For example, moiety L' can be The hydroxy group of moiety L' can then be converted into an amine, thus forming part of moiety L. This amine can further react with a compound such as $R^1$—Y—$X^2$-LG, or an appropriate aldehyde or carboxylic acid, or an appropriate epoxide to form a compound of formula (I) as depicted in routes (A), (B), and (C) shown above. Scheme 2 below shows a specific example wherein compound L' is piperidin-4-yl-methanol.

Scheme 2

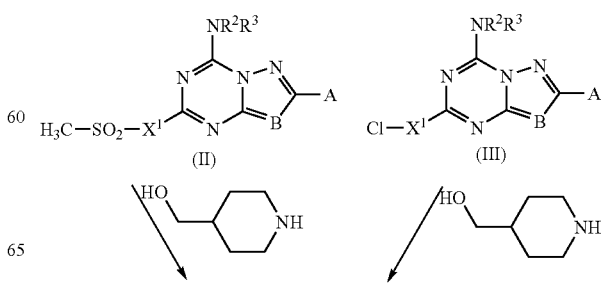

-continued

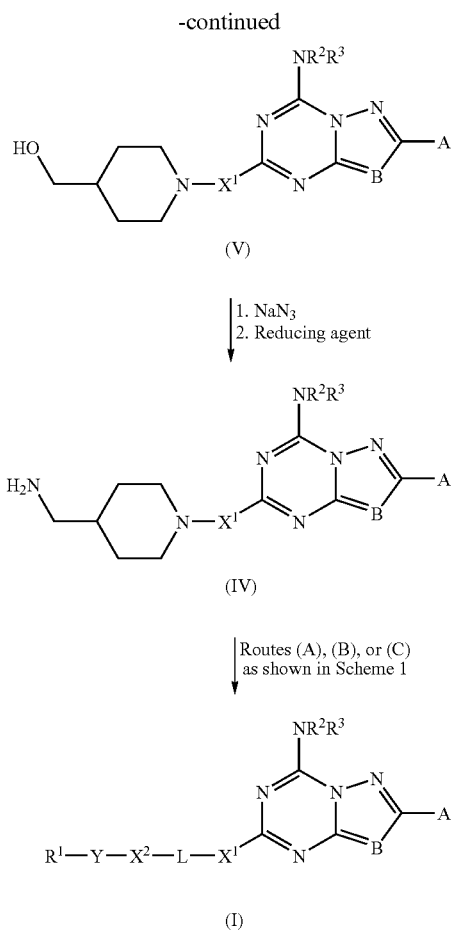

In yet another method, the intermediate (V) as shown in Scheme 2 above can be converted into a leaving group such as a mesylate or tosylate. Further reaction of the mesylate or tosylate with a compound such as R¹—Y—X²-LG, or an appropriate aldehyde or carboxylic acid, or an appropriate epoxide as depicted in routes (A), (B), and (C) of Scheme 1 can lead to a desired compound of formula (I). See Scheme 3 below.

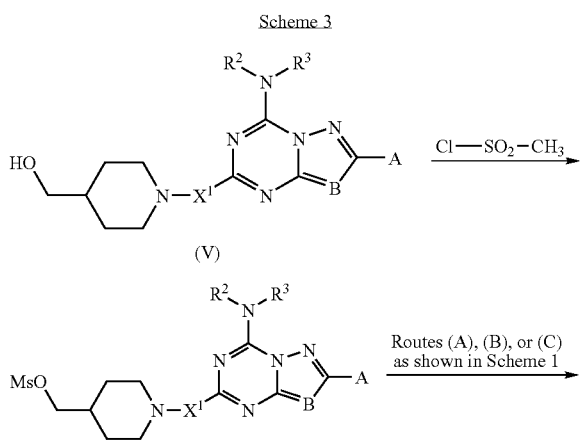

-continued

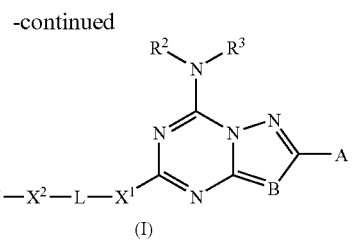

In a further method, $X^1$ can be coupled to a compound of the formula $R^1$—Y—$X^2$-L prior to reacting with a starting material of formula (II) or formula (III). For example, $X^1$ can be propargyl bromide, which can react with 1-(2,4-difluoro-benzyl)-piperazine (an example of a compound of the formula $R^1$—Y—$X^2$-L where $R^1$ is difluoro-substituted phenyl, Y is a bond, $X^2$ is a methylene, and L is piperazine) to form 1-(2,4-difluoro-benzyl)-4-prop-2-ynyl-piperazine, which in turn, can couple with the starting material (II) or (III) to yield a compound of formula (I). The coupling reaction can be carried out in a polar solvent, e.g., DMF, using palladium tetrakistriphenylphosphine in the presence of copper iodide, triphenylphosphine, triethylamine at an elevated temperature, e.g., 100-120° C. For reference, see, e.g., Malleron, J. L. et al., Handbook of Palladium-catalyzed organic reactions, Academic Press, London, England (1997).

In still another method, a compound of formula (I) wherein L is a divalent phenylene can be prepared by using Suzuki coupling reaction as shown in Scheme 4 below. Note that X' is halo and the starting material used in this reaction is the halo starting material of formula (II), e.g., 5-chloro-2-furan-2-yl-[1,2,4]triazolo[1,5-a][1,3,5]triazin-7-ylamine, as described above.

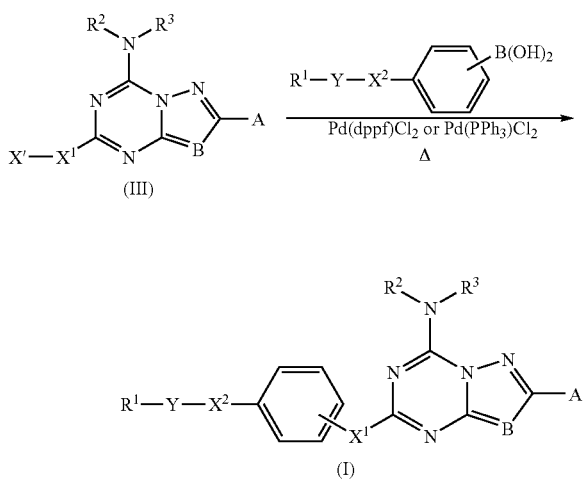

As can be appreciated by a skilled artisan, the above synthetic schemes are exemplary and not intended to comprise a comprehensive list of all means by which the compounds described and claimed in this application may be synthesized. For example, the reaction steps shown in the schemes above can be conducted in a different order, e.g., by reacting a compound of the formula Y—$X^2$-L with the sulfone or chloride starting material before coupling with $R^1$. Further methods will be evident to those of ordinary skill in the art.

Uses for the $A_{2a}$ Adenosine Antagonist Compounds

Compounds of the invention are useful in the prevention and/or treatment of various neurological diseases and disorders whose causes or symptoms are associated with the $A_{2a}$ adenosine receptor signaling pathways. Such diseases and disorders include neurodegenerative diseases such as Parkinson's disease and Parkinson's-like syndromes such as progressive supranuclear palsy and multiple system atrophy, Huntington's disease, depression, anxiety, and cerebrovascular disorders such as migraine. In addition, compositions of the invention are useful for neuroprotection, i.e., to prevent or inhibit neuronal death or degeneration associated with conditions such as senile dementia (e.g., Alzheimer's disease), stroke (cerebral ischemia), and brain trauma.

Administration of Compounds of the Invention

Compounds of the invention can be administered to an animal, preferably a mammal, e.g., a human, non-human primate, dog, pig, sheep, goat, cat, mouse, rat, guinea pig, rabbit, hamster, or marmoset. The compounds can be administered in any manner suitable for the administration of pharmaceutical compounds, including, but not limited to, pills, tablets, capsules, aerosols, suppositories, liquid formulations for ingestion or injection or for use as eye or ear drops, dietary supplements, and topical preparations. The compounds can be administered orally, intranasally, transdermally, intradermally, vaginally, intraaurally, intraocularly, buccally, rectally, transmucosally, or via inhalation, implantation (e.g., surgically), or intravenous administration.

Pharmaceutical Compositions

Compounds of the invention can be formulated into pharmaceutical compositions for administration to animals, including humans. These pharmaceutical compositions preferably include a pharmaceutically acceptable carrier and an amount of $A_{2a}$ adenosine receptor antagonist effective to improve neurological functions such as motor functions and cognitive functions.

Pharmaceutically acceptable carriers useful in these pharmaceutical compositions include, e.g., ion exchangers, alumina, aluminum stearate, lecithin, serum proteins, such as human, serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention can be administered parenterally, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention can be aqueous or oleaginous suspension. These suspensions may be formulated according to techniques known in the art using suitable dispersing or wetting agents and suspending agents. The sterile injectable preparation can also be a sterile injectable solution or suspension in a non-toxic parenterally-acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also can contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable, solid, liquid, or other dosage forms also can be used for the purposes of formulation.

Parenteral formulations can be a single bolus dose, an infusion or a loading bolus dose followed with a maintenance dose. These compositions can be administered once a day or on an "as needed" basis.

The pharmaceutical compositions of this invention be administered orally in any orally acceptable dosage form including, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents can also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically Topical application can be effected in a rectal suppository formulation (see above) or in a suitable enema formulation. Topically-transdermal patches may also be used.

For topical applications, the pharmaceutical compositions can be formulated in a suitable ointment containing the active component suspended or dissolved in one or more carriers. Carriers for topical administration of the compounds of this invention include, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutic compositions may be formulated in an ointment such as petrolatum.

The pharmaceutical compositions of this invention also can be administered by nasal aerosol or inhalation. Such compositions can be prepared according to techniques known in the art of pharmaceutical formulation, and can be prepared as solutions in saline, employing benzyl alcohol or other suitable preservatives, absorption promoters to enhance bioavailability, fluorocarbons, and/or other conventional solubilizing or dispersing agents.

The amount of $A_{2a}$ adenosine receptor antagonist that may be combined with the carrier materials to produce a single dosage form will vary depending upon the host treated and the particular mode of administration. The compositions can be formulated so that a dosage of between 0.01-100 mg/kg body weight of the $A_{2a}$ adenosine receptor antagonist is administered to a patient receiving these compositions. In some embodiments of the invention, the dosage is 0.1-10 mg/kg bodyweight. The composition may be administered as a single dose, multiple doses or over an established period of time in an infusion.

A specific dosage and treatment regimen for any particular-patient will depend upon a variety of factors, including the particular $A_{2a}$ adenosine receptor antagonist, the patient's age, body weight, general health, sex, and diet, and the time of administration, rate of excretion, combination, and the severity of the particular disease being treated. Judgment of such factors by medical caregivers is within ordinary skill in the art. The amount of antagonist will also depend on the individual patient to be treated, the route of administration, the type of formulation, the characteristics of the compound used the severity of the disease, and the desired effect. The amounts of antagonist can be determined by pharmacological and pharmacokinetic principles well-known in the art.

The invention will be further described in the following examples, which do not limit the scope of the invention described in the claims.

In the following examples, unless indicated otherwise, all commercial reagents were obtained from Sigma-Aldrich (St. Louis, Mo.), Lancaster (Windham N.H.), Acros (Pittsburgh, Pa.), Alfa (Berkshire, UK), TCI (Portland, Oreg.), or Maybridge (Cornwall, UK).

EXAMPLE 1

2-Furan-2-yl-5-(4-pyridin-2-ylmethyl-piperazin-1-yl)-[1,2,4]triazolo[1,5-a][1,3,5]triazin-7-ylamine Synthesis of the, title compound is described in parts (a) and (b) below.

(a) 2-Furan-2-yl-5-piperazin-1-yl-[1,2,4]triazolo[1,5-a][1,3,5]triazin-7-ylamine 18 mmol of 2-furan-2-yl-5-methanesulfonyl-[1,2,4]triazolo[1,5-a][1,3,5]triazin-7-ylamine (prepared as described in Caulkett et al., *J. Chem. Soc. Perkin Trans I.* 801-808 (1995)) was suspended in 50 mL of $CH_3CN$ along with 5 eq. of piperazine. The reaction mixture was stirred under reflux for 2 hours. It was then cooled to room temperature and concentrated under reduced pressure. The residue was taken up in $CH_2Cl_2$ and washed with $H_2O$, brine, dried with $Na_2SO_4$, and concentrated under reduced pressure. The resulting crude product was purified by chromatography (95% $CH_2Cl_2$, 4% MeOH, 1% $Et_3N$) to afford 2-furan-2-yl-5-piperazin-1-yl-[1,2,4]triazolo[1,5-a][1,3,5]triazin-7-ylamine. $^1$H NMR (DMSO-$d_6$) δ 8.2 (br s, 2H), 7.85 (d, J=1.0 Hz, 1H), 7.07 (d, J=3.6 Hz, 1H), 6.68 (dd, J=3.6 Hz. 1.0 Hz, 1H), 3.20-2.75 (m, 8H) ppm. MS: m/z=287 [M+H]$^+$.

(b) 2-Furan-2-yl-5-(4-pyridin-2-ylmethyl-piperazin-1-yl)-[1,2,4]triazolo[1,5-a][1,3,5]triazin-7-ylamine 2-Furan-2-yl-5-piperazin-1-yl-[1,2,4]triazolo[1,5-a][1,3,5]triazin-7-ylamine (0.15 mmol) was dissolved in 4 mL of $CH_2Cl_2$ along with 2 eq. of pyridine-2-carbaldehyde and 25 mL of glacial acetic acid. The reaction mixture was stirred at room temperature for 30 minutes and sodium triacetoxyborohydride (4 eq.) was added in a single portion. The resulting reaction mixture was then stirred at room temperature for 18 hours. It was then concentrated under a stream of $N_2$ and purified by preparative HPLC using a mixture of aqueous $CH_3CN$ that has been buffered with 0.1% TFA. $^1$H NMR (DMSO-$d_6$) δ 8.52 (d, J=6.0 Hz, 1H), 7.64-7.60 (m, 1H), 7.50-7.19 (m, 4H), 6.84 (dd, J=3.6 Hz, 1.0 Hz, 1H), 4.09-4.06 (m, 4H), 3.89 (br s, 2H), 2.51-2.41 (m, 4H) ppm. MS: m/z: 378 [M+H]$^+$.

EXAMPLE 2

2-Furan-2-yl-5-[4-(5-methyl-isoxazol-3-ylmethyl)-piperazin-1-yl]-[1,2,4]triazolo[1,5-a][1,3,5]triazin-7-ylamine Synthesis of the title compound is described in parts (a) and (b) below.

(a) Methanesulfonic acid 5-methyl-isoxazol-3-ylmethyl ester (5-Methyl-isoxazol-3-yl)-methanol (32 mg, 0.28 mmol) was dissolved in 4 mL of $CH_2Cl_2$ along with 1.3 eq. of $Et_3N$. The solution was cooled in an ice bath and methanesulfonyl chloride (1.2 eq.) was added. The reaction mixture was warmed to room temperature and stirred for 45 minutes. It was then quenched with brine and the two layers we separated. The organic layer was dried with $Na_2SO_4$ and concentrated under reduced pressure to afford the title mesylate derivative.

(b) 2-Furan-2-yl-5-[4-(5-methyl-isoxazol-3-ylmethyl)-piperazin-1-yl]-[1,2,4]triazolo[1,5-a][1,3,5]triazin-7-ylamine The mesylate derivative from subpart (a) above (0.28 mmol) was added to a solution of 2-furan-2-yl-5-piperazin-1-yl-[1,2,4]triazolo[1,5-a][1,3,5]triazin-7-ylamine (0.14 mmol; see Example 1(a) above) and $Et_3N$ (0.3 mmol) in 3 mL of $CH_3CN$. The resulting reaction mixture was stirred at room temperature for 18 hours. It was then concentrated and purified by preparative HPLC using a mixture of aqueous $CH_3CN$ that has been buffered with 0.1% TFA.

$^1$H NMR (DMSO-$d_6$) δ 7.90 (br s, 2H), 7.80 (d, J=1.0 Hz, 1H), 7.05 (d, J=3.6 Hz, 1H), 6.68 (dd, J=3.6 Hz, 1.0 Hz, 1H), 6.30 (s, 1H), 3.65 (m, 2H), 3.20-2.75 (m, 8H), 2.35 (s, 3H) ppm. MS: m/z: 382 [M+H]$^+$.

EXAMPLE 3

5-[4-(3,5-Dimethyl-isoxazol-4-ylmethyl)-piperazin-1-yl]-2-furan-2-yl-[1,2,4]triazolo[1,5-a][1,3,5]triazin-7-ylamine 4-Chloromethyl-3,5-dimethyl-isoxazole (1.5 eq.) was directly added to a solution of 2-furan-2-yl-5-piperazin-1-yl-[1,2,4]triazolo[1,5-a][1,3,5]triazin-7-ylamine (0.14 mmol; see Example 1(a) above) and $Et_3N$ (0.3 mmol) in 3 mL of $CH_3CN$. The resulting reaction mixture was stirred at room temp for 18 hours. It was then concentrated and purified by preparative HPLC using a mixture of aqueous $CH_3CN$ that has-been buffered with 0.1% TFA. $^1H$ NMR (DMSO-$d_6$) δ 7.60 (d, J=1.0 Hz, 1H), 7.28 (br s, 2H), 7.22 (d, J=3.6 Hz, 1 H), 6.68 (dd, J=3.6 Hz, 1.0 Hz, 1H), 3.8 (br s, 2H), 2.2-3.2 (m, 8H), 1.6 (br s, 6H). MS: m/z 3.96 [M+H]$^+$.

EXAMPLE 4

5-[4-(3,5-Dichloro-pyridin-4-ylmethyl)-piperazin-1-yl]-2-furan-2-yl-[1,2,4]triazolo[1,5-a][1,3,5]triazin-7-ylamine Synthesis of the title compound is described in parts (a) and (b) below.

(a) 3,5-Dichloro-4-chloromethyl-pyridine 3,5-Dichloroisonicotinic acid (5 g) was suspended in 12 mL of thionyl chloride and stirred under reflux for 18 hours. The reaction mixture was concentrated. The resulting acid chloride (1.30 g, 6.2 mmol) was dissolved in 5 mL of 1,4-dioxane at 0° C. The reaction mixture was stirred at 0° C. for 15 minutes and allowed to warm to room temperature and stirred for an additional 30 minutes. It was then cooled to 0° C. and carefully quenched with 15 mL of water. The reaction mixture was extracted with $CH_2Cl_2$ and the combined organic layers were dried with $Na_2SO_4$ and concentrated under reduced pressure. The resulting crude product was purified by chromatography (3:1 hexanes/EtOAc) to afford 650 mg of the alcohol intermediate. This alcohol intermediate was dissolved in 1 mL of thionyl chloride and stirred under reflux for an hour. The resulting reaction mixture was cooled to room temperature and concentrated under reduced pressure to afford the chloromethyl pyridine derivative as a yellow solid.

(b) 5-[4-(3,5-Dichloro-pyridin-4-ylmethyl)-piperazin-1-yl]-2-furan-2-yl-[1,2,4]triazolo[1,5-a][1,3,5]triazin-7-ylamine 3,5-Dichloro-4-chloromethyl-pyridine (1.5 eq.) was added to a solution of 2-furan-2-yl-5-piperazin-1-yl-[1,2,4]triazolo[1,5-a][1,3,5]triazin-7-ylamine (0.14 mmol; see Example 1(a) above) and $Et_3N$ (0.3 mmol) in 3 mL of $CH_3CN$. The resulting reaction mixture was stirred at room temp for 18 hours. It was then concentrated and purified by preparative HPLC using a mixture of aqueous $CH_3CN$ that has been buffered with 0.1% TFA. $^1H$-NMR (DMSO-$d_6$) δ 8.9 (s, 2H), 7.60 (d, J=1.0 Hz, 1H), 7.28 (br s, 2H), 7.22 (d, J=3.6 Hz, 1H), 6.68 (dd, J=3.6 Hz, 1.0 Hz, 1H), 3.8 (br s, 2H), 2.2-3.2 (m, 8H). MS: m/z: 447 [M+H]$^+$.

EXAMPLE 5

[4-(7-Amino-2-furan-2-yl-[1,2,4]triazolo[1,5-a][1,3,5]triazin-5-yl)-piperazin-1-yl]-(3,5-dichloro-pyridin-4-yl)-methanone 2-Furan-2-yl-5-methanesulfonyl-[1,2,4]triazolo[1,5-a][1,3,5]triazin-7-ylamine (0.15 mmol; see Example 1(a) above) was suspended in 4 mL of $CH_3CN$ along with 3 eq. of (3,5-Dichloro-pyridin-4-yl)-piperazin-1-yl-methanone. The reaction mixture was stirred under reflux for 3 hours. It was then cooled to room temperature and concentrated under reduced pressure. The resulting crude product was purified by preparative HPLC using a mixture of aqueous $CH_3CN$ that has been buffered with 0.1% TFA. $^1H$ NMR (DMSO-$d_6$) δ 8.9 (s, 2H), 7.60 (d, J=1.0 Hz, 1H), 7.28 (br s, 2H), 7.22 (d, J=3.6 Hz, 1H), 6.68 (dd, J=3.6 Hz, 1.0 Hz, 1H), 2.2-3.2 (m, 8H). MS: m/z: 461 [M+H]$^+$.

EXAMPLE 6

$N^5$-[1-(2,6-Dichloro-benzyl)-pyrrolidin-2-ylmethyl]-2-furan-2-yl-[1,2,4]triazolo[1,5-a][1,3,5]triazine-5,7-diamine Synthesis of the title compound is described in parts (a)-(c) below.

(a) 2-[(7-Amino-2-furan-2-yl-[1,2,4]triazolo[1,3,5]triazin-5-ylamino)-methyl]-pyrrolidine-1-carboxylic acid tert-butyl ester 2-Furan-2-yl-5-methanesulfonyl-[1,2,4]triazolo[1,5-a][1,3,5]triazin-7-ylamine (2.5 mmol; see Example 1(a)) was suspended in 20 mL of $CH_3CN$ along with 5 mmol of (R)-2-aminomethyl-1-Boc-pyrrolidine (Astatech, Monmouth Junction, N.J.). The reaction mixture was stirred under reflux for 2 hours. It was then cooled to room temperature and concentrated under reduced pressure. The resulting residue was diluted with $CH_2Cl_2$ and washed with dilute 1% citric acid, brine, dried with $Na_2SO_4$ and concentrated under reduced pressure. Purification by chromatography (98% $CH_2Cl_2$, 2% MeOH) afforded 880 mg of 2-[(7-amino-2-furan-2-yl-[1,2,4]triazolo[1,5-a][1,3,5]triazin-5-ylamino)-methyl]-pyrrolidine-1-carboxylic acid tert-butyl ester.

(b) 2-Furan-2-yl-$N^5$-pyrrolidin-2-ylmethyl-[1,2,4]-triazolo[1,5-a][1,3,5]triazine-5,7-diamine Deprotection of 2-[(7-amino-2-furan-2-yl-[1,2,4]triazolo[1,5-a][1,3,5]triazin-5-ylamino)-methyl]-pyrrolidine-1-carboxylic acid tert-butyl ester was conducted by dissolving this Boc-protected compound in 6 mL of 25% TFA in $CH_2Cl_2$ and allowed to stand at room temperature for 2 hours. The reaction mixture was concentrated under reduced pressure to afford the TFA salt of 2-furan-2-yl-$N^5$-pyrrolidin-2-ylmethyl-[1,2,4]-triazolo[1,5-a][1,3,5]triazine-5,7-diamine. Analytically pure sample of this TFA salt was obtained by purification using preparative HPLC using a mixture of aqueous $CH_3CN$ buffered with 0.1% TFA.

In order to carry out reductive amination as described in subpart (c) below, the TFA salt was dissolved in 5 mL of water containing 1 molar equivalent of NaOH. The resulting solution was concentrated to afford 2-furan-2-yl-$N^5$-pyrrolidin-2-ylmethyl-[1,2,4]-triazolo[1,5-a][1,3,5]triazine-5,7-diamine as a mixture of the free amine and sodium trifluoroacetate. This material was used in subpart (c) below without further purification.

(c) N⁵-[1-(2,6-Dichloro-benzyl)-pyrrolidin-2-ylmethyl]-2-furan-2-yl-[1,2,4]triazolo[1,5-a][1,3,5]triazine-5,7-diamine 2-Furan-2-yl-N⁵-pyrrolidin-2-ylmethyl-[1,2,4]-triazolo[1,5-a][1,3,5]triazine-5,7-diamine (0.15 mmol) was dissolved in 4 mL of CH₂Cl₂ along with 2 eq. of 2,6-dichlorobenzaldehyde and 25 mL of glacial acetic acid. The reaction mixture was stirred at room temperature for 30 minutes and sodium triacetoxyborohydride (4 eq.) was added in a single portion. The resulting reaction mixture was then stirred at room temperature for 18 hours. It was then concentrated under a stream of N₂ and purified by preparative HPLC using a mixture of aqueous CH₃CN that has been buffered with 0.1% TFA. ¹H NMR (DMSO-d₆) δ 7.60 (d, J=1.0 Hz, 1H), 7.28 (br s, 2H), 7.22 (d, J=3.6 Hz, 1H), 6.95-7.0 (m, 3H), 6.68 (dd, J=3.6 Hz, 1.0 Hz, 1H), 2.2-3.2 (m, 8H). MS: m/z: 460[M+H]⁺.

EXAMPLE 7

N⁵-[1-(3,5-Dimethyl-isoxazol-4-ylmethyl)-pyrrolidin-2-ylmethyl]-2-furan-2-yl-[1,2,4]triazolo[1,5-a][1,3,5]triazine-5,7-diamine Methanesulfonic acid 5-methyl-isoxazol-3-ylmethyl ester (48 mg, 0.25 mmol; see Example 2(a) above) was added to a solution of 2-furan-2-yl-N⁵-pyrrolidin-2-ylmethyl-[1,2,4]-triazolo[1,5-a][1,3,5]triazine-5,7-diamine (0.24 mmol; see Example 6(a) and (b) above) and Et₃N (0.30 mmol) in 2 mL of CH₃CN. The resulting reaction mixture was stirred at room temperature for 18 hours. It was then concentrated and purified by preparative HPLC using a mixture of aqueous CH₃CN that has been buffered with 0.1% TFA. ¹H NMR (DMSO-d₆) δ 7.60 (d, J=1.0 Hz, 1H), 7.28 (br s, 2H), 7.22 (d, J=3.6 Hz, 1H), 6.68 (dd, J=3.6 Hz, 1.0 Hz, 1H), 3.8 (br s, 2H), 2.2-3.2 (m, 8H), 1.6 (br s, 6H). MS: m/z: 410 [M+H]⁺.

EXAMPLE 8

5-[4-(2-Chloro-benzyl)-[1,4]diazepan-1-yl]-2-furan-2-yl-[1,2,4]triazolo[1,5-a][1,3,5]triazin-7-ylamine Synthesis of the title compound is described in parts (a) and (b) below.

(a) 5-[1,4]Diazepan-1-yl-2-furan-2-yl-[1,2,4]triazolo[1,5-a][1,3,5]triazin-7-ylamine 2-Furan-2-yl-5-methanesulfnyl-[1,2,4]triazolo[1,5-a][1,3,5]triazin-7-ylamine (18 mmol; see Example 1(a) above) was suspended in 50 mL of CH₃CN along with 5 eq. of homopiperazine. The reaction mixture was stirred under reflux for 2 hours. It was then cooled to room temperature and concentrated under reduced pressure. The residue was taken up in CH₂Cl₂ and washed with H₂O, brine, dried with Na₂SO₄, and concentrated under reduced pressure. The resulting crude product was purified by chromatography (95% CH₂Cl₂, 4% MeOH, 1% Et₃N) to afford 5-[1,4]diazepan-1-yl-2-furan-2-yl-[1,2,4]triazolo[1,5-a][1,3,5]triazin-7-ylamine.

(b) 5-[4-(2-Chloro-benzyl)-[1,4]diazepan-1-yl]-2-furan-2-yl-[1,2,4]triazolo[1,5-a][1,3,5]triazin-7-ylamine 5-[1,4]Diazepan-1-yl-2-furan-2-yl-[1,2,4]triazolo[1,5-a][1,3,5]triazin-7-ylamine (0.15 mmol) was dissolved in 4 mL of CH₂Cl₂ along with 2 eq. of 2-chloro-benzaldehyde and 25 mL of glacial acetic acid. The reaction mixture was stirred at room temperature for 30 minutes and sodium triacetoxyborohydride (4 eq.) was added in a single portion. The resulting reaction mixture was then stirred at room temperature for 18 hours. It was then concentrated under a stream of N₂ and purified by preparative HPLC using a mixture of aqueous CH₃CN that has been buffered with 0.1% TFA. ¹H NMR (PMSO-d₆) δ 7.60 (d, J=1.0 Hz, 1H), 7.28 (br s, 2H), 7.22 (d, J=3.6 Hz, 1H), 6.9-7.2 (m, 4H), 6.68 (dd, J=3.6 Hz, 1.0 Hz, 1H), 3.8 (br s, 2H), 2.2-3.2 (m, 10 H). MS: m/z: 426 [M+H]⁺.

EXAMPLE 9

2-Furan-2-yl-5-(4-pyridin-2-ylmethyl-[1,4]diazepan-1-yl)-[1,2,4]triazolo[1,5-a][1,3,5]triazin-7-ylamine 2-Chloromethyl-pyridine (1.5 eq.) was directly added to a solution of 5-[1,4]diazepan-1-yl-2-furan-2-yl-[1,2,4]triazolo[1,5-a][1,3,5]triazin-7-ylamine (0.14 mmol; see Example 8(a) above) and Et₃N (0.3 mmol) in 3 mL of CH₃CN. The resulting reaction mixture was stirred at room temp for 18 hours. It was then concentrated and purified by preparative HPLC using a mixture of aqueous CH₃CN that has been buffered with 0.1% TFA. ¹H NMR (DMMSO-d₆) δ 7.60 (d, J=1.0 Hz, 1H), 7.28 (br s, 2H), 7.22 (d, J=3.6 Hz, 1H), 6.9-7.1 (m, 4H), 6.68 (dd, J=3.6 Hz, 1.0 Hz, 1H); 3.8 (br s, 2H), 2.2-3.2 (m, 10 H). MS: m/z: 392 [M+H]⁺.

EXAMPLE 10

5-[4-(3,5-Dimethyl-isoxazol-4-ylmethyl)-piperazin-1-yl]-2-(3-fluoro-phenyl)-[1,2,4]triazolo[1,5-a][1,3,5]triazin-7-ylamine Synthesis of the title compound is described in parts (a) and (b) below.

(a) 2-(3-Fluoro-phenyl)-5-piperazin-1-yl-[1,2,4]triazolo[1,5-a][1,3,5]triazin-7-ylamine 18 mmol of 2-(3-fluoro-phenyl)-5-methanesulfonyl-[1,2,4]triazolo[1,5-a][1,3,5]triazin-7-ylamine (prepared as described Caulkett et al., *J. Chem. Soc. Perkin Trans I.* 801-808 (1995)) was suspended in 50 mL of CH₃CN along with 5 eq. of piperazine. The reaction mixture was stirred under reflux for 2 hours. It was then cooled to room temperature and concentrated under reduced pressure. The residue was taken up in CH₂Cl₂ and washed with H₂O, brine, dried with Na₂SO₄, and concentrated under reduced pressure. The resulting crude product was purified by chromatography (95% CH₂Cl₂, 4% MeOH, 1% Et₃N) to afford 2-(3-fluoro-phenyl)-5-piperazin-1-yl-[1,2,4]triazolo[1,5-a][1,3,5]triazin-7-ylamine.

(b) 5-[4-(3,5-Dimethyl-isoxazol-4-ylmethyl)-piperazin-1-yl]-2-(3-fluoro-phenyl)-[1,2,4]triazolo[1,5-a][1,3,5]triazin-7-ylamine 2-(3Fluoro-phenyl)-5-piperazin-1-yl-[1,2,4]triazolo[1,5-a][1,3,5]triazin-7-ylamine (0.15 mmol) was dissolved in 4 mL of $CH_2Cl_2$ along with 2 eq. of 3,5-dimethyl-isoxazole-4-carbaldehyde and 25 mL of glacial acetic acid. The reaction mixture was stirred at room temperature for 30 minutes and sodium triacetoxyborohydride (4 eq.) was added in a single portion. The resulting reaction mixture was then stirred at room temperature for 18 hours. It was then concentrated under a stream of $N_2$ and purified by preparative HPLC using a mixture of aqueous $CH_3CN$ that has been buffered with 0.1% TFA. $^1H$ NMR (DMSO-$d_6$) δ 6.9-7.25 (m, 3 H), 3.8 (br s, 2H), 2.2-3.2 (m, 8H), 1.6 (br s, 6H). MS: m/z: 424 [M+H]$^+$.

EXAMPLE 11

2-(3-Fluoro-phenyl)-5-[4-(5-methyl-isoxazol-4-ylmethyl)-piperazin-1-yl]-[1,2,4]triazolo[1,5-a][1,3,5]triazin-7-ylamine 4-Chloromethyl-5-methyl-isoxazole (1.5 eq.) was directly added to a solution of 2-(3-fluoro-phenyl)-5-piperazin-1-yl-[1,2,4]triazolo[1,5-a][1,3,5]triazin-7-ylamine (0.14 mmol; see Example 10(a) above) and $Et_3N$ (0.3 mmol) in 3 mL of $CH_3CN$. The resulting reaction mixture was stirred at room temp for 18 hours. It was then concentrated and purified by preparative HPLC using a mixture of aqueous $CH_3CN$ that has been buffered with 0.1% TFA.
$^1H$ NMR (DMSO-$d_6$) δ 6.9-7.25 (m, 3 H), 6.6 (s, 1H), 3.8 (br s, 2H), 2.2-3.2 (m, 8H), 1.6 (br s, 3 H). MS: m/z: 410 [M+H]$^+$.

EXAMPLE 12

2-[4-(3,5-Dimethyl-isoxazol-4-ylmethyl)-piperazin-1-yl]-7-furan-2-yl-pyrazolo[1,5-a][1,3,5]triazin-4-ylamine Synthesis of the title compound is described in parts (a) and (b) below.

(a) 7-Furan-2-yl-2-piperazin-1-yl-pyrazolo[1,5-a][1,3,5]triazin-4-ylamine 18 mmol of 7-furan-2-yl-2-methanesulfonyl-pyrazolo[1,5-a][1,3,5]triazin-4-ylamine (Maybridge plc, Trevillett, Tintagel, Cornwall, England) was suspended in 50 mL of $CH_3CN$ along with 5 eq. of piperazine. The reaction mixture was stirred under reflux for 2 hours. It was then cooled to room temperature and concentrated under reduced pressure. The residue was taken up in $CH_2Cl_2$ and washed with $H_2O$, brine, dried with $Na_2SO_4$, and concentrated under reduced pressure. The resulting crude product was purified by chromatography (95% $CH_2Cl_2$, 4% MeOH, 1% $Et_3N$) to afford 7-furan-2-yl-2-piperazin-1-yl-pyrazolo[1,5-a][1,3,5]triazin-4-ylamine.

(b) 2-[4-(3,5-Dimethyl-isoxazol-4-ylmethyl)-piperazin-1-yl]-7-furan-2-yl-pyrazolo[1,5-a][1,3,5]triazin-4-ylamine 4-Chloromethyl-3,5-dimethyl-isoxazole (1.5 eq.) was directly added to a solution of 7-furan-2-yl-2-piperazin-1-yl-pyrazolo[1,5-a][1,3,5]triazin-4-ylamine (0.14 mmol) and $Et_3N$ (0.3 mmol) in 3 mL of $CH_3CN$. The resulting reaction mixture was stirred at room temp for 18 hours. It was then concentrated and purified by preparative HPLC using a mixture of aqueous $CH_3CN$ that has been buffered with 0.1% TFA. $^1H$ NMR (DMSO-$d_6$) δ 7.60 (d, J=1.0 Hz, 1 H), 7.28 (br s, 2H), 7.22 (d, J=3.6 Hz, 1H), 6.68 (dd, J=3.6 Hz, 1.0 Hz, 1 H), 6.2 (s, 1H) 3.8 (br s, 2H), 2.2-3.2 (m, 8H), 1.6 (br s, 6H). MS: m/z: 395 [M+H]$^+$.

EXAMPLE 13

2-[4-(2-Chloro-6-methyl-quinolin-3-ylmethyl)-piperazin-1-yl]-7-furan-2-yl-pyrazolo[1,5-a][1,3,5]triazin-4-ylamine 7-Furan-2-yl-2-piperazin-1-yl-pyrazolo[1,5-a][1,3,5]triazin-4-ylamine (0.15 mmol) was dissolved in 4 mL of $CH_2Cl_2$ along with 2 eq. of 2-chloro-6-methyl-quinoline-3-carbaldehyde and 25 mL of glacial acetic acid. The reaction mixture was stirred at room temperature for 30 minutes and sodium triacetoxyborohydride (4 eq.) was added in a single portion. The resulting reaction mixture was then stirred at room temperature for 18 hours. It was then concentrated under a stream of $N_2$ and purified by preparative HPLC using a mixture of aqueous $CH_3CN$ that has been buffered with 0.1% TFA. $^1H$ NMR (DMSO-$d_6$) δ 7.60 (d, J=1.0 Hz, 1H), 7.28 (br s, 2H), 7.22 (d, J=3.6 Hz, 1H), 7.4-8.0 (m, 4H), 6.68 (dd, J=3.6 Hz, 1.0 Hz, 1H), 6.2 (s, 1H) 3.8 (br s, 2H), 2.2-3.2 (m, 8H), 2.35 (br s, 3 H). MS: m/z: 476 [M+H]$^+$.

EXAMPLE 14

7-Furan-2-yl-2-[4-(5-methyl-isoxazol-3-ylmethyl)-[1,4]diazepan-1-yl]-pyrazolo[1,5-a][1,3,5]triazin-4-ylamine Synthesis of the title compound is described in parts (a) and (b) below.

(a) 2-[1,4]Diazepan-1-yl-7-furan-2-yl-pyrazolo[1,5-a][1,3,5]triazin-4-ylamine

7-Furan-2-yl-2-methanesulfonyl-pyrazolo[1,5-a][1,3,5]triazin-4-ylamine (18 mmol; see Example 12(a) above) was suspended in 50 mL of $CH_3CN$ along with 5 eq. of homopiperazine. The reaction mixture was stirred under reflux for 2 hours. It was then cooled to room temperature and concentrated under reduced pressure. The residue was taken up in $CH_2Cl_2$ and washed with $H_2O$, brine, dried with $Na_2SO_4$, and concentrated under reduced pressure. The resulting crude product was purified by chromatography (95% $CH_2Cl_2$, 4% MeOH, 1% $Et_3N$) to afford 2-[1,4]Diazepan-1-yl-7-furan-2-yl-pyrazolo[1,5-a][1,3,5]triazin-4-ylamine.

(b) 7-Furan-2-yl-2-[4-(5-methyl-isoxazol-3-ylmethyl)-[1,4]diazepan-1-yl]-pyrazolo[1,5-a][1,3,5]triazin-4-ylamine 3-Chloromethyl-5-methyl-isoxazole (1.5 eq.) was directly added to a solution of 2-[1,4]diazepan-1-yl-7-furan-2-yl-pyrazolo[1,5-a][1,3,5]triazin-4-ylamine (0.14 mmol) and Et$_3$N (0.3 mmol) in 3 mL of CH$_3$CN. The resulting reaction mixture was stirred at room temp for 18 hours. It was then concentrated and purified by preparative HPLC using a mixture of aqueous CH$_3$CN that has been buffered with 0.1% TFA. $^1$H NMR (DMSO-d$_6$) δ 7.90 (br s, 2 H), 7.80 (d, J=1.0 Hz, 1H), 7.05 (d, J=3.6 Hz, 1H), 6.68 (dd, J=3.6 Hz, 1.0 Hz, 1H), 6.30 (s, 1H), 3.65 (m, 2H), 3.20-2.75 (m, 10 H), 2.35 (s, 3H) ppm. MS: m/z: 395 [M+H]$^+$.

EXAMPLE 15

7-Furan-2-yl-N$^2$-[1-(5-methyl-isoxazol-3-ylmethyl)-pyrrolidin-2-ylmethyl]-pyrazolo[1,5-a][1,3,5]triazine-2,4-diamine Synthesis of the title compound is described in parts (a) and (b) below.

(a) 7-Furan-2-yl-N$^2$-pyrrolidin-2-ylmethyl-pyrazolo[1,5-a][1,3,5]triazine-2,4-diamine 7-Furan-2-yl-N$^2$-pyrrolidin-2-ylmethyl-pyrazolo[1,5-a][1,3,5]triazine-2,4-diamine was prepared in the same manner as described in Example 6(a) and (b) above, except that 7-furan-2-yl-2-methanesulfonyl-pyrazolo[1,5-a][1,3,5]triazin-4-ylamine was used as the starting material instead of 2-furan-2-yl-5-methanesulfonyl-[1,2,4]triazolo[1,5-a][1,3,5]triazin-7-ylamine.

(b) 7-Furan-2-yl-N$^2$-[1-(5-methyl-isoxazol-3-ylmethyl)-pyrrolidin-2-ylmethyl]-pyrazolo[1,5-a][1,3,5]triazine-2,4-diamine 3-Chloromethyl-5-methyl-isoxazole (1.5 eq.) was directly added to a solution of 7-furan-2-yl-N$^2$-pyrrolidin-2-ylmethyl-pyrazolo[1,5-a][1,3,5]triazine-2,4-diamine (0.14 mmol) and Et$_3$N (0.3 mmol) in 3 mL of CH$_3$CN. The resulting reaction mixture was stirred at room temp for 18 hours. It was then concentrated and purified by preparative HPLC using a mixture of aqueous CH$_3$CN that has been buffered with 0.1% TFA. $^1$H NMR (DMSO-d$_6$) δ 7.60 (d, J=1.0 Hz, 1H), 7.28 (br s, 2H), 7.22 (d, J=3.6 Hz, 1H), 6.68 (dd, J=3.6 Hz, 1.0 Hz, 1H), 6.3 (s, 1H) 3.8 (br s, 2H), 2.2-3.2 (m, 8H), 1.6 (br s, 3 H). MS: m/z: 395 [M+H]$^+$.

EXAMPLE 16

2-Furan-2-yl-N$^5$-methyl-N$^5$-{2-[methyl-(5-methyl-isoxazol-3-ylmethyl)-amino]-ethyl}-[1,2,4]triazolo[1,5-a][1,3,5]triazine-5,7-diamine Synthesis of the title compound is described in parts (a) and (b) below.

(a) 2-Furan-2-yl-N$^5$-methyl-N$^5$-(2-methylamino-ethyl)-[1,2,4]triazolo[1,5-a][1,3,5]triazine-5,7-diamine 2-Furan-2-yl-5-methanesulfonyl-[1,2,4]triazolo[1,5-a][1,3,5]triazin-7-ylamine (18 mmol; see Example 1(a) above) was suspended in 50 mL of CH$_3$CN along with 5 eq. of N,N'-dimethyl-ethane-1,2-diamine. The reaction mixture was stirred under reflux for 2 hours. It was then cooled to room temperature and concentrated under reduced pressure. The residue was taken up in CH$_2$Cl$_2$ and washed with H$_2$O, brine, dried with Na$_2$SO$_4$, and concentrated under reduced pressure. The resulting crude product was purified by chromatography (95% CH$_2$Cl$_2$, 4% MeOH, 1% Et$_3$N) to afford 2-furan-2-yl-N$^5$-methyl-N$^5$-(2-methylamino-ethyl)-[1,2,4]triazolo[1,5-a][1,3,5]triazine-5,7-diamine.

(b) 2-Furan-2-yl-N$^5$-methyl-N$^5$-{2-[methyl-(5-methyl-isoxazol-3-ylmethyl)-amino]-ethyl}-[1,2,4]triazolo[1,5-a][1,3,5]triazine-5,7-diamine 3-Chloromethyl-5-methyl-isoxazole (1.5 eq.) was directly added to a solution of 2-furan-2-yl-N$^5$-methyl-N$^5$-(2-methylamino-ethyl)-[1,2,4]triazolo[1,5-a][1,3,5]triazine-5,7-diamine (0.14 mmol) and Et$_3$N (0.3 mmol), in 3 mL of CH$_3$CN. The resulting reaction mixture was stirred at room temp for 18 hours. It was then concentrated and purified by preparative HPLC using a mixture of aqueous CH$_3$CN that has been buffered with 0.1% TFA. $^1$H NMR (DMSO-d$_6$) δ 7.90 (br s, 2H), 7.80 (d, J=1.0 Hz, 1H), 7.05 (d, J=3.6 Hz, 1 H), 6.68 (dd, J=3.6 Hz, 1.0 Hz, 1H), 6.30 (s, 1H), 3.65 (m, 2H), 3.20-2.75 (m, 4H), 2.5 (s, 3H), 2.35 (s, 3H), 2.3 (s, 3H) ppm. MS: m/z: 385 [M+H]$^+$.

EXAMPLE 17

2-Furan-2-yl-N$^5$-{2-[methyl-(5-methyl-isoxazol-3-ylmethyl)-amino]-ethyl}-[1,2,4]triazolo[1,5-a][1,3,5]triazine-5,7-diamine 2-Furan-2-yl-N$^5$-{2-[methyl-(5-methyl-isoxazol-3-ylmethyl)-amino]-ethyl}-[1,2,4]triazolo[1,5-a][1,3,5]triazine-5,7-diamine was prepared in the same manner as described in Example 6 above, except that N'-Boc-methyl-ethane-1,2-diamine was used as the starting material instead of (R)-2-aminomethyl-1-Boc-pyrrolidine. $^1$H NMR (DMSO-d$_6$) δ 7.90 (br s, 2H), 7.80 (d, J=1.0 Hz, 1H), 7.05 (d, J=3.6 Hz, 1H), 6.68 (dd, J=3.6 Hz, 1.0 Hz, 1H), 6.30 (s, 1H), 3.65 (m, 2H), 3.20-2.75 (m, 4H), 2.5 (s, 3H), 2.35 (s, 3 H) ppm. MS: m/z: 370 [M+H]$^+$.

EXAMPLE 18

2-Furan-2-yl-N$^5$-[1-(5-methyl-isoxazol-3-ylmethyl)-piperidin-3-ylmethyl]-[1,2,4]triazolo[1,5-a][1,3,5]triazine-5,7-diamine Synthesis of the title compound is described in parts (a) and (b) below.

(a) 2-Furan-2-yl-N$^5$-piperidin-3-ylmethyl-[1,2,4]triazolo[1,5-a][1,3,5]triazine-5,7-diamine 2-Furan-2-yl-N$^5$-piperidin-3-ylmethyl-[1,2,4]triazolo[1,5-a][1,3,5]triazine-5,7-diamine was prepared in the same manner as described in Example 6(a) and (b) above, except that 3-aminomethyl-1-Boc-piperidine was used as the starting material instead of 2-aminomethyl-1-Boc-pyrrolidine (both starting materials are commercially available from Astatech, Monmouth Junction, N.J.).

(b) 2-Furan-2-yl-$N^5$-[1-(5-methyl-isoxazol-3-ylm-ethyl)-piperidin-3-ylmethyl]-[1,2,4]triazolo[1,5-a][1,3,5]triazine-5,7-diamine 3-Chloromethyl-5-methyl-isoxazole (1.5 eq.) was directly added to a solution of 2-furan-2-yl-$N^5$-piperidin-3-ylmethyl-[1,2,4]triazolo[1,5-a][1,3,5]triazine-5,7-diamine (0.14 mmol) and Et$_3$N (0.3 mmol) in 3 mL of CH$_3$CN. The resulting reaction mixture was stirred at room temp for 18 hours. It was then concentrated and purified by preparative HPLC using a mixture of aqueous CH$_3$CN that has been buffered with 0.1% TFA. $^1$H NMR (DMSO-d$_6$) δ 7.90 (br s, 2H), 7.80 (d, J=1.0 Hz, 1H), 7.05 (d, J=3.6 Hz, 1H), 6.68 (dd, J=3.6 Hz, 1.0 Hz, 1H), 6.30 (s, 1H), 3.65 (m, 2H), 3.20-2.75 (m, 11 H), 2.35 (s, 3H) ppm. MS: m/z: 410 [M+H]$^+$.

EXAMPLE 19

2-Furan-2-yl-$N^5$-methyl-$N^5$-[1-(5-methyl-isoxazol-3-ylmethyl)-pyrrolidin-2-ylmethyl]-[1,2,4]triazolo[1,5-a][1,3,5]triazine-5,7-diamine Synthesis of the title compound is described in parts (a) and (b) below.

(a) (R)-2-Methylaminomethyl-1-Boc-pyrrolidine (R)-Boc-proline (4.8 g, 22.3 mmol) was suspended in 100 mL of THF. 1-Ethyl-3-(3-dimethylaminopropyl)carbodiimide (5.13 g, 1.2 eq) was then added to the solution, followed by 1-hydroxybenzotriazole (3.62 g, 1.2 eq) and N-methylmorpholine (3.7 mL, 1.5 eq). The reaction mixture was stirred at room temperature for 30 minutes and 35 mL of methylamine in THF (2.0 M, 3 eq) was added. The reaction mixture was stirred at room temperature for 18 hours. It was then concentrated and the residue was taken up in CH$_2$Cl$_2$ and washed with diluted NaHCO$_3$, water, dilute 1 N citric acid, brine, dried (with Na$_2$SO$_4$ and concentrated to yield 4.8 g of the crude carboxamide intermediate. This material was dissolved in 100 mL of anhydrous THF and cooled to 0° C. Borane THF (53 mL of the 1.0 M solution, 2.5 eq) was added and the reaction mixture was allowed to warm to room temperature and stirred at room temperature for 18 hours. It was then cooled to 0° C. and carefully quenched with 50 mL of methanol. The reaction mixture was concentrated under reduced pressure. The resulting residue was redissolved in 50 mL of methanol and 100 mL of ethyl acetate and concentrated under reduced pressure. This trituration and concentration under reduced pressure was repeated three more times to afford essentially quantitative yield of (R)-2-methylaminomethyl-1-Boc-pyrrolidine, which was then used without further purification.

(b) 2-Furan-2-yl-$N^5$-methyl-$N^5$-[1-(5-methyl-isoxazol-3-ylmethyl)-pyrrolidin-2-ylmethyl]-[1,2,4]triazolo[1,5-a][1,3,5]triazine-5,7-diamine 2-Furan-2-yl-$N^5$-methyl-$N^5$-[1-(5-methyl-isoxazol-3-ylmethyl)-pyrrolidin-2-ylmethyl]-[1,2,4]triazolo[1,5-a][1,3,5]triazine-5,7-diamine was prepared in the same manner as described in Example 18 above except that (R)-2-methylaminomethyl-1-Boc-pyrrolidine (see subpart (a) above) as used as the starting mattrial instead of 3-aminomethyl-1-Boc-piperidine. $^1$H NMR (DMSO-d$_6$) δ 7.90 (br s, 2H) 7.80 (d, J=1.0 Hz, 1H), 7.05 (d, J=3.6 Hz, 1 H), 6.68 (dd, J=3.6 Hz, 1.0 Hz, 1H), 6.30 (s, 1H), 3.65 (m, 2H), 3.20-2.75 (m, 11 H), 2.5 (s, 3H), 2.35 (s, 3H) ppm. MS: m/z: 410 [M+H]$^+$.

EXAMPLE 20

$N^5$-{2-[4-(2,4-Difluoro-phenyl)-piperazin-1-yl]-ethyl}-2-furan-2-yl-[1,2,4]triazolo[1,5-a][1,3,5]triazine-5,7-diamine Synthesis of the title compound is described in parts (a) and (b) below.

(a) $N^5$-(2,2-dimethoxy-ethyl)-2-furan-2-yl-[1,2,4]triazolo[1,5-a][1,3,5]triazine-5,7-diamine 500 mg of 2-Furan-2-yl-5-methanesulfonyl-[1,2,4]triazolo[1,5-a][1,3,5]triazin-7-ylamine (1.78 mmol; see Example 1(a) above) was suspended in 3 mL of DMSO and 15 mL of acetonitrile along with 3 eq of triethylamine. After addition of 1.2 eq. of aminoacetaldyde dimethyl acetal, the reaction mixture was stirred under reflux for 3 hours. It was then cooled to room temperature and concentrated under reduced pressure. The resulting residue was taken up in EtOAc and washed with dilute citric acid, brine, dried with Na$_2$SO$_4$ and concentrated to afford $N^5$-(2,2-dimethoxy-ethyl)-2-furan-2-yl-[1,2,4]triazolo[1,5-a][1,3,5]triazine-5,7-diamine.

(b) $N^5$-{2-[4-(2,4-Difluoro-phenyl)-piperazin-1-yl]-ethyl}-2-furan-2-yl-[1,2,4]triazolo[1,5-a][1,3,5]triazine-5,7-diamine The dimethyl acetal intermediate (40 mg, 0.13 mmol) from subpart (a) above was suspended in 2 mL of CH$_2$Cl$_2$ and 0.2 mL of 2:1 solution of TFA/H$_2$O was added. The resulting reaction mixture was stirred at room temperature for 4 hours. It was then neutralized with 0.25 mL of triethylamine. 1-(2,4-Difluoro-phenyl)-piperazine (40 mg, 1.5 eq., prepared by reacting piperazine with 1-bromo-2,4-difluorobenzene according to the procedure described in WO 01/92264 A1), was added, followed by 140 mg of Na(OAc)$_3$BH. The resulting reaction mixture was stirred at room temperature for 2 hours. It was then concentrated and then purified by preparative HPLC to afford $N^5$-{2-[4-(2,4-difluoro-phenyl)-piperazin-1-yl]-ethyl}-2-furan-2-yl-[1,2,4]triazolo[1,5-a][1,3,5]triazine-5,7-diamine. $^1$H NMR (DMSO-d$_6$) δ 7.90 (br s, 2H), 7.80 (d, J=1.0 Hz, 1H), 7.05 (d, J=3.6 Hz, 1H), 7.10-7.50 (m, 3 H), 6.68 (dd, J=3.6 Hz, 1.0 Hz, 1H) 3.20-2.75 (m, 12 H) ppm. MS: m/z: 442 [M+H]$^+$.

EXAMPLE 21

$N^5$-{2-[4-(2,4-Difluoro-phenyl)-piperazin-1-yl]-ethyl}-2-furan-2-yl-$N^5$-methyl-[1,2,4]triazolo[1,5-a][1,3,5]triazine-5,7-diamine The title compound was prepared in the same manner as described in Example 20 above, except that N-methylaminoacetaldehyde dimethyl acetal was used instead of aminoacetaldyde dimethyl acetal. $^1$H NMR (DMSO-d$_6$) δ 7.90 (for s, 2H), 7.80 (d, J=1.0 Hz, 1H), 7.05 (d, J=3.6 Hz, 1H), 7.10-7.50 (m, 3H), 6.68 (dd, J=3.6 Hz, 1.0 Hz, 1H), 3.20-2.75 (m, 12 H), 2.5 (s, 3H) ppm. MS: m/z: 456 [M+H]$^+$.

The compounds listed in the following table were prepared in an analogous manner as described in the methods and examples above. The mass spectroscopy data of these compounds are included in the table.

| Example | Compound Name | Mass Spec. (m/z) | Synthetic Method |
|---|---|---|---|
| Ex. 22 | $N^5$-(1-Benzyl-piperidin-4-yl)-2-furan-2-yl-[1,2,4]triazolo[1,5-a][1,3,5]triazine-5,7-diamine | 391 [M + H]+ | Ex. 5 |
| Ex. 23 | $N^5$-(1-Benzyl-pyrrolidin-3-yl)-2-furan-2-yl-[1,2,4,]triazolo[1,5-a][1,3,5]triazine-5,7-diamine | 377 [M + H]+ | Ex. 5 |
| Ex. 24 | 2-Furan-2-yl-$N^5$-[1-(5-methyl-isoxazol-3-ylmethyl)-pyrrolidin-3-yl]-[1,2,4]triazolo[1,5-a][1,3,5]triazine-5,7-diamine | 382 [M + H]+ | Ex. 15 |
| Ex. 25 | 2-Furan-2-yl-5-(4-pyridin-3-ylmethyl-piperazin-1-yl)-[1,2,4]triazolo[1,5-a][1,3,5]triazin-7-ylamine | 378 [M + H]+ | Ex. 1 |
| Ex. 26 | 2-Furan-2-yl-5-(4-pyridin-4-ylmethyl-piperazin-1-yl)-[1,2,4]triazolo[1,5-a][1,3,5]triazin-7-ylamine | 378 [M + H]+ | Ex. 1 |
| Ex. 27 | 2-Furan-2-yl-$N^5$-[1-(5-methyl-isoxazol-3-ylmethyl)-pyrrolidin-2-ylmethyl]-[1,2,4]triazolo[1,5-a][1,3,5]triazine-5,7-diamine | 396 [M + H]+ | Ex. 7 |
| Ex. 28 | 2-Furan-2-yl-$N^5$-{2-[(5-methyl-isoxazol-3-ylmethyl)-amino]-ethyl}-[1,2,4]triazolo[1,5-a][1,3,5]triazine-5,7-diamine | 355 [M + H]+ | Ex. 16 |
| Ex. 29 | 2-Furan-2-yl-5-[4-(1H-imidazol-2-ylmethyl)-piperazin-1-yl]-[1,2,4]triazolo[1,5-a][1,3,5]triazin-7-ylamine | 367 [M + H]+ | Ex. 1 |
| Ex. 30 | 2-Furan-2-yl-5-[4-(1-methyl-1H-imidazol-2-ylmethyl)-piperazin-1-yl]-[1,2,4]triazolo[1,5-a][1,3,5]triazin-7-ylamine | 381 [M + H]+ | Ex. 1 |
| Ex. 31 | 5-[4-(5-Chloro-thiophen-2-ylmethyl)-piperazin-1-yl]-2-furan-2-yl-[1,2,4]triazolo[1,5-a][1,3,5]triazin-7-ylamine | 418 [M + H]+ | Ex. 1 |
| Ex. 32 | 2-Furan-2-yl-5-[4-(1H-imidazol-4-ylmethyl)-piperazin-1-yl]-[1,2,4]triazolo[1,5-a][1,3,5]triazin-7-ylamine | 367 [M + H]+ | Ex. 1 |
| Ex. 33 | 2-Furan-2-yl-5-[4-(1H-pyrrol-2-ylmethyl)-piperazin-1-yl]-[1,2,4]triazolo[1,5-a][1,3,5]triazin-7-ylamine | 366 [M + H]+ | Ex. 1 |
| Ex. 34 | 2-Furan-2-yl-$N^5$-[1-(5-methyl-isoxazol-3-ylmethyl)-piperidin-4-ylmethyl]-[1,2,4]triazolo[1,5-a][1,3,5]triazine-5,7-diamine | 410 [M + H]+ | Ex. 18 |
| Ex. 35 | 2-Furan-2-yl-$N^5$-[1-(5-methyl-isoxazol-3-ylmethyl)-piperidin-3-yl]-[1,2,4]triazolo[1,5-a][1,3,5]triazine-5,7-diamine | 396 [M + H]+ | Ex. 18 |
| Ex. 36 | 2-Furan-2-yl-$N^5$-methyl-$N^5$-{2-[methyl-(5-methyl-isoxazol-3-ylmethyl)-amino]-cyclohexyl}-[1,2,4]triazolo[1,5-a][1,3,5]triazine-5,7-diamine | 438 [M + H]+ | Ex. 2 |
| Ex. 37 | 2-Furan-2-yl-$N^5$-{3-[(5-methyl-isoxazol-3-ylmethyl)-amino]-propyl}-[1,2,4]triazolo[1,5-a][1,3,5]triazine-5,7-diamine | 370 [M + H]+ | Ex. 2 |
| Ex. 38 | $N^5$-{2,2-Dimethyl-3-[(5-methyl-isoxazol-3-ylmethyl)-amino]-propyl}-2-furan-2-yl-[1,2,4]triazolo[1,5-a][1,3,5]triazine-5,7-diamine | 398 [M + H]+ | Ex. 2 |
| Ex. 39 | 2-Furan-2-yl-$N^5$-[1-(5-methyl-isoxazol-3-ylmethyl)-piperidin-4-yl]-[1,2,4]triazolo[1,5-a][1,3,5]triazine-5,7-diamine | 396 [M + H]+ | Ex. 18 |
| Ex. 40 | 2-Furan-2-yl-$N^5$-[1-(5-methyl-isoxazol-3-ylmethyl)-pyrrolidin-2-ylmethyl]-[1,2,4]triazolo[1,5-a][1,3,5]triazine-5,7-diamine | 396 [M + H]+ | Ex. 18 |
| Ex. 41 | 2-Furan-2-yl-5-(4-quinolin-4-ylmethyl-piperazin-1-yl)-[1,2,4]triazolo[1,5-a][1,3,5]triazin-7-ylamine | 428 [M + H]+ | Ex. 1 |
| Ex. 42 | 2-Furan-2-yl-5-[4-(5-methyl-3H-imidazol-4-ylmethyl)-piperazin-1-yl]-[1,2,4]triazolo[1,5-a][1,3,5]triazin-7-ylamine | 381 [M + H]+ | Ex. 1 |
| Ex. 43 | 2-Furan-2-yl-5-(4-furan-2-ylmethyl-piperazin-1-yl)-[1,2,4]triazolo[1,5-a][1,3,5]triazin-7-ylamine | 367 [M + H]+ | Ex. 1 |
| Ex. 44 | 2-Furan-2-yl-5-(4-quinolin-2-ylmethyl-piperazin-1-yl)-[1,2,4]triazolo[1,5-a][1,3,5]triazin-7-ylamine | 428 [M + H]+ | Ex. 1 |
| Ex. 45 | 2-Furan-2-yl-$N^5$-methyl-N5-[1-(5-methyl-isoxazol-3-ylmethyl)-pyrrolidin-2-ylmethyl]-[1,2,4]triazolo[1,5-a][1,3,5]triazine-5,7-diamine | 410 [M + H]+ | Ex. 19 |
| Ex. 46 | 2-Furan-2-yl-5-[4-(3-phenyl-propyl)-[1,4]diazepan-1-yl]-[1,2,4]triazolo[1,5-a][1,3,5]triazin-7-ylamine | 419 [M + H]+ | Ex. 8 |
| Ex. 47 | 5-[4-(2,6-Dichloro-benzyl)-[1,4]diazepan-1-yl]-2-furan-2-yl-[1,2,4]triazolo[1,5-a][1,3,5]triazin-7-ylamine | 460 [M + H]+ | Ex. 8 |
| Ex. 48 | 2-Furan-2-yl-5-[4-(5-methyl-isoxazol-3-ylmethyl)-[1,4]diazepan-1-yl]-[1,2,4]triazolo[1,5-a][1,3,5]triazin-7-ylamine | 396 [M + H]+ | Ex. 9 |
| Ex. 49 | 2-Furan-2-yl-5-(4-pyridin-3-ylmethyl-[1,4]diazepan-1-yl)-[1,2,4]triazolo[1,5-a][1,3,5]triazin-7-ylamine | 392 [M + H]+ | Ex. 8 |
| Ex. 50 | 2-Furan-2-yl-5-(4-pyridin-4-ylmethyl-[1,4]diazepan-1-yl)-[1,2,4]triazolo[1,5-a][1,3,5]triazin-7-ylamine | 392 [M + H]+ | Ex. 8 |
| Ex. 51 | 2-Furan-2-yl-5-(4-quinolin-4-ylmethyl-[1,4]diazepan-1-yl)-[1,2,4]triazolo[1,5-a][1,3,5]triazin-7-ylamine | 442 [M + H]+ | Ex. 8 |
| Ex. 52 | 2-Furan-2-yl-5-(4-quinolin-2-ylmethyl-[1,4]diazepan-1-yl)-[1,2,4]triazolo[1,5-a][1,3,5]triazin-7-ylamine | 442 [M + H]+ | Ex. 8 |
| Ex. 53 | 2-Furan-2-yl-5-(4-furan-2-ylmethyl-[1,4]diazepan-1-yl)-[1,2,4]triazolo[1,5-a][1,3,5]triazin-7-ylamine | 381 [M + H]+ | Ex. 8 |
| Ex. 54 | 2-[(7-Amino-2-furan-2-yl-[1,2,4]triazolo[1,5-a][1,3,5]triazin-5-ylamino)-methyl]-pyrrolidine-1-carboxylic acid tert-butyl ester | 401 [M + H]+ | Ex. 6 |
| Ex. 55 | 2-(3-Fluoro-phenyl)-5-[4-(5-methyl-isoxazol-3-ylmethyl)-piperazin-1-yl]-[1,2,4]triazolo[1,5-a][1,3,5]triazin-7-ylamine | 410 [M + H]+ | Ex. 10 |
| Ex. 56 | 2-Furan-2-yl-5-[4-(5-methyl-isoxazol-4-ylmethyl)-piperazin-1-yl]-[1,2,4]triazolo[1,5-a][1,3,5]triazin-7-ylamine | 382 [M + H]+ | Ex. 3 |
| Ex. 57 | 2-Furan-2-yl-5-[4-(5-methyl-isoxazol-4-ylmethyl)-piperazin-1-yl]-[1,2,4]triazolo[1,5-a][1,3,5]triazin-7-ylamine | 382 [M + H]+ | Ex. 3 |
| Ex. 58 | 2-(3-Fluoro-phenyl)-5-[4-(5-methyl-isoxazol-4-ylmethyl)-[1,4]diazepan-1-yl]-[1,2,4]triazolo[1,5-a][1,3,5]triazin-7-ylamine | 424 [M + H]+ | Ex. 11 |

-continued

| Example | Compound Name | Mass Spec. (m/z) | Synthetic Method |
|---|---|---|---|
| Ex. 59 | 2-(3-Fluoro-phenyl)-5-[4-(5-methyl-isoxazol-3-ylmethyl)-[1,4]diazepan-1-yl]-[1,2,4]triazolo[1,5-a][1,3,5]triazin-7-ylamine | 424 [M + H]+ | Ex. 11 |
| Ex. 60 | 2-(3-Fluoro-phenyl)-N$^5$-[1-(5-methyl-isoxazol-3-ylmethyl)-pyrrolidin-2-ylmethyl]-[1,2,4]triazolo[1,5-a][1,3,5]triazine-5,7-diamine | 424 [M + H]+ | Ex. 11 |
| Ex. 61 | 5-[4-(5-Chloro-furan-2-ylmethyl)-piperazin-1-yl]-2-furan-2-yl-[1,2,4]triazolo[1,5-a][1,3,5]triazin-7-ylamine | 402 [M + H]+ | Ex. 1 |
| Ex. 62 | 5-[4-(6-Bromo-pyridin-2-ylmethyl)-piperazin-1-yl]-2-furan-2-yl-[1,2,4]triazolo[1,5-a][1,3,5]triazin-7-ylamine | 457 [M + H]+ | Ex. 1 |
| Ex. 63 | 5-[4-(2-Chloro-8-methyl-quinolin-3-ylmethyl)-piperazin-1-yl]-2-furan-2-yl-[1,2,4]triazolo[1,5-a][1,3,5]triazin-7-ylamine | 477 [M + H]+ | Ex. 1 |
| Ex. 64 | 5-[4-(2-Chloro-6-methyl-quinolin-3-ylmethyl)-piperazin-1-yl]-2-furan-2-yl-[1,2,4]triazolo[1,5-a][1,3,5]triazin-7-ylamine | 477 [M + H]+ | Ex. 1 |
| Ex. 65 | 2-Furan-2-yl-5-(4-quinolin-3-ylmethyl-piperazin-1-yl)-[1,2,4]triazolo[1,5-a][1,3,5]triazin-7-ylamine | 428 [M + H]+ | Ex. 1 |
| Ex. 66 | 2-Furan-2-yl-5-[4-(5-methyl-furan-2-ylmethyl)-piperazin-1-yl]-[1,2,4]triazolo[1,5-a][1,3,5]triazin-7-ylamine | 381 [M + H]+ | Ex. 1 |
| Ex. 67 | {5-[4-(7-Amino-2-furan-2-yl-[1,2,4]triazolo[1,5-a][1,3,5]triazin-5-yl)-piperazin-1-ylmethyl]-furan-2-yl}-methanol | 397 [M + H]+ | Ex. 1 |
| Ex. 68 | 5-[4-(3,5-Dimethyl-isoxazol-4-ylmethyl)-[1,4]diazepan-1-yl]-2-furan-2-yl-[1,2,4]triazolo[1,5-a][1,3,5]triazin-7-ylamine | 410 [M + H]+ | Ex. 9 |
| Ex. 69 | 2-Furan-2-yl-5-(4-quinolin-3-ylmethyl)-[1,4]diazepan-1-yl)-[1,2,4]triazolo[1,5-a][1,3,5]triazin-7-ylamine | 442 [M + H]+ | Ex. 8 |
| Ex. 70 | 2-Furan-2-yl-5-[4-(2-methyl-furan-3-ylmethyl)-[1,4]diazepan-1-yl]-[1,2,4]triazolo[1,5-a][1,3,5]triazin-7-ylamine | 395 [M + H]+ | Ex. 8 |
| Ex. 71 | 2-Furan-2-yl-5-[4-(2-methyl-furan-3-ylmethyl)-piperazin-1-yl]-[1,2,4]triazolo[1,5-a][1,3,5]triazin-7-ylamine | 381 [M + H]+ | Ex. 1 |
| Ex. 72 | N$^5$-[1-(3-Chloro-benzyl)-pyrrolidin-2-ylmethyl]-2-furan-2-yl-[1,2,4]triazolo[1,5-a][1,3,5]triazine-5,7-diamine | 426 [M + H]+ | Ex. 6 |
| Ex. 73 | 2-Furan-2-yl-5-[4-(3-methyl-thiophen-2-ylmethyl)-[1,4]diazepan-1-yl]-[1,2,4]triazolo[1,5-a][1,3,5]triazin-7-ylamine | 411 [M + H]+ | Ex. 8 |
| Ex. 74 | 2-Furan-2-yl-5-[4-(1-methyl-1H-imidazol-2-ylmethyl)-[1,4]diazepan-1-yl]-[1,2,4]triazolo[1,5-a][1,3,5]triazin-7-ylamine | 395 [M + H]+ | Ex. 8 |
| Ex. 75 | N$^5$-[1-(4-Chloro-benzyl)-pyrrolidin-2-ylmethyl]-2-furan-2-yl-[1,2,4]triazolo[1,5-a][1,3,5]triazine-5,7-diamine | 426 [M + H]+ | Ex. 6 |
| Ex. 76 | 5-[4-(6-Bromo-pyridin-2-ylmethyl)-[1,4]diazepan-1-yl]-2-furan-2-yl-[1,2,4]triazolo[1,5-a][1,3,5]triazin-7-ylamine | 471 [M + H]+ | Ex. 8 |
| Ex. 77 | 2-Furan-2-yl-N$^5$-(1-pyridin-3-ylmethyl-pyrrolidin-2-ylmethyl)-[1,2,4]triazolo[1,5-a][1,3,5]triazine-5,7-diamine | 392 [M + H]+ | Ex. 6 |
| Ex. 78 | 5-[4-(5-Chloro-furan-2-ylmethyl)-[1,4]diazepan-1-yl]-2-furan-2-yl-[1,2,4]triazolo[1,5-a][1,3,5]triazin-7-ylamine | 416 [M + H]+ | Ex. 8 |
| Ex. 79 | 2-Furan-2-yl-N$^5$-(1-pyridin-4-ylmethyl-pyrrolidin-2-ylmethyl)-[1,2,4]triazolo[1,5-a][1,3,5]triazine-5,7-diamine | 392 [M + H]+ | Ex. 6 |
| Ex. 80 | 5-[4-(3-Chloro-2,6-difluoro-benzyl)-[1,4]diazepan-1-yl]-2-furan-2-yl-[1,2,4]triazolo[1,5-a][1,3,5]triazin-7-ylamine | 462 [M + H]+ | Ex. 8 |
| Ex. 81 | 5-[4-(6-Chloro-2-fluoro-3-methyl-benzyl)-[1,4]diazepan-1-yl]-2-furan-2-yl[1,2,4]triazolo[1,5-a][1,3,5]triazin-7-ylamine | 458 [M + H]+ | Ex. 8 |
| Ex. 82 | 5-[4-(2-Chloro-6-fluoro-3-methyl-benzyl)-[1,4]diazepan-1-yl]-2-furan-2-yl-[1,2,4]triazolo[1,5-a][1,3,5]triazin-7-ylamine | 458 [M + H]+ | Ex. 8 |
| Ex. 83 | 5-[4-(2-Chloro-8-methyl-quinolin-3-ylmethyl)-[1,4]diazepan-1-yl]-2-furan-2-yl-[1,2,4]triazolo[1,5-a][1,3,5]triazin-7-ylamine | 491 [M + H]+ | Ex. 8 |
| Ex. 84 | 5-[4-(2-Chloro-6-methyl-quinolin-3-ylmethyl)-[1,4]diazepan-1-yl]-2-furan-2-yl[1,2,4]triazolo[1,5-a][1,3,5]triazin-7-ylamine | 491 [M + H]+ | Ex. 8 |
| Ex. 85 | N$^5$-[1-(2-Bromo-benzyl)-pyrrolidin-2-ylmethyl]-2-furan-2-yl-[1,2,4]triazolo[1,5-a][1,3,5]triazine-5,7-diamine | 470 [M + H]+ | Ex. 6 |
| Ex. 86 | N$^5$-[1-(2-Fluoro-benzyl)-pyrrolidin-2-ylmethyl]-2-furan-2-yl-[1,2,4]triazolo[1,5-a][1,3,5]triazine-5,7-diamine | 409 [M + H]+ | Ex. 6 |
| Ex. 87 | N$^5$-[1-(2-Chloro-benzyl)-pyrrolidin-2-ylmethyl]-2-furan-2-yl-[1,2,4]triazolo[1,5-a][1,3,5]triazine-5,7-diamine | 426 [M + H]+ | Ex. 6 |
| Ex. 88 | 2-Furan-2-yl-N$^5$-(1-pyridin-2-ylmethyl-pyrrolidin-2-ylmethyl)-[1,2,4]triazolo[1,5-a][1,3,5]triazine-5,7-diamine | 392 [M + H]+ | Ex. 6 |
| Ex. 89 | 2-Furan-2-yl-N$^5$-(1-quinolin-2-ylmethyl-pyrrolidin-2-ylmethyl)-[1,2,4]triazolo[1,5-a][1,3,5]triazine-5,7-diamine | 442 [M + H]+ | Ex. 6 |
| Ex. 90 | 2-Furan-2-yl-N$^5$-(1-furan-2-ylmethyl-pyrrolidin-2-ylmethyl)-[1,2,4]triazolo[1,5-a][1,3,5]triazine-5,7-diamine | 381 [M + H]+ | Ex. 6 |
| Ex. 91 | 5-[4-(2-Chloro-quinolin-3-ylmethyl)-piperazin-1-yl]-2-furan-2-yl-[1,2,4]triazolo[1,5-a][1,3,5]triazin-7-ylamine | 463 [M + H]+ | Ex. 1 |
| Ex. 92 | 5-[4-(5-Bromo-furan-2-ylmethyl)-piperazin-1-yl]-2-furan-2-yl-[1,2,4]triazolo[1,5-a][1,3,5]triazin-7-ylamine | 446 [M + H]+ | Ex. 1 |
| Ex. 93 | 2-Furan-2-yl-5-(4-thiophen-3-ylmethyl-piperazin-1-yl)-[1,2,4]triazolo[1,5-a][1,3,5]triazin-7-ylamine | 383 [M + H]+ | Ex. 1 |
| Ex. 94 | 2-Furan-2-yl-5-[4-(2-methyl-benzyl)-[1,4]diazepan-1-yl]-[1,2,4]triazolo[1,5-a][1,3,5]triazin-7-ylamine | 405 [M + H]+ | Ex. 8 |
| Ex. 95 | 2-Furan-2-yl-5-[4-(3-methyl-benzyl)-[1,4]diazepan-1-yl]-[1,2,4]triazolo[1,5-a][1,3,5]triazin-7-ylamine | 405 [M + H]+ | Ex. 8 |

-continued

| Example | Compound Name | Mass Spec. (m/z) | Synthetic Method |
|---|---|---|---|
| Ex. 96 | 2-Furan-2-yl-5-[4-(4-methyl-benzyl)-[1,4]diazepan-1-yl]-[1,2,4]triazolo[1,5-a][1,3,5]triazin-7-ylamine | 405 [M + H]+ | Ex. 8 |
| Ex. 97 | 5-[4-(3-Chloro-benzyl)-[1,4]diazepan-1-yl]-2-furan-yl [1,2,4]triazolo[1,5-a][1,3,5]triazin-7-ylamine | 426 [M + H]+ | Ex. 8 |
| Ex. 98 | 5-[4-(4-Chloro-benzyl)-[1,4]diazepan-1-yl]-2-furan-2-yl-[1,2,4]triazolo[1,5-a][1,3,5]triazin-7-ylamine | 426 [M + H]+ | Ex. 8 |
| Ex. 99 | 5-[4-(2-Bromo-benzyl)-[1,4]diazepan-1-yl]-2-furan-2-yl-[1,2,4]triazolo[1,5-a][1,3,5]triazin-7-ylamine | 470 [M + H]+ | Ex. 8 |
| Ex. 100 | 5-[4-(3-Bromo-benzyl)-[1,4]diazepan-1-yl]-2-furan-2-yl-[1,2,4]triazolo[1,5-a][1,3,5]triazin-7-ylamine | 470 [M + H]+ | Ex. 8 |
| Ex. 101 | 5-[4-(4-Bromo-benzyl)-[1,4]diazepan-1-yl]-2-furan-2-yl-[1,2,4]triazolo[1,5-a][1,3,5]triazin-7-ylamine | 470 [M + H]+ | Ex. 8 |
| Ex. 102 | 5-[4-(2-Fluoro-benzyl)-[1,4]diazepan-1-yl]-2-furan-2-yl-[1,2,4]triazolo[1,5-a][1,3,5]triazin-7-ylamine | 409 [M + H]+ | Ex. 8 |
| Ex. 103 | $N^5$-[1-(6-Chloro-2-fluoro-3-methyl-benzyl)-pyrrolidin-2-ylmethyl]-2-furan-2-yl-[1,2,4]triazolo[1,5-a][1,3,5]triazine-5,7-diamine | 458 [M + H]+ | Ex. 6 |
| Ex. 104 | $N^5$-[1-(3-Chloro-2,6-difluoro-benzyl)-pyrrolidin-2-ylmethyl]-2-furan-2-yl-[1,2,4]triazolo[1,5-a][1,3,5]triazine-5,7-diamine | 462 [M + H]+ | Ex. 6 |
| Ex. 105 | $N^5$-[1-(2-Chloro-3,6-difluoro-benzyl)-pyrrolidin-2-ylmethyl]-2-furan-2-yl-[1,2,4]triazolo[1,5-a][1,3,5]triazine-5,7-diamine | 462 [M + H]+ | Ex. 6 |
| Ex. 106 | 2-Furan-2-yl-5-[4-(2-methylsulfanyl-thiophen-3-ylmethyl)-piperazin-1-yl]-[1,2,4]triazolo[1,5-a][1,3,5]triazin-7-ylamine | 429 [M + H]+ | Ex. 1 |
| Ex. 107 | 5-[4-(5-Chloro-2-phenyl-1H-imidazol-4-ylmethyl)-piperazin-1-yl]-2-furan-2-yl-[1,2,4]triazolo[1,5-a][1,3,5]triazin-7-ylamine | 478 [M + H]+ | Ex. 1 |
| Ex. 108 | 5-[4-(5-Chloro-1-methyl-3-trifluoromethyl-1H-pyrazol-4-ylmethyl)-piperazin-1-yl]-2-furan-2-yl-[1,2,4]triazolo[1,5-a][1,3,5]triazin-7-ylamine | 484 [M + H]+ | Ex. 1 |
| Ex. 109 | 5-[4-(4-Chloro-1-methyl-1H-pyrazol-3-ylmethyl)-piperazin-1-yl]-2-furan-2-yl-[1,2,4]triazolo[1,5-a][1,3,5]triazin-7-ylamine | 416 [M + H]+ | Ex. 1 |
| Ex. 110 | 5-[4-(4-Bromo-1-methyl-1H-pyrazol-3-ylmethyl)-piperazin-1-yl]-2-furan-2-yl-[1,2,4]triazolo[1,5-a][1,3,5]triazin-7-ylamine | 460 [M + H]+ | Ex. 1 |
| Ex. 111 | 5-[4-(4-Bromo-1H-pyrazol-3-ylmethyl)-piperazin-1-yl]-2-furan-2-yl-[1,2,4]triazolo[1,5-a][1,3,5]triazin-7-ylamine | 446 [M + H]+ | Ex. 1 |
| Ex. 112 | 2-Furan-2-yl-5-[4-(2-methyl-1H-imidazol-4-ylmethyl)-piperazin-1-yl]-[1,2,4]triazolo[1,5-a][1,3,5]triazin-7-ylamine | 381 [M + H]+ | Ex. 1 |
| Ex. 113 | 5-[4-(2-Ethyl-5-methyl-3H-imidazol-4-ylmethyl)-piperazin-1-yl]-2-furan-2-yl-[1,2,4]triazolo[1,5-a][1,3,5]triazin-7-ylamine | 409 [M + H]+ | Ex. 1 |
| Ex. 114 | 2-Furan-2-yl-5-[4-(2-phenyl-1H-imidazol-4-ylmethyl)-piperazin-1-yl]-[1,2,4]triazolo[1,5-a][1,3,5]triazin-7-ylamine | 443 [M + H]+ | Ex. 1 |
| Ex. 115 | 2-Furan-2-yl-5-(4-[1,2,3]thiadiazol-4-ylmethyl-piperazin-1-yl)-[1,2,4]triazolo[1,5-a][1,3,5]triazin-7-ylamine | 385 [M + H]+ | Ex. 1 |
| Ex. 116 | 2-Furan-2-yl-$N^5$-[1-(2-methyl-benyl)-pyrrolidin-2-ylmethyl]-[1,2,4]triazolo[1,5-a][1,3,5]triazine-5,7-diamine | 405 [M + H]+ | Ex. 6 |
| Ex. 117 | 2-Furan-2-yl-$N^5$-[1-(3-methyl-benzyl)-pyrrolidin-2-ylmethyl]-[1,2,4]triazolo[1,5-a][1,3,5]triazine-5,7-diamine | 405 [M + H]+ | Ex. 6 |
| Ex. 118 | $N^5$-[1-(2-Chloro-6-fluoro-3-methyl-benzyl)-pyrrolidin-2-ylmethyl]-2-furan-2-yl-[1,2,4]triazolo[1,5-a][1,3,5]triazine-5,7-diamine | 458 [M + H]+ | Ex. 6 |
| Ex. 119 | $N^5$-[1-(2,6-Difluoro-benyl)-pyrrolidin-2-ylmethyl]-2-furan-2-yl-[1,2,4]triazolo[1,5-a][1,3,5]triazine-5,7-diamine | 427 [M + H]+ | Ex. 6 |
| Ex. 120 | [2-(7-Amino-2-furan-2-yl-[1,2,4]triazolo[1,5-a][1,3,5]triazin-5-ylamino)-ethyl]-methyl-carbamic acid tert-butyl ester | 375 [M + H]+ | Ex. 5 |
| Ex. 121 | $N^5$-[1-(2,5-Difluoro-benzyl)-pyrrolidin-2-ylmethyl]-2-furan-2-yl-[1,2,4]triazolo[1,5-a][1,3,5]triazine-5,7-diamine | 427 [M + H]+ | Ex. 6 |
| Ex. 122 | $N^5$-[1-(3,4-Dichloro-benzyl)-pyrrolidin-2-ylmethyl]-2-furan-2-yl-[1,2,4]triazola[1,5-a][1,3,5]triazine-5,7-diamine | 460 [M + H]+ | Ex. 6 |
| Ex. 123 | $N^5$-[1-(3-Fluoro-benzyl)-pyrrolidin-2-ylmethyl]-2-furan-2-yl-[1,2,4]triazolo[1,5-a][1,3,5]triazine-5,7-diamine | 409 [M + H]+ | Ex. 6 |
| EX. 124 | $N^5$-[1-(2,3-Difluoro-benzyl)-pyrrolidin-2-ylmethyl]-2-furan-2-yl-[1,2,4]triazolo[1,5-a][1,3,5]triazine-5,7-diamine | 427 [M + H]+ | Ex. 6 |
| Ex. 125 | $N^5$-[1-(2,4-Difluoro-benzyl)-pyrrolidin-2-ylmethyl]-2-furan-2-yl-[1,2,4]triazolo[1,5-a][1,3,5]triazine-5,7-diamine | 427 [M + H]+ | Ex. 6 |
| Ex. 126 | 2-Furan-2-yl-$N^5$-[1-(4-methyl-benzyl)-pyrrolidin-2-ylmethyl]-[1,2,4]triazolo[1,5-a][1,3,5]triazine-5,7-diamine | 405 [M + H]+ | Ex. 6 |
| Ex. 127 | $N^5$-[1-(3,5-Dichloro-benzyl)-pyrrolidin-2-ylmethyl]-2-furan-2-yl-[1,2,4]triazolo[1,5-a][1,3,5]triazine-5,7-diamine | 460 [M + H]+ | Ex. 6 |
| Ex. 128 | $N^5$-[1-(3,5-Difluoro-benzyl)-pyrrolidin-2-ylmethyl]-2-furan-2-yl-[1,2,4]triazolo[1,5-a][1,3,5]triazine-5,7-diamine | 427 [M + H]+ | Ex. 6 |
| Ex. 129 | 2-{[(7-Amino-2-furan-2-yl-[1,2,4]triazolo[1,5-a][1,3,5]triazin-5-yl)-methyl-amino]-methyl}-pyrrolidine-1-carboxylic acid tert-butyl ester | 415 [M + H]+ | Ex. 5 |
| Ex. 130 | $N^5$-[1-(2,4-Dichloro-benzyl)-pyrrolidin-2-ylmethyl]-2-furan-2-yl-[1,2,4]triazolo[1,5-a][1,3,5]triazine-5,7-diamine | 460 [M + H]+ | Ex. 6 |
| Ex. 131 | $N^5$-[1-(2,6-Dimethyl-benzyl)-pyrrolidin-2-ylmethyl]-2-furan-2-yl-[1,2,4]triazolo[1,5-a][1,3,5]triazine-5,7-diamine | 419 [M + H]+ | Ex. 6 |
| Ex. 132 | $N^5$-[1-(2-Chloro-quinolin-3-ylmethyl)-pyrrolidin-2-ylmethyl]-2-furan-2-yl-[1,2,4]triazolo[1,5-a][1,3,5]triazine-5,7-diamine | 477 [M + H]+ | Ex. 6 |

| Example | Compound Name | Mass Spec. (m/z) | Synthetic Method |
|---|---|---|---|
| Ex. 133 | $N^5$-[1-(5-Chloro-furan-2-ylmethyl)-pyrrolidin-2-ylmethyl]-2-furan-2-yl-[1,2,4]triazolo[1,5-a][1,3,5]triazine-5,7-diamine | 416 [M + H]+ | Ex. 6 |
| Ex. 134 | 2-Furan-2-yl-$N^5$-[1-(2,3,6-trifluoro-benzyl)-pyrrolidin-2-ylmethyl]-[1,2,4]triazolo[1,5-a][1,3,5]triazine-5,7-diamine | 445 [M + H]+ | Ex. 6 |
| Ex. 135 | 2-Furan-2-yl-$N^5$-[1-(2,4,6,-trifluoro-benzyl)-pyrrolidin-2-ylmethyl]-[1,2,4]triazolo[1,5-a][1,3,5]triazine-5,7-diamine | 445 [M + H]+ | Ex. 6 |
| Ex. 136 | 2-Furan-2-yl-$N^5$-[1-(2,4,5,-trifluoro-benzyl)-pyrrolidin-2-ylmethyl]-[1,2,4]triazolo[1,5-a][1,3,5]triazine-5,7-diamine | 445 [M + H]+ | Ex. 6 |
| Ex. 137 | 2-[(7-Amino-2-furan-2-yl-[1,2,4]triazolo[1,5-a][1,3,5]triazin-5-ylamino)-methyl]-piperidine-1-carboxylic acid tert-butyl ester | 415 [M + H]+ | Ex. 5 |
| Ex. 138 | $N^5$-[1-(3-Chloro-2-fluoro-5-trifluoromethyl-benzyl)-pyrrolidin-2-ylmethyl]-2-furan-2-yl-[1,2,4]triazolo[1,5-a][1,3,5]triazine-5,7-diamine | 512 [M + H]+ | Ex. 6 |
| Ex. 139 | $N^5$-[1-(4-Chloro-benzyl)-piperidin-3-ylmethyl]-2-furan-2-yl-[1,2,4]triazolo[1,5-a][1,3,5]triazine-5,7-diamine | 440 [M + H]+ | Ex. 18 + 1 |
| Ex. 140 | $N^5$-[1-(2,6-Difluoro-benzyl)-pyrrolidin-2-ylmethyl]-2-furan-2-yl-N5-methyl-[1,2,4]triazolo[1,5-a][1,3,5]triazine-5,7-diamine | 441 [M + H]+ | Ex. 19 |
| Ex. 141 | $N^5$-[1-(2-Chloro-3,6-difluoro-benzyl)-pyrrolidin-2-ylmethyl]-2-furan-2-yl-N5-methyl-[1,2,4]triazolo[1,5-a][1,3,5]triazine-5,7-diamine | 476 [M + H]+ | Ex. 19 |
| Ex. 142 | $N^5$-[1-(3-Chloro-2-fluoro-6-trifluoromethyl-benzyl)-pyrrolidin-2-ylmethyl]-2-furan-2-yl-[1,2,4]triazolo[1,5-a][1,3,5]triazine-5,7-diamine | 512 [M + H]+ | Ex. 6 |
| Ex. 143 | 2-Furan-2-yl-$N^5$-(1-quinolin-3-ylmethyl-pyrrolidin-2-ylmethyl)-[1,2,4]triazolo[1,5-a][1,3,5]triazine-5,7-diamine | 442 [M + H]+ | Ex. 6 |
| Ex. 144 | 2-Furan-2-yl-$N^5$-[1-(5-methyl-isoxazol-3-ylmethyl)-piperidin-3-ylmethyl]-[1,2,4]triazolo[1,5-a][1,3,5]triazine-5,7-diamine | 410 [M + H]+ | Ex. 19 |
| Ex. 145 | $N^5$-[1-(3-Chloro-5-trifluoromethyl-benzyl)-pyrrolidin-2-ylmethyl]-2-furan-2-yl-[1,2,4]triazolo[1,5-a][1,3,5]triazine-5,7-diamine | 477 [M + H]+ | Ex. 6 |
| Ex. 146 | $N^5$-[1-(4-Fluoro-3-methyl-benzyl)-pyrrolidin-2-ylmethyl]-2-furan-2-yl-[1,2,4]triazolo[1,5-a][1,3,5]triazine-5,7-diamine | 423 [M + H]+ | Ex. 6 |
| Ex. 147 | $N^5$-[1-(2-Bromo-5-fluoro-benzyl)-pyrrolidin-2-ylmethyl]-2-furan-2-yl-[1,2,4]triazolo[1,5-a][1,3,5]triazine-5,7-diamine | 488 [M + H]+ | Ex. 6 |
| Ex. 148 | $N^5$-[1-(4-Chloro-3-fluoro-benzyl)-pyrrolidin-2-ylmethyl]-2-furan-2-yl-[1,2,4]triazolo[1,5-a][1,3,5]triazine-5,7-diamine | 444 [M + H]+ | Ex. 6 |
| Ex. 149 | $N^5$-[1-(2-Fluoro-benzyl)-pyrrolidin-2-ylmethyl]-2-furan-2-yl-N5-methyl-[1,2,4]triazolo[1,5-a][1,3,5]triazine-5,7-diamine | 423 [M + H]+ | Ex. 19 |
| Ex. 150 | $N^5$-[1-(3-Chloro-2-fluoro-benzyl)-pyrrolidin-2-ylmethyl]-2-furan-2-yl-[1,2,4]triazolo[1,5-a][1,3,5]triazine-5,7-diamine | 444 [M + H]+ | Ex. 6 |
| Ex. 151 | $N^5$-[1-(2-Fluoro-5-trifluoromethyl-benzyl)-pyrrolidin-2-ylmethyl]-2-furan-2-yl-[1,2,4]triazolo[1,5-a][1,3,5]triazine-5,7-diamine | 477 [M + H]+ | Ex. 6 |
| Ex. 152 | $N^5$-[1-(2-Fluoro-4-trifluoromethyl-benzyl)-pyrrolidin-2-ylmethyl]-2-furan-2-yl-[1,2,4]triazolo[1,5-a][1,3,5]triazine-5,7-diamine | 477 [M + H]+ | Ex. 6 |
| Ex. 153 | 2-Furan-2-yl-$N^5$-(1-quinolin-4-ylmethyl-pyrrolidin-2-ylmethyl)-[1,2,4]triazolo[1,5-a][1,3,5]triazine-5,7-diamine | 442 [M + H]+ | Ex. 6 |
| Ex. 154 | 2-(3-Fluoro-phenyl)-5-(4-quinolin-2-ylmethyl-piperazin-1-yl)-[1,2,4]triazolo[1,5-a][1,3,5]triazin-7-ylamine | 456 [M + H]+ | Ex. 10 |
| Ex. 155 | 2-(3-Fluoro-phenyl)-5-(4-quinolin-3-ylmethyl-piperazin-1-yl)-[1,2,4]triazolo[1,5-a][1,3,5]triazin-7-ylamine | 456 [M + H]+ | Ex. 10 |
| Ex. 156 | 2-(3-Fluoro-phenyl)-5-(4-quinolin-4-ylmethyl-piperazin-1-yl)-[1,2,4]triazolo[1,5-a][1,3,5]triazin-7-ylamine | 456 [M + H]+ | Ex. 10 |
| Ex. 157 | 2-(3-Fluoro-phenyl)-5-(4-pyridin-2-ylmethyl-piperazin-1-yl)-[1,2,4]triazolo[1,5-a][1,3,5]triazin-7-ylamine | 406 [M + H]+ | Ex. 10 |
| Ex. 158 | 2-(3-Fluoro-phenyl)-5-(4-pyridin-3-ylmethyl-piperazin-1-yl)-[1,2,4]triazolo[1,5-a][1,3,5]triazin-7-ylamine | 406 [M + H]+ | Ex. 10 |
| Ex. 159 | 2-(3-Fluoro-phenyl)-5-(4-pyridin-4-ylmethyl-piperazin-1-yl)-[1,2,4]triazolo[1,5-a][1,3,5]triazin-7-ylamine | 406 [M + H]+ | Ex. 10 |
| Ex. 160 | $N^5$-[1-(3,5-Difluoro-benzyl)-pyrrolidin-2-ylmethyl]-2-furan-2-yl-N5-methyl-[1,2,4]triazolo[1,5-a][1,3,5]triazine-5,7-diamine | 441 [M + H]+ | Ex. 19 + 1 |
| Ex. 161 | $N^5$-[1-(3-Chloro-2,6-difluoro-benzyl)-pyrrolidin-2-ylmethyl]-2-furan-2-yl-N5-methyl-[1,2,4]triazolo[1,5-a][1,3,5]triazine-5,7-diamine | 476 [M + H]+ | Ex. 19 + 1 |
| Ex. 162 | $N^5$-[1-(3-Fluoro-benzyl)-pyrrolidin-2-ylmethyl]-2-furan-2-yl-N5-methyl-[1,2,4]triazolo[1,5-a][1,3,5]triazine-5,7-diamine | 423 [M + H]+ | Ex. 19 + 1 |
| Ex. 163 | 2-Furan-2-yl-$N^5$-methyl-N5-[1-(2,3,6-trifluoro-benzyl)-pyrrolidin-2-ylmethyl]-[1,2,4]triazolo[1,5-a][1,3,5]triazine-5,7-diamine | 459 [M + H]+ | Ex. 19 + 1 |
| Ex. 164 | $N^5$-[1-(2,3-Difluoro-benzyl)-piperidin-3-ylmethyl]-2-furan-2-yl-[1,2,4]triazolo[1,5-a][1,3,5]triazine-5,7-diamine | 441 [M + H]+ | Ex. 18 + 1 |
| Ex. 165 | 2-Furan-2-yl-$N^5$-(1-quinolin-2-ylmethyl-piperidin-3-ylmethyl)-[1,2,4]triazolo[1,5-a][1,3,5]triazine-5,7-diamine | 456 [M + H]+ | Ex. 18 + 1 |
| Ex. 166 | 5-(4-Benzofuran-2-ylmethyl-piperazin-1-yl)-2-furan-2-yl-[1,2,4]triazolo[1,5-a][1,3,5]triazin-7-ylamine | 417 [M + H]+ | Ex. 1 |
| Ex. 167 | 2-Furan-2-yl-5-(4-thiazol-2-ylmethyl-piperazin-1-yl)-[1,2,4]triazolo[1,5-a][1,3,5]triazin-7-ylamine | 384 [M + H]+ | Ex. 1 |
| Ex. 168 | 2-Furan-2-yl-5-[4-(1H-indol-5-ylmethyl)-piperazin-1-yl]-[1,2,4]triazolo[1,5-a][1,3,5]triazin-7-ylamine | 416 [M + H]+ | Ex. 1 |
| Ex. 169 | 2-Furan-2-yl-5-[4-(1-methyl-1H-indol-2-ylmethyl)-piperazin-1-yl]-[1,2,4]triazolo[1,5-a][1,3,5]triazin-7-ylamine | 430 [M + H]+ | Ex. 1 |

-continued

| Example | Compound Name | Mass Spec. (m/z) | Synthetic Method |
|---|---|---|---|
| Ex. 170 | 2-Furan-2-yl-5-[4-(6-methyl-pyridin-2-ylmethyl)-piperazin-1-yl]-[1,2,4]triazolo[1,5-a][1,3,5]triazin-7-ylamine | 392 [M + H]+ | Ex. 1 |
| Ex. 171 | 5-[4-(2-Chloro-6-methoxy-quinolin-3-ylmethyl)-piperazin-1-yl]-2-furan-2-yl-[1,2,4]triazolo[1,5-a][1,3,5]triazin-7-ylamine | 492 [M + H]+ | Ex. 1 |
| Ex. 172 | 2-Furan-2-yl-5-[4-(5-methyl-1H-indol-2-ylmethyl)-piperazin-1-yl]-[1,2,4]triazolo[1,5-a][1,3,5]triazin-7-ylamine | 430 [M + H]+ | Ex. 1 |
| Ex. 173 | 5-[4-(5-Chloro-1H-indol-2-ylmethyl)-piperazin-1-yl]-2-furan-2-yl-[1,2,4]triazolo[1,5-a][1,3,5]triazin-7-ylamine | 451 [M + H]+ | Ex. 1 |
| Ex. 174 | $N^5$-(1-Benzofuran-2-ylmethyl-pyrrolidin-2-ylmethyl)-2-furan-2-yl-[1,2,4]triazolo[1,5-a][1,3,5]triazine-5,7-diamine | 431 [M + H]+ | Ex. 6 |
| Ex. 175 | $N^5$-[1-(4-Chloro-1-methyl-1H-pyrazol-3-ylmethyl)-pyrrolidin-2-ylmethyl]-2-furan-2-yl-[1,2,4]triazolo[1,5-a][1,3,5]triazine-5,7-diamine | 429 [M + H]+ | Ex. 6 |
| Ex. 176 | $N^5$-[1-(4-Bromo-1-methyl-1H-pyrazol-3-ylmethyl)-pyrrolidin-2-ylmethyl]-2-furan-2-yl-[1,2,4]triazolo[1,5-a][1,3,5]triazine-5,7-diamine | 473 [M + H]+ | Ex. 6 |
| Ex. 177 | 2-[(7-Amino-2-furan-2-yl-[1,2,4]triazolo[1,5-a][1,3,5]triazin-5-ylamino)-methyl]-piperidine-1-carboxylic acid tert-butyl ester | 415 [M + H]+ | Ex. 3 |
| Ex. 178 | $N^5$-[1-(3,5-Dichloro-pyridin-4-ylmethyl)-pyrrolidin-2-ylmethyl]-2-furan-2-yl-[1,2,4]triazolo[1,5-a][1,3,5]triazine-5,7-diamine | 461 [M + H]+ | Ex. 7 |
| Ex. 179 | 2-Furan-2-yl-5-[4-(2-methyl-pyridin-2-ylmethyl)-piperazin-1-yl]-[1,2,4]triazolo[1,5-a][1,3,5]triazin-7-ylamine | 392 [M + H]+ | Ex. 1 |
| Ex. 180 | 2-Furan-2-yl-$N^5$-[1-(3-methyl-pyridin-2-ylmethyl)-pyrrolidin-2-ylmethyl]-[1,2,4]triazolo[1,5-a][1,3,5]triazine-5,7-diamine | 406 [M + H]+ | Ex. 7 |
| Ex. 181 | 5-[4-(2,6-Dichloro-5-fluoro-pyridin-3-ylmethyl)-piperazin-1-yl]-2-furan-2-yl-[1,2,4]triazolo[1,5-a][1,3,5]triazin-7-ylamine | 324 [M + H]+ | Ex. 4 |
| Ex. 182 | $N^5$-[1-(3,6-Dichloro-5-fluoro-pyridin-2-ylmethyl)-pyrrolidin-2-ylmethyl]-2-furan-2-yl-[1,2,4]triazolo[1,5-a][1,3,5]triazine-5,7-diamine | 479 [M + H]+ | Ex. 7 |
| Ex. 183 | 5-[4-(2,4-Dimethyl-pyridin-3-ylmethyl)-piperazin-1-yl]-2-furan-2-yl-[1,2,4]triazolo[1,5-a][1,3,5]triazin-7-ylamine | 406 [M + H]+ | Ex. 4 |
| Ex. 184 | $N^5$-[1-(2,4-Dimethyl-pyridin-3-ylmethyl)-pyrrolidin-2-ylmethyl]-2-furan-2-yl-[1,2,4]triazolo[1,5-a][1,3,5]triazine-5,7-diamine | 420 [M + H]+ | Ex. 7 |
| Ex. 185 | $N^5$-[1-(2,6-Dichloro-benzyl)-piperidin-2-ylmethyl]-2-furan-2-yl-[1,2,4]triazolo[1,5-a][1,3,5]triazine-5,7-diamine | 473 [M + H]+ | Ex. 19 |
| Ex. 186 | $N^5$-[1-(2-Chloro-6-fluoro-benzyl)-piperidin-2-ylmethyl]-2-furan-2-yl-[1,2,4]triazolo[1,5-a][1,3,5]triazine-5,7-diamine | 457 [M + H]+ | Ex. 19 |
| Ex. 187 | $N^5$-[1-(2-Fluoro-benzyl)-piperidin-2-ylmethyl]-2-furan-2-yl-[1,2,4]triazolo[1,5-a][1,3,5]triazine-5,7-diamine | 421 [M + H]+ | Ex. 19 |
| Ex. 188 | $N^5$-[1-(2-Chloro-benzyl)-piperidin-2-ylmethyl]-2-furan-2-yl-[1,2,4]triazolo[1,5-a][1,3,5]triazine-5,7-diamine | 439 [M + H]+ | Ex. 19 |
| Ex. 189 | $N^5$-[1-(6-Chloro-pyridin-3-ylmethyl)-piperidin-2-ylmethyl]-2-furan-2-yl-[1,2,4]triazolo[1,5-a][1,3,5]triazine-5,7-diamine | 440 [M + H]+ | Ex. 19 |
| Ex. 190 | 5-[4-(2-Chloro-pyridin-3-ylmethyl)-piperazin-1-yl]-2-furan-2-yl-[1,2,4]triazolo[1,5-a][1,3,5]triazin-7-ylamine | 413 [M + H]+ | Ex. 4 |
| Ex. 191 | 5-[4-(2,6-Dichloro-pyridin-4-ylmethyl)-piperazin-1-yl]-2-furan-2-yl-[1,2,4]triazolo[1,5-a][1,3,5]triazin-7-ylamine | 447 [M + H]+ | Ex. 4 |
| Ex. 192 | 2-Furan-2-yl-5-[4-(4-methyl-pyridin-2-ylmethyl)-piperazin-1-yl]-[1,2,4]triazolo[1,5-a][1,3,5]triazin-7-ylamine | 392 [M + H]+ | Ex. 4 |
| Ex. 193 | $N^5$-[1-(3-Chloro-2-fluoro-4-methyl-benzyl)-pyrrolidin-2-ylmethyl]-2-furan-2-yl-[1,2,4]triazolo[1,5-a][1,3,5]triazine-5,7-diamine | 458 [M + H]+ | Ex. 6 |
| Ex. 194 | $N^5$-[1-(3-Fluoro-5-methyl-benzyl)-pyrrolidin-2-ylmethyl]-2-furan-2-yl-[1,2,4]triazolo[1,5-a][1,3,5]triazine-5,7-diamine | 477 [M + H]+ | Ex. 6 |
| Ex. 195 | $N^5$-[1-(3-Fluoro-4-methyl-benzyl)-pyrrolidin-2-ylmethyl]-2-furan-2-yl-[1,2,4]triazolo[1,5-a][1,3,5]triazine-5,7-diamine | 477 [M + H]+ | Ex. 6 |
| Ex. 196 | $N^5$-[1-(2-Bromo-4-fluoro-benzyl)-pyrrolidin-2-ylmethyl]-2-furan-2-yl-[1,2,4]triazolo[1,5-a][1,3,5]triazine-5,7-diamine | 488 [M + H]+ | Ex. 6 |
| Ex. 197 | 2-Furan-2-yl-$N^5$-methyl-N5-[1-(2,4,6-trifluoro-benzyl)-pyrrolidin-2-ylmethyl]-[1,2,4]triazolo[1,5-a][1,3,5]triazine-5,7-diamine | 459 [M + H]+ | Ex. 19 + 1 |
| Ex. 198 | 2-Furan-2-yl-$N^5$-[1-(5-methyl-isoxazol-3-ylmethyl)-piperidin-2-ylmethyl]-[1,2,4]triazolo[1,5-a][1,3,5]triazine-5,7-diamine | 410 [M + H]+ | Ex. 19 |
| Ex. 199 | 2-Furan-2-yl-$N^5$-(1-quinolin-2-ylmethyl-piperidin-2-ylmethyl)-[1,2,4]triazolo[1,5-a][1,3,5]triazine-5,7-diamine | 456 [M + H]+ | Ex. 19 |
| Ex. 200 | 2-Furan-2-yl-$N^5$-(1-pyridin-2-ylmethyl-piperidin-2-ylmethyl)-[1,2,4]triazolo[1,5-a][1,3,5]triazine-5,7-diamine | 406 [M + H]+ | Ex. 19 |
| Ex. 201 | $N^5$-[1-(2,6-Dichloro-5-fluoro-pyridin-3-ylmethyl)-piperidin-2-ylmethyl]-2-furan-2-yl-[1,2,4]triazolo[1,5-a][1,3,5]triazine-5,7-diamine | 493 [M + H]+ | Ex. 19 |
| Ex. 202 | $N^5$-[1-(3,5-Dichloro-pyridin-4-ylmethyl)-piperidin-2-ylmethyl]-2-furan-2-yl-[1,2,4]triazolo[1,5-a][1,3,5]triazine-5,7-diamine | 475 [M + H]+ | Ex. 19 |
| Ex. 203 | 2-Furan-2-yl-$N^5$-methyl-N5-[1-(5-methyl-isoxazol-3-ylmethyl)-piperidin-2-ylmethyl]-[1,2,4]triazolo[1,5-a][1,3,5]triazine-5,7-diamine | 410 [M + H]+ | Ex. 19 |
| Ex. 204 | $N^2$-(1-Benzyl-pyrrolidin-3-yl)-7-furan-2-yl-pyrazolo[1,5-a][1,3,5]triazine-2,4-diamine | 376 [M + H]+ | Ex. 6 |

-continued

| Example | Compound Name | Mass Spec. (m/z) | Synthetic Method |
|---|---|---|---|
| Ex. 205 | $N^2$-(1-Benzyl-piperidin-4-yl)-7-furan-2-yl-pyrazolo[1,5-a][1,3,5]triazine-2,4-diamine | 390 [M + H]+ | Ex. 5 |
| Ex. 206 | 7-Furan-2-yl-$N^2$-[1-(5-methyl-isoxazol-3-ylmethyl)-pyrrolidin-3-yl]-pyrazolo[1,5-a][1,3,5]triazine-2,4-diamine | 381 [M + H]+ | Ex. 15 |
| Ex. 207 | 7-Furan-2-yl-$N^2$-[1-(5-methyl-isoxazol-3-ylmethyl)-pyrrolidin-2-ylmethyl]-pyrazolo[1,5-a][1,3,5]triazine-2,4-diamine | 395 [M + H]+ | Ex. 15 |
| Ex. 208 | 7-Furan-2-yl-$N^2$-methyl-N2-[1-(5-methyl-isoxazol-3-ylmethyl)-pyrrolidin-2-ylmethyl]-pyrazolo[1,5-a][1,3,5]triazine-2,4-diamine | 409 [M + H]+ | Ex. 15 |
| Ex. 209 | 7-Furan-2-yl-2-[4-(5-methyl-isoxazol-3-ylmethyl)-piperazin-1-yl]-pyrazolo[1,5-a][1,3,5]triazin-4-ylamine | 381 [M + H]+ | Ex. 12 |
| Ex. 210 | 2-[4-(3,5-Dimethyl-isoxazol-4-ylmethyl)-[1,4]diazepan-1-yl]-7-furan-2-yl-pyrazolo[1,5-a][1,3,5]triazin-4-ylamine | 409 [M + H]+ | Ex. 14 |
| Ex. 211 | $N^5$-[1-(3-Chloro-1-methyl-1H-pyrazol-4-ylmethyl)-pyrrolidin-2-ylmethyl]-2-furan-2-yl-[1,2,4]triazolo[1,5-a][1,3,5]triazine-5,7-diamine | 429 [M + H]+ | Ex. 6 |
| Ex. 212 | $N^5$-[1-(2-Chloro-pyridin-4-ylmethyl)-pyrrolidin-2-ylmethyl]-2-furan-2-yl-[1,2,4]triazolo[1,5-a][1,3,5]triazine-5,7-diamine | 426 [M + H]+ | Ex. 4 |
| Ex. 213 | 2-Furan-2-yl-$N^5$-{2-[4-(2,4,6-trifluoro-phenyl)-piperazin-1-yl]-ethyl}-[1,2,4]triazolo[1,5-a][1,3,5]triazine-5,7-diamine | 406 [M + H]+ | Ex. 20 |
| Ex. 214 | 2-Furan-2-yl-$N^5$-methyl-$N^5$-{2-[4-(2,4,6-trifluoro-phenyl)-piperazin-1-yl]-ethyl}-[1,2,4]triazolo[1,5-a][1,3,5]triazine-5,7-diamine | 474 [M + H]+ | Ex. 20 |

The $A_{2a}$ modulating activity of compounds of the present invention can be assessed by methods described in the following examples.

EXAMPLE 215

Numerous compounds of the present invention were prepared (see working examples and table above) and tested. Specifically, the $K_i$ values for rat and human $A_1$ adenosine receptors and for human $A_{2a}$ adenosine receptors were determined according to the following binding assay protocol. The ratio $A_{2a}/A_1$ was also calculated.

Materials

Adenosine deaminase and HEPES were purchased from Sigma-Aldrich (St. Louis, Mo.). Ham's F-12 cell culture medium and fetal bovine serum were purchased from GIBCO Life Technologies (Gaithersburg, Md.). Antibiotic G-418, Falcon 150 mM culture plates and Costar 12-well culture plates were purchased from Fisher (Pittsburgh, Pa.). [$^3$H]CPX was purchased from DuPont-New England Nuclear Research Products (Boston, Mass.). Penicillin/streptomycin antibiotic mixture was purchased from Mediatech (Washington, D.C.). The composition of HEPES-buffered Hank's solution was: 130 mM NaCl, 5.0 mM Cl, 1.5 mM $CaCl_2$, 0.41 mM $MgS0_4$, 0.49 mM $Na_2HPO_4$, 0.44 mM, $KH_2PO_4$, 5.6 mM dextrose, and 5 mM HEPES (pH 7.4).

Membrane Preparation $A_{2a}$ Receptor: Membranes were prepared from rat brain tissues purchased from Pel-Freez (Brown Deer, Wis.). Tissues were homogenized in buffer A (10 mM EDTA, 10 mM Na-HEPES, pH 7.4) supplemented with protease inhibitors (10 μg/ml benzamidine, 100 μM PMSF, and 2 μg/ml each of aprotinin, pepstatin and leupeptin), and centrifuged at 20,000×g for 20 minutes. Pellets were resuspended and washed twice with buffer HE (10 mM Na-HEPES, 1 mM EDTA, pH 7.4, plus protease inhibitors). Final pellets were resuspended in buffer HE, supplemented with 10% (w/v) sucrose and protease inhibitors, and frozen in aliquots at −80° C. Protein concentrations were measured using BCA protein assay kit (Pierce, Rockford, Ill.).

$A_1$ Receptor: Membranes were prepared from rat cerebral cortex isolated from freshly euthanized rats. Tissues were homogenized in buffer A (10 mM EDT, 10 mM Na-HEPES, pH 7.4) supplemented with protease inhibitors (10 μg/ml benzamidine, 100 μM PMSF, and 2 μg/ml each of aprotinin, pepstatin and leupeptin), and centrifuged at 20,000×g for 20 minutes. Pellets were resuspended and washed twice with buffer HE (10 mM Na-HEPES, 1 mM EDTA, pH 7.4, plus protease inhibitors). Final pellets were resuspended in buffer HE, supplemented with 10% (w/v) sucrose and protease inhibitors, and frozen in aliquots at −80° C. Protein concentrations were measured using BCA protein assay kit (Pierce).

Radioligand Binding Assays

Membranes (40-70 μg membrane protein), radioligands and varying concentrations of test compounds of the present invention were incubated in triplicates in 0.1 ml buffer HE plus 2 units/ml adenosine deaminase for 2.5 hours at 21° C. Radioligand [$^3$H]DPCPX was used for competition binding assays on $A_1$ receptors and [$^3$H]ZM241385 was used for $A_{2a}$ adenosine receptors. Nonspecific binding was measured in the presence of 10 μM NECA for $A_1$ receptors, or 10 μM XAC for $A_{2a}$ receptors. Binding assays were terminated by filtration over Whatman GF/C glass fiber filters using a BRANDEL cell harvester. Filters were rinsed three times with 3-4 mL ice cold 10 mM Tris-HCl, pH 7.4 and 5 mM $MgCl_2$ at 4° C., and were counted in a Wallac β-counter.

Analysis of Binding Data $K_i$ determination: Competition binding data were fit to a single-site binding model and plotted using Prizm Graph-Pad. Cheng-Prusoff equation $K_i=IC_{50}/(1+[I]/K_d)$ was used to calculate $K_i$ values from $IC_{50}$, values, where $K_i$ is the affinity constant for the competing test compound, [I] is the concentration of the free radioligand, and $K_d$ is the affinity constant for the radioligand.

$A_{2a}$% binding: Data were generally expressed as percentage of total specific binding at 1 μM of competing test compound (% total specific binding)=100%×(specific binding with 1 μM of competing test compound/total specific binding).

Results

Compounds of the present invention typically exhibited $K_i$ values of less than 10 μM and $A_{2a}$% binding ranging from 1% to 50%; some compounds exhibited $K_1$ values of less than 1 μM.

EXAMPLE 216

Catalepsy Experiments

Haloperidol-induced catalepsy was used to mimic the effects of Parkinson's disease in rats and mice. Animals were injected with haloperidol, which causes immobility. A test compound of the present invention was then administered orally and the compound's ability to reverse these Parkinson's-like symptoms was analyzed. For reference, see Sanberg et al. Behavioral Neurosciende 102: 748-759 (1988).

Rats

Male Sprague-Dawley rats (225-275 g) were injected with haloperidol, (1 mg/kg s.c.) to induce catalepsy. These rats were then subjected to the bar test. In this test, the rats forelimbs were placed on an aluminum bar (1 cm in diameter) suspended horizontally 10 cm above the surface of the bench. The elapsed time until the rat placed one forepaw back on the bench was measured, with a maximum time of 120 seconds allowed. It should be noted that these rats were in a cataleptic state and therefore were unable to correct an externally imposed posture (i.e., the cataleptic rats, when placed in this unnatural position, were unable to come down from the horizontal bar over a period of 120 seconds or more). Once the rats showed a stable baseline cataleptic response (about three hours after haloperidol injection), a test compound of the present invention or vehicle alone is administered orally, and catalepsy data from the bar test were measured every 30 minutes for the next 3 hours. Data were analyzed by one factor analysis of variance with Dunnett's 't' test used to make post-hoc comparisons. Many compounds of this invention showed oral activity at a dosage of 10 mg/kg or lower, which allowed the cataleptic animals to come down from the bar within 60 seconds and remained in a catalepsy-free state for at least 60 minutes.

Mice

Mice catalepsy experiment was conducted in the same manner as described above except mice (CD-1; 25-30 g) were used instead of rats, the dose of haloperidol was 3 mg/kg s.c. instead of 1 mg/kg s.c., and the bar was suspended 4.5 cm instead of 10 cm above the surface of the bench. Many compounds of this invention showed oral activity at a dosage of 10 mg/kg or lower, which allowed the cataleptic animals to come down from the bar within 60 seconds and remained in a catalepsy-free state for at least 60 minutes.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of the following formula:

(I)

$R^1$—Y—$X^2$—L—$X^1$ [structure shown]

or a pharmaceutically acceptable salt or N-oxide thereof; wherein
A is aryl or heteroaryl;
B is N or $CR^2$;
each of $R^2$ and $R^3$ is independently hydrogen, alkyl, cycloalkyl, cycloalkenyl, aryl, aralkyl, heterocycloalkyl, heterocycloalkenyl, heteroaryl, or heteroaralkyl;
each of $X^1$ and $X^2$ is independently $C_{1-6}$ alkylene, $C_{2-6}$ alkenylene, $C_{2-6}$ alkynylene, or a bond;
L is

[structure shown with $(R')_m$]

wherein:
each R' independently, is hydrogen, alkyl, alkenyl, alkynyl, alkoxy, acyl, halo, hydroxy, amino, nitro, oxo, thioxo, cyano, guanadino, amidino, carboxy, sulfo, sulfoxy, mercapto, alkylsulfanyl, alkylsulfinyl, alkylsulfonyl, aminocarbonyl, alkylcarbonylamino, alkylsulfonylamino, alkoxycarbonyl, alkylcarbonyloxy, urea, thiourea, sulfamoyl, sulfamide, carbamoyl, cycloalkyl, cycloalkyloxy, cycloalkylsulfanyl, heterocycloalkyl, heterocycloalkyloxy, heterocycloalkylsulfanyl, aryl, aryloxy, arylsulfanyl, aroyl, heteroaryl, heteroaryloxy, heteroarylsulfanyl, or heteroaroyl; provided that two adjacent R' groups can join together to form a 4- to 8-membered optionally substituted cyclic moiety;
$X^a$ is —$C(R^2)(R^3)$—, —S—, —SO—, or —$SO_2$—;
$X^b$ is —$C(R^2)(R^3)$—, —$NR^2$—, —O—, —S—, —SO—, or —$SO_2$—;
each of p, and m, and independently, is 0-3;
Y is —$C(R^2)(R^3)$—, —O—, —S—, —SO—, —$SO_2$—, —CO—, —$CO_2$—, or a bond; and
$R^1$ is alkyl, alkenyl, alkynyl, cycloalkyl, cycloalkylalkyl, cycloalkenyl, cycloalkenylalkyl, aryl, aralkyl, heterocyclyl, or heterocyclylalkyl;
provided that (1) when $X^1$ is a bond, then $X^2$ is alkylene and $R^1$ is heteroaryl.

2. The compound of claim 1, wherein p is 1-2.
3. The compound of claim 2, wherein m is 1 and R' is $C_{1-4}$ alkyl, or m is 0.
4. The compound of claim 2, wherein $X^1$ is a bond.
5. The compound of claim 4, wherein $X^2$ is an alkylene.
6. The compound of claim 5, wherein $R^1$ is aryl or heteroaryl selected from the group consisting of furyl, thienyl, pyrrolyl, okazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, triazinyl, quinolinyl, isoquinolinyl, indolyl, isoindolyl, benzofuryl, benzothiophenyl, benzimidazolyl, benzthiazolyl, furopyridyl, and thienopyridyl.

7. The compound of claim 6, wherein $R^1$ is unsubstituted or substituted with $C_{1-4}$ alkyl, halo, hydroxy, $C_{1-4}$ alkoxy, or $C_{1-4}$ alkylthio.

8. The compound of claim 7, wherein $R^1$ is unsubstituted or substituted with methyl, ethyl, propyl, fluoro, chloro, bromo, hydroxy, methoxy, ethoxy, propoxy, trifluoromethyl, hydroxymethyl, hydroxyethyl, hydroxypropyl, methylthio, ethylthio, or propropylthio.

9. A compound of the following formula:

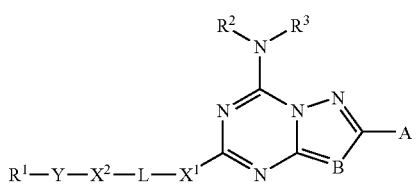

(I)

or a pharmaceutically acceptable salt or N-oxide thereof; wherein

A is aryl or heteroaryl;
B is N or $CR^2$;
each of $R^2$ and $R^3$ is independently hydrogen, alkyl, cycloalkyl, cycloalkenyl, aryl, aralkyl, heterocycloalkyl, heterocycloalkenyl, heteroaryl, or heteroaralkyl;
each of $X^1$ and $X^2$ is independently $C_{1-6}$ alkylene, $C_{2-6}$ alkenylene, $C_{2-6}$ alkynylene, or a bond;
wherein L is

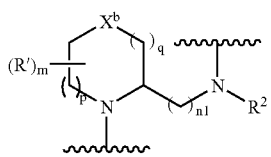

wherein:
each R', independently, is hydrogen, alkyl, alkenyl, alkynyl, alkoxy, acyl, halo, hydroxy, amino, nitro, oxo, thioxo, cyano, guanadino, amidino, carboxy, sulfo, sulfoxy, mercapto, alkylsulfanyl, alkylsulfinyl, alkylsulfonyl, aminocarbonyl, alkylcarbonylamino, alkylsulfonylamino, alkoxycarbonyl, alkylcarbonyloxy, urea, thiourea, sulfamoyl, sulfamide, carbamoyl, cycloalkyl, cycloalkyloxy, cycloalkylsulfanyl, heterocycloalkyl, heterocycloalkyloxy, heterocycloalkylsulfanyl, aryl, aryloxy, arylsulfanyl, aroyl, heteroaryl, heteroaryloxy, heteroarylsulfanyl, or heteroaroyl; provided that two adjacent R' groups can join together to form a 4- to 8-membered optionally substituted cyclic moiety;
$X^a$ is —C($R^2$)($R^3$)—, —S—, —SO—, or —SO$_2$—;
$X^b$ is —C($R^2$)($R^3$)—, —NR$^2$—, —O—, —S—, —SO—, or —SO$_2$—;
each of p, q, and m, independently, is 0-3;
n1 is 0-2; and
Y is —C($R^2$)($R^3$)—, —O—, —S—, —SO—, —SO$_2$—, —CO—, —CO$_2$—, or a bond; and $R^1$ is alkyl, alkenyl, alkynyl, cycloalkyl, cycloalkylalkyl, cycloalkenyl, cycloalkenylalkyl, aryl, aralkyl, heterocyclyl, or heterocyclylalkyl.

10. The compound of claim 9, wherein $X^b$ is —C($R^2$)($R^3$)—, p is 0-1, and q is 1.

11. The compound of claim 10, wherein $X^b$ is —CH$_2$—.

12. The compound of claim 9, wherein $X^b$ is —NR$^2$—, —O—, —S—, —SO—, or —SO$_2$—; p is 0-1; and q is 1.

13. The compound of claim 10, wherein $X^1$ is a bond.

14. The compound of claim 13, wherein $X^2$ is an alkylene optionally substituted with $C_{1-4}$ alkyl, halo, hydroxy, $C_{1-4}$ alkoxy, or $C_{1-4}$ alkylthio.

15. The compound of claim 14, wherein $R^2$ is hydrogen or $C_{1-4}$ alkyl.

16. The compound of claim 15, wherein $R^1$ is alkyl, aryl, or heteroaryl.

17. The compound of claim 16, wherein $R^1$ is phenyl, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, triazinyl, quinolinyl, isoquinolinyl, indolyl, isoindolyl, benzofuryl, benzothiophenyl, benzimidazolyl, benzthiazolyl, furopyridyl, or thienopyridyl; each of which being optionally substituted with $C_{1-4}$ alkyl, halo, hydroxy, $C_{1-4}$ alkoxy, or $C_{1-4}$ alkylthio.

18. A compound of the following formula:

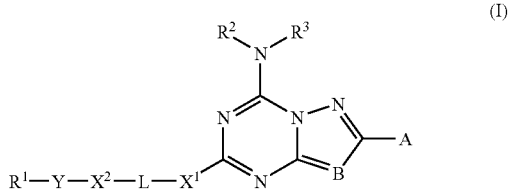

(I)

or a pharmaceutically acceptable salt or N-oxide thereof wherein

A is aryl or heteroaryl;
B is N or $CR^2$;
each of $R^2$ and $R^3$ is independently hydrogen, alkyl, cycloalkyl, cycloalkenyl, aryl, aralkyl, heterocycloalkyl, heterocycloalkenyl, heteroaryl, or heteroaralkyl;
each of $X^1$ and $X^2$ is independently $C_{1-6}$ alkylene, $C_{2-6}$ alkenylene, $C_{2-6}$ alkynylene, or a bond;
wherein L is

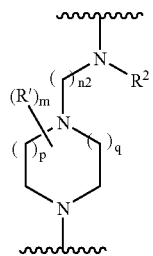

wherein:
each of R' and R", independently, is hydrogen, alkyl, alkenyl, alkynyl, alkoxy, acyl, halo, hydroxy, amino, nitro, oxo, thioxo, cyano, guanadino, amidino, carboxy, sulfo, sulfoxy, mercapto, alkylsulfanyl, alkylsulfinyl, alkylsulfonyl, aminocarbonyl, alkylcarbonylamino, alkylsulfonylamino, alkoxycarbonyl, alkylcarbonyloxy, urea, thiourea, sulfamoyl, sulfamide, carbamoyl, cycloalkyl, cycloalkyloxy, cycloalkylsulfanyl, heterocycloalkyl, heterocycloalkyloxy, heterocycloalkylsulfanyl, aryl, aryloxy, arylsulfanyl, aroyl, heteroaryl, heteroaryloxy, heteroarylsulfanyl, or heteroaroyl; provided that two adjacent R' groups can join together to form a 4- to 8-membered optionally substituted cyclic moiety;

$X^a$ is $-C(R^2)(R^3)-$, $-S-$, $-SO-$, or $-SO_2$;

$X^b$ is $-C(R^2)(R^3)-$, $-NR^2-$, $-O-$, $-S-$, $-SO-$, or $-SO_2-$;

each of p, q, and m, independently, is 0-3; and n2 is 2-3

Y is $-C(R^2)(R^3)-$, $-O-$, $-S-$, $-SO-$, $-SO_2-$, $-CO-$, $-CO_2-$, or a bond; and $R^1$ is alkyl, alkenyl, alkynyl, cycloalkyl, cycloalkylalkyl, cycloalkenyl, cycloalkenylalkyl, aryl, aralkyl, heterocyclyl, or heterocyclylalkyl;

provided that when $X^1$ is a bond then $X^2$ is alkylene and $R^1$ is heteroaryl.

19. The compound of claim 18, wherein p is 0 or 1, q is 1, R' is hydrogen or $C_{1-4}$ alkyl, and m is 1-2.

20. The compound of claim 19, wherein $X^1$ is a bond.

21. The compound of claim 20, wherein $X^2$ is a bond or an alkylene optionally substituted with $C_{1-4}$ alkyl, halo, hydroxy, $C_{1-4}$ alkoxy, or $C_{1-4}$ alkylthio.

22. The compound of claim 21, wherein $R^1$ is alkyl, aryl, or heteroaryl.

23. The compound of claim 22, wherein $R^1$ is phenyl, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, triazinyl, quinolinyl, isoquinolinyl, indolyl, isoindolyl, benzofuryl, benzothiophenyl, benzimidazolyl, benzthiazolyl, furopyridyl, or thienopyridyl, each of which being optionally substituted with $C_{1-4}$ alkyl, halo, hydroxy, $C_{1-4}$ alkoxy, or $C_{1-4}$ alkylthio.

24. The compound of claim 1, wherein $R^1$ is alkyl, or heteroaryl.

25. A compound selected from the group consisting of:

2-Furan-2-yl-5-(4-pyridin-2-ylmethyl-piperazin-1-yl)-[1,2,4]triazolo[1,5-a][1,3,5]triazin-7-ylamine, 2-Furan-2-yl-5-[4-(5-methyl-isoxazol-3-ylethyl)-piperazin-1-yl]-[1,2,4]triazolo[1,5-a][1,3,5]triazin-7-ylamine, 5-[4-(3,5-Dimethyl-isoxazol-4-ylmethyl)-piperazin-1-yl]-2-furan-2-yl-[1,2,4]triazolo[1,5-a][1,3,5]triazin-7-ylamine, 5-[4-(3,5-Dichloro-pyridin-4-ylmethyl)-piperazin-1-yl]-2-furan-2-yl-[1,2,4]triazolo[1,5-a][1,3,5]triazin-7-ylamine,

[4-(7-Amino-2-furan-2-yl-[1,2,4]triazolo[1,5-a][1,3,5]triazin-5-yl)-piperazin-1-yl]-(3,5-dichloro-pyridin-4-yl)-methanone, $N^5$-[1-(2,6-Dichloro-benzyl)-pyrrolidin-2-ylmethyl]-2-furan-2-yl-[1,2,4]triazolo[1,5-a][1,3,5]triazine-5,7-diamine, $N^5$-[1-(3,5-Dimethyl-isoxazol-4-ylmethyl)-pyrrolidin-2-ylmethyl]-2-furan-2-yl-[1,2,4]triazolo[1,5-a][1,3,5]triazine-5,7-diamine, 5-[4-(2-Chloro-benzyl)-[1,4]diazepan-1-yl]-2-furan-2-yl-[1,2,4]triazolo[1,5-a][1,3,5]triazin-7-ylamine, 2-Furan-2-yl-5-(4-pyridin-2-ylmethyl-[1,4]diazepan-1-yl)-[1,2,4]triazolo[1,5-a][1,3,5]triazin-7-ylamine, 5-[4-(3,5-Dimethyl-isoxazol-4-ylmethyl)-piperazin-1-yl]-2-(3-fluoro-phenyl)-[1,2,4]triazolo[1,5-a][1,3,5]triazin-7-ylamine, 2-(3-Fluoro-phenyl)-5-[4-(5-methyl-isoxazol-4-ylmethyl)-piperazin-1-yl]-[1,2,4]triazolo[1,5-a][1,3,5]triazin-7-ylamine, 2-[4-(3,5-Dimethyl-isoxazol-4-ylmethyl)-piperazin-1-yl]-7-furan-2-yl-pyrazolo[1,5-a][1,3,5]triazin-4-ylamine, 2-[4-(2-Chloro-6-methyl-quinolin-3-ylmethyl)-piperazin-1-yl]-7-furan-2-yl-pyrazolo[1,5-a][1,3,5]triazin-4-ylamine, 7-Furan-2-yl-2-[4-(5-methyl-isoxazol-3-ylmethyl)-[1,4]diazepan-1-yl]-pyrazolo[1,5-a][1,3,5]triazin-4-ylamine, 7-Furan-2-yl-$N^2$-[1-(5-methyl-isoxazol-3-ylmethyl)-pyrrolidin-2-ylmethyl]-pyrazolo[1,5-a][1,3,5]triazine-2,4-diamine, 2-Furan-2-yl-$N^5$-methyl-$N^5$-{2-[methyl-(5-methyl-isoxazol-3-ylmethyl)-amino]-ethyl}-[1,2,4]triazolo[1,5-a][1,3,5]triazine-5,7-diamine, 2-Furan-2-yl-$N^5$-{2-[methyl-(5-methyl-isoxazol-3-ylmethyl)-amino]-ethyl}-[1,2,4]triazolo[1,5-a][1,3,5]triazine-5,7-diamine, 2-Furan-2-yl-$N^5$-[1-(5-methyl-isoxazol-3-ylmethyl)-piperidin-3-ylmethyl]-[1,2,4]triazolo[1,5-a][1,3,5]triazine-5,7-diamine, 2-Furan-2-yl-$N^5$-methyl-$N^5$-[1-(5-methyl-isoxazol-3-ylmethyl)-pyrrolidin-2-ylmethyl]-[1,2,4]triazolo[1,5-a][1,3,5]triazine-5,7-diamine, $N^5$-(1-Benzyl-piperidin-4-yl)-2-furan-2-yl-[1,2,4]triazolo[1,5-a][1,3,5]triazine-5,7-diamine, $N^5$-(1-Benzyl-pyrrolidin-3-yl)-2-furan-2-yl-[1,2,4]triazolo[1,5-a][1,3,5]triazine-5,7-diamine, 2-Furan-2-yl-$N^5$-[1-(5-methyl-isoxazol-3-ylmethyl)-pyrrolidin-3-yl]-[1,2,4]triazolo[1,5-a][1,3,5]triazine-5,7-diamine, 2-Furan-2-yl-5-(4-pyridin-3-ylmethyl-piperazin-1-yl)-[1,2,4]triazolo[1,5-a][1,3,5]triazin-7-ylamine, 2-Furan-2-yl-5-(4-pyridin-4-ylmethyl-piperazin-1-yl)-[1,2,4]triazolo[1,5-a][1,3,5]triazin-7-ylamine, 2-Furan-2-yl-$N^5$-[1-(5-methyl-isoxazol-3-ylmethyl)-pyrrolidin-2-ylmethyl]-[1,2,4]triazolo[1,5-a][1,3,5]triazine-5,7-diamine, 2-Furan-2-yl-$N^5$-{2-[(5-methyl-isoxazol-3-ylmethyl)-amino]-ethyl}-[1,2,4]triazolo[1,5-a][1,3,5]triazine-5,7-diamine, 2-Furan-2-yl-5-[4-(1H-imidazol-2-ylmethyl)-piperazin-1-yl]-[1,2,4]triazolo[1,5-a][1,3,5]triazin-7-ylamine, 2-Furan-2-yl-5-[4-(1-methyl-1H-imidazol-2-ylmethyl)-piperazin-1-yl]-[1,2,4]triazolo[1,5-a][1,3,5]triazin-7-ylamine, 5-[4-(5-Chloro-thiophen-2-ylmethyl)-piperazin-1-yl]-2-furan-2-yl-[1,2,4]triazolo[1,5-a][1,3,5]triazin-7-ylamine, 2-Furan-2-yl-5-[4-(1H-imidazol-4-ylmethyl)-piperazin-1-yl]-[1,2,4]triazolo[1,5-a][1,3,5]triazin-7-ylamine, 2-Furan-2-yl-5-[4-(1H-pyrrol-2-ylmethyl)-piperazin-1-yl]-[1,2,4]triazolo[1,5-a][1,3,5]triazin-7-ylamine, 2-Furan-2-yl-$N^5$-[1-(5-methyl-isoxazol-3-ylmethyl)-piperidin-4-ylmethyl]-[1,2,4]triazolo[1,5-a][1,3,5]triazine-5,7-diamine, 2-Furan-2-yl-$N^5$-[1-(5-methyl-isoxazol-3-ylmethyl)-piperidin-3-yl]-[1,2,4]triazolo[1,5-a][1,3,5]triazine-5,7-diamine, 2-Furan-2-yl-N$^5$-methyl-N$^5$-{2-[methyl-(5-methyl-isoxazol-3-ylmethyl)-amino]-cyclohexyl}-[1,2,4]triazolo[1,5-a][1,3,5]triazine-5,7-diamine, 2-Furan-2-yl-N$^5$-{3-[(5-methyl-isoxazol-3-ylmethyl)-amino]-propyl}-[1,2,4]triazolo[1,5-a][1,3,5]triazine-5,7-diamine, N$^5$-{2,2-Dimethyl-3-[(5-methyl-isoxazol-3-ylmethyl)-amino]-propyl}-2-furan-2-yl-[1,2,4]triazolo[1,5-a][1,3,5]triazine-5,7-diamine, 2-Furan-2-yl-N$^5$-[1-(5-methyl-isoxazol-3-ylmethyl)-piperidin-4-yl]-[1,2,4]triazolo[1,5-a][1,3,5]triazine-5,7-diamine, 2-Furan-2-yl-N$^5$-[1-(5-methyl-isoxazol-3-ylmethyl)-pyrrolidin-2-ylmethyl]-[1,2,4]triazolo[1,5-a][1,3,5]triazine-5,7-diamine, 2-Furan-2-yl-5-(4-quinolin-4-ylmethyl-piperazin-1-yl)-[1,2,4]triazolo[1,5-a][1,3,5]triazin-7-ylamine, 2-Furan-2-yl-5-[4-(5-methyl-3H-imidazol-4-ylmethyl)-piperazin-1-yl]-[1,2,4]triazolo[1,5-a][1,3,5]triazin-7-ylamine, 2-Furan-2-yl-5-(4-furan-2-ylmethyl-piperazin-1-yl)-[1,2,4]triazolo[1,5-a][1,3,5]triazin-7-ylamine, 2-Furan-2-yl-5-(4-quinolin-2-ylmethyl-piperazin-1-yl)-[1,2,4]triazolo[1,5-a][1,3,5]triazin-7-ylamine, 2-Furan-2-yl-N$^5$-methyl-N$^5$-[1-(5-methyl-isoxazol-3-ylmethyl)-pyrrolidin-2-ylmethyl]-[1,2,4]triazolo[1,5-a][1,3,5]triazine-5,7-diamine, 2-Furan-2-yl-5-[4-(3-phenyl-propyl)-[1,4]diazepan-1-yl]-[1,2,4]triazolo[1,5-a][1,3,5]triazin-7-ylamine, 5-[4-(2,6-Dichloro-benzyl)-[1,4]diazepan-1-yl]-2-furan-2-yl-[1,2,4]triazolo[1,5-a][1,3,5]triazin-7-ylamine, 2-Furan-2-yl-5-[4-(5-methyl-isoxazol-3-ylmethyl)-[1,4]diazepan-1-yl]-[1,2,4]triazolo[1,5-a][1,3,5]triazin-7-ylamine, 2-Furan-2-yl-5-(4-pyridin-3-ylmethyl-[1,4]diazepan-1-yl)-[1,2,4]triazolo[1,5-a][1,3,5]triazin-7-ylamine, 2-Furan-2-yl-5-(4-pyridin-4-ylmethyl-[1,4]diazepan-1-yl)-[1,2,4]triazolo[1,5-a][1,3,5]triazin-7-ylamine, 2-Furan-2-yl-5-(4-quinolin-4-ylmethyl-[1,4]diazepan-1-yl)-[1,2,4]triazolo[1,5-a][1,3,5]triazin-7-ylamine, 2-Furan-2-yl-5-(4-quinolin-2-ylmethyl-[1,4]diazepan-1-yl)-[1,2,4]triazolo[1,5-a][1,3,5]triazin-7-ylamine, 2-Furan-2-yl-5-(4-furan-2-ylmethyl-[1,4]diazepan-1-yl)-[1,2,4]triazolo[1,5-a][1,3,5]triazin-7-ylamine, 2-[(7-Amino-2-furan-2-yl-[1,2,4]triazolo[1,5-a][1,3,5]triazin-5-ylamino)-methyl]-pyrrolidine-1-carboxylic acid tert-butyl ester, 2-(3-Fluoro-phenyl)-5-[4-(5-methyl-isoxazol-3-ylmethyl)-piperazin-1-yl]-[1,2,4]triazolo[1,5-a][1,3,5]triazin-7-ylamine, 2-Furan-2-yl-5-[4-(5-methyl-isoxazol-4-ylmethyl)-piperazin-1-yl]-[1,2,4]triazolo[1,5-a][1,3,5]triazin-7-ylamine, 2-Furan-2-yl-5-[4-(5-methyl-isoxazol-4-ylmethyl)-piperazin-1-yl]-[1,2,4]triazolo[1,5-a][1,3,5]triazin-7-ylamine, 2-(3-Fluoro-phenyl)-5-[4-(5-methyl-isoxazol-4-ylmethyl)-[1,4]diazepan-1-yl]-[1,2,4]triazolo[1,5-a][1,3,5]triazin-7-ylamine, 2-(3-Fluoro-phenyl)-5-[4-(5-methyl-isoxazol-3-ylmethyl)-[1,4]diazepan-1-yl]-[1,2,4]triazolo[1,5-a][1,3,5]triazin-7-ylamine, 2-(3-Fluoro-phenyl)-N$^5$-[1-(5-methyl-isoxazol-3-ylmethyl)-pyrrolidin-2-ylmethyl]-[1,2,4]triazolo[1,5-a][1,3,5]triazine-5,7-diamine, 5-[4-(5-Chloro-furan-2-ylmethyl)-piperazin-1-yl]-2-furan-2-yl-[1,2,4]triazolo[1,5-a][1,3,5]triazin-7-ylamine, 5-[4-(6-Bromo-pyridin-2-ylmethyl)-piperazin-1-yl]-2-furan-2-yl-[1,2,4]triazolo[1,5-a][1,3,5]triazin-7-ylamine, 5-[4-(2-Chloro-8-methyl-quinolin-3-ylmethyl)-piperazin-1-yl]-2-furan-2-yl-[1,2,4]triazolo[1,5-a][1,3,5]triazin-7-ylamine, 5-[4-(2-Chloro-6-methyl-quinolin-3-ylmethyl)-piperazin-1-yl]-2-furan-2-yl-[1,2,4]triazolo[1,5-a][1,3,5]triazin-7-ylamine, 2-Furan-2-yl-5-(4-quinolin-3-ylmethyl-piperazin-1-yl)-[1,2,4]triazolo[1,5-a][1,3,5]triazin-7-ylamine, 2-Furan-2-yl-5-[4-(5-methyl-furan-2-ylmethyl)-piperazin-1-yl]-[1,2,4]triazolo[1,5-a][1,3,5]triazin-7-ylamine, {5-[4-(7-Amino-2-furan-2-yl-[1,2,4]triazolo[1,5-a][1,3,5]triazin-5-yl)-piperazin-1-ylmethyl]-furan-2-yl}-methanol, 5-[4-(3,5-Dimethyl-isoxazol-4-ylmethyl)-[1,4]diazepan-1-yl]-2-furan-2-yl-[1,2,4]triazolo[1,5-a][1,3,5]triazin-7-ylamine, 2-Furan-2-yl-5-(4-quinolin-3-ylmethyl-[1,4]diazepan-1-yl)-[1,2,4]triazolo[1,5-a][1,3,5]triazin-7-ylamine, 2-Furan-2-yl-5-[4-(2-methyl-furan-3-ylmethyl)-[1,4]diazepan-1-yl]-[1,2,4]triazolo[1,5-a][1,3,5]triazin-7-ylamine, 2-Furan-2-yl-5-[4-(2-methyl-furan-3-ylmethyl)-piperazin-1-yl]-[1,2,4]triazolo[1,5-a][1,3,5]triazin-7-ylamine, N$^5$-[1-(3-Chloro-benzyl)-pyrrolidin-2-ylmethyl]-2-furan-2-yl-[1,2,4]triazolo[1,5-a][1,3,5]triazine-5,7-diamine, 2-Furan-2-yl-5-[4-(3-methyl-thiophen-2-ylmethyl)-[1,4]diazepan-1-yl]-[1,2,4]triazolo[1,5-a][1,3,5]triazin-7-ylamine, 2-Furan-2-yl-5-[4-(1-methyl-1H-imidazol-2-ylmethyl)-[1,4]diazepan-1-yl]-[1,2,4]triazolo[1,5-a][1,3,5]triazin-7-ylamine, N$^5$-[1-(4-Chloro-benzyl)-pyrrolidin-2-ylmethyl]-2-furan-2-yl-[1,2,4]triazolo[1,5-a][1,3,5]triazine-5,7-diamine, 5-[4-(6-Bromo-pyridin-2-ylmethyl)-[1,4]diazepan-1-yl]-2-furan-2-yl-[1,2,4]triazolo[1,5-a][1,3,5]triazin-7-ylamine, 2-Furan-2-yl-N$^5$-(1-pyridin-3-ylmethyl-pyrrolidin-2-ylmethyl)-[1,2,4]triazolo[1,5-a][1,3,5]triazine-5,7-diamine, 5-[4-(5-Chloro-furan-2-ylmethyl)-[1,4]diazepan-1-yl]-2-furan-2-yl-[1,2,4]triazolo[1,5-a][1,3,5]triazin-7-ylamine, 2-Furan-2-yl-N$^5$-(1-pyridin-4-ylmethyl-pyrrolidin-2-ylmethyl)-[1,2,4]triazolo[1,5-a][1,3,5]triazine-5,7-diamine, 5-[4-(3-Chloro-2,6-difluoro-benzyl)-[1,4]diazepan-1-yl]-2-furan-2-yl-[1,2,4]triazolo[1,5-a][1,3,5]triazin-7-ylamine, 5-[4-(6-Chloro-2-fluoro-3-methyl-benzyl)-[1,4]diazepan-1-yl]-2-furan-2-yl-[1,2,4]triazolo[1,5-a][1,3,5]triazin-7-ylamine, 5-[4-(2-Chloro-6-fluoro-3-methyl-benzyl)-[1,4]diazepan-1-yl]-2-furan-2-yl-[1,2,4]triazolo[1,5-a][1,3,5]triazin-7-ylamine, 5-[4-(2-Chloro-8-methyl-quinolin-3-ylmethyl)-[1,4]diazepan-1-yl]-2-furan-2-yl-[1,2,4]triazolo[1,5-a][1,3,5]triazin-7-ylamine, 5-[4-(2-Chloro-6-methyl-quinolin-3-ylmethyl)-[1,4]diazepan-1-yl]-2-furan-2-yl-[1,2,4]triazolo[1,5-a][1,3,5]triazin-7-ylamine, N$^5$-[1-(2-Bromo-benzyl)-pyrrolidin-2-ylmethyl]-2-furan-2-yl-[1,2,4]triazolo[1,5-a][1,3,5]triazine-5,7-diamine, $N^5$-[1-(2-Fluoro-benzyl)-pyrrolidin-2-ylmethyl]-2-furan-2-yl-[1,2,4]triazolo[1,5-a][1,3,5]triazine-5,7-diamine, $N^5$-[1-(2-Chloro-benzyl)-pyrrolidin-2-ylmethyl]-2-furan-2-yl-[1,2,4]triazolo[1,5-a][1,3,5]triazine-5,7-diamine, 2-Furan-2-yl-$N^5$-(1-pyridin-2-ylmethyl-pyrrolidin-2-ylmethyl)-[1,2,4]triazolo[1,5-a][1,3,5]triazine-5,7-diamine, 2-Furan-2-yl-$N^5$-(1-quinolin-2-ylmethyl-pyrrolidin-2-ylmethyl)-[1,2,4]triazolo[1,5-a][1,3,5]triazine-5,7-diamine, 2-Furan-2-yl-$N^5$-(1-furan-2-ylmethyl-pyrrolidin-2-ylmethyl)-[1,2,4]triazolo[1,5-a][1,3,5]triazine-5,7-diamine, 5-[4-(2-Chloro-quinolin-3-ylmethyl)-piperazin-1-yl]-2-furan-2-yl-[1,2,4]triazolo[1,5-a][1,3,5]triazin-7-ylamine, 5-[4-(5-Bromo-furan-2-ylmethyl)-piperazin-1-yl]-2-furan-2-yl-[1,2,4]triazolo[1,5-a][1,3,5]triazin-7-ylamine, 2-Furan-2-yl-5-(4-thiophen-3-ylmethyl-piperazin-1-yl)-[1,2,4]triazolo[1,5-a][1,3,5]triazin-7-ylamine, 2-Furan-2-yl-5-[4-(2-methyl-benzyl)-[1,4]diazepan-1-yl]-[1,2,4]triazolo[1,5-a][1,3,5]triazin-7-ylamine, 2-Furan-2-yl-5-[4-(3-methyl-benzyl)-[1,4]diazepan-1-yl]-[1,2,4]triazolo[1,5-a][1,3,5]triazin-7-ylamine, 2-Furan-2-yl-5-[4-(4-methyl-benzyl)-[1,4]diazepan-1-yl]-[1,2,4]triazolo[1,5-a][1,3,5]triazin-7-ylamine, 5-[4-(3-Chloro-benzyl)-[1,4]diazepan-1-yl]-2-furan-2-yl-[1,2,4]triazolo[1,5-a][1,3,5]triazin-7-ylamine, 5-[4-(4-Chloro-benzyl)-[1,4]diazepan-1-yl]-2-furan-2-yl-[1,2,4]triazolo[1,5-a][1,3,5]triazin-7-ylamine, 5-[4-(2-Bromo-benzyl)-[1,4]diazepan-1-yl]-2-furan-2-yl-[1,2,4]triazolo[1,5-a][1,3,5]triazin-7-ylamine, 5-[4-(3-Bromo-benzyl)-[1,4]diazepan-1-yl]-2-furan-2-yl-[1,2,4]triazolo[1,5-a][1,3,5]triazin-7-ylamine, 5-[4-(4-Bromo-benzyl)-[1,4]diazepan-1-yl]-2-furan-2-yl-[1,2,4]triazolo[1,5-a][1,3,5]triazin-7-ylamine, 5-[4-(2-Fluoro-benzyl)-[1,4]diazepan-1-yl]-2-furan-2-yl-[1,2,4]triazolo[1,5-a][1,3,5]triazin-7-ylamine, $N^5$-[1-(6-Chloro-2-fluoro-3-methyl-benzyl)-pyrrolidin-2-ylmethyl]-2-furan-2-yl-[1,2,4]triazolo[1,5-a][1,3,5]triazine-5,7-diamine, $N^5$-[1-(3-Chloro-2,6-difluoro-benzyl)-pyrrolidin-2-ylmethyl]-2-furan-2-yl-[1,2,4]triazolo[1,5-a][1,3,5]triazine-5,7-diamine, $N^5$-[1-(2-Chloro-3,6-difluoro-benzyl)-pyrrolidin-2-ylmethyl]-2-furan-2-yl-[1,2,4]triazolo[1,5-a][1,3,5]triazine-5,7-diamine, 2-Furan-2-yl-5-[4-(2-methylsulfanyl-thiophen-3-ylmethyl)-piperazin-1-yl]-[1,2,4]triazolo[1,5-a][1,3,5]triazin-7-ylamine, 5-[4-(5-Chloro-2-phenyl-1H-imidazol-4-ylmethyl)-piperazin-1-yl]-2-furan-2-yl-[1,2,4]triazolo[1,5-a][1,3,5]triazin-7-ylamine, 5-[4-(5-Chloro-1-methyl-3-trifluoromethyl-1H-pyrazol-4-ylmethyl)-piperazin-1-yl]-2-furan-2-yl-[1,2,4]triazolo[1,5-a][1,3,5]triazin-7-ylamine, 5-[4-(4-Chloro-1-methyl-1H-pyrazol-3-ylmethyl)-piperazin-1-yl]-2-furan-2-yl-[1,2,4]triazolo[1,5-a][1,3,5]triazin-7-ylamine, 5-[4-(4-Bromo-1-methyl-1H-pyrazol-3-ylmethyl)-piperazin-1-yl]-2-furan-2-yl-[1,2,4]triazolo[1,5-a][1,3,5]triazin-7-ylamine, 5-[4-(4-Bromo-1H-pyrazol-3-ylmethyl)-piperazin-1-yl]-2-furan-2-yl-[1,2,4]triazolo[1,5-a][1,3,5]triazin-7-ylamine, 2-Furan-2-yl-5-[4-(2-methyl-1H-imidazol-4-ylmethyl)-piperazin-1-yl]-[1,2,4]triazolo[1,5-a][1,3,5]triazin-7-ylamine, 5-[4-(2-Ethyl-5-methyl-3H-imidazol-4-ylmethyl)-piperazin-1-yl]-2-furan-2-yl-[1,2,4]triazolo[1,5-a][1,3,5]triazin-7-ylamine, 2-Furan-2-yl-5-[4-(2-phenyl-1H-imidazol-4-ylmethyl)-piperazin-1-yl]-[1,2,4]triazolo[1,5-a][1,3,5]triazin-7-ylamine, 2-Furan-2-yl-5-(4-[1,2,3]thiadiazol-4-ylmethyl-piperazin-1-yl)-[1,2,4]triazolo[1,5-a][1,3,5]triazin-7-ylamine, 2-Furan-2-yl-$N^5$-[1-(2-methyl-benzyl)-pyrrolidin-2-ylmethyl]-[1,2,4]triazolo[1,5-a][1,3,5]triazine-5,7-diamine, 2-Furan-2-yl-$N^5$-[1-(3-methyl-benzyl)-pyrrolidin-2-ylmethyl]-[1,2,4]triazolo[1,5-a][1,3,5]triazine-5,7-diamine, $N^5$-[1-(2-Chloro-6-fluoro-3-methyl-benzyl)-pyrrolidin-2-ylmethyl]-2-furan-2-yl-[1,2,4]triazolo[1,5-a][1,3,5]triazine-5,7-diamine, $N^5$-[1-(2,6-Difluoro-benzyl)-pyrrolidin-2-ylmethyl]-2-furan-2-yl-[1,2,4]triazolo[1,5-a][1,3,5]triazine-5,7-diamine,

[2-(7-Amino-2-furan-2-yl-[1,2,4]triazolo[1,5-a][1,3,5]triazin-5-ylamino)-ethyl]-methyl-carbamic acid tert-butyl ester, $N^5$-[1-(2,5-Difluoro-benzyl)-pyrrolidin-2-ylmethyl]-2-furan-2-yl-[1,2,4]triazolo[1,5-a][1,3,5]triazine-5,7-diamine, $N^5$-[1-(3,4-Dichloro-benzyl)-pyrrolidin-2-ylmethyl]-2-furan-2-yl-[1,2,4]triazolo[1,5-a][1,3,5]triazine-5,7-diamine, $N^5$-[1-(3-Fluoro-benzyl)-pyrrolidin-2-ylmethyl]-2-furan-2-yl-[1,2,4]triazolo[1,5-a][1,3,5]triazine-5,7-diamine, $N^5$-[1-(2,3-Difluoro-benzyl)-pyrrolidin-2-ylmethyl]-2-furan-2-yl-[1,2,4]triazolo[1,5-a][1,3,5]triazine-5,7-diamine, $N^5$-[1-(2,4-Difluoro-benzyl)-pyrrolidin-2-ylmethyl]-2-furan-2-yl-[1,2,4]triazolo[1,5-a][1,3,5]triazine-5,7-diamine, 2-Furan-2-yl-$N^5$-[1-(4-methyl-benzyl)-pyrrolidin-2-ylmethyl]-[1,2,4]triazolo[1,5-a][1,3,5]triazine-5,7-diamine, $N^5$-[1-(3,5-Dichloro-benzyl)-pyrrolidin-2-ylmethyl]-2-furan-2-yl-[1,2,4]triazolo[1,5-a][1,3,5]triazine-5,7-diamine, $N^5$-[1-(3,5-Difluoro-benzyl)-pyrrolidin-2-ylmethyl]-2-furan-2-yl-[1,2,4]triazolo[1,5-a][1,3,5]triazine-5,7-diamine, 2-{[(7-Amino-2-furan-2-yl-[1,2,4]triazolo[1,5-a][1,3,5]triazin-5-yl)-methyl-amino]-methyl}-pyrrolidine-1-carboxylic acid tert-butyl ester, $N^5$-[1-(2,4-Dichloro-benzyl)-pyrrolidin-2-ylmethyl]-2-furan-2-yl-[1,2,4]triazolo[1,5-a][1,3,5]triazine-5,7-diamine, $N^5$-[1-(2,6-Dimethyl-benzyl)-pyrrolidin-2-ylmethyl]-2-furan-2-yl-[1,2,4]triazolo[1,5-a][1,3,5]triazine-5,7-diamine, $N^5$-[1-(2-Chloro-quinolin-3-ylmethyl)-pyrrolidin-2-ylmethyl]-2-furan-2-yl-[1,2,4]triazolo[1,5-a][1,3,5]triazine-5,7-diamine, $N^5$-[1-(5-Chloro-furan-2-ylmethyl)-pyrrolidin-2-ylmethyl]-2-furan-2-yl-[1,2,4]triazolo[1,5-a][1,3,5]triazine-5,7-diamine, 2-Furan-2-yl-N$^5$-[1-(2,3,6-trifluoro-benzyl)-pyrrolidin-2-ylmethyl]-[1,2,4]triazolo[1,5-a][1,3,5]triazine-5,7-diamine,
2-Furan-2-yl-N$^5$-[1-(2,4,6-trifluoro-benzyl)-pyrrolidin-2-ylmethyl]-[1,2,4]triazolo[1,5-a][1,3,5]triazine-5,7-diamine,
2-Furan-2-yl-N$^5$-[1-(2,4,5-trifluoro-benzyl)-pyrrolidin-2-ylmethyl]-[1,2,4]triazolo[1,5-a][1,3,5]triazine-5,7-diamine,
2-[(7-Amino-2-furan-2-yl-[1,2,4]triazolo[1,5-a][1,3,5]triazin-5-ylamino)-methyl]-piperidine-1-carboxylic acid tert-butyl ester,
N$^5$-[1-(3-Chloro-2-fluoro-5-trifluoromethyl-benzyl)-pyrrolidin-2-ylmethyl]-2-furan-2-2-yl-[1,2,4]triazolo[1,5-a][1,3,5]triazine-5,7-diamine,
N$^5$-[1-(4-Chloro-benzyl)-piperidin-3-ylmethyl]-2-furan-2-yl-[1,2,4]triazolo[1,5-a][1,3,5]triazine-5,7-diamine,
N$^5$-[1-(2,6-Difluoro-benzyl)-pyrrolidin-2-ylmethyl]-2-furan-2-yl-N5-methyl-[1,2,4]triazolo[1,5-a][1,3,5]triazine-5,7-diamine,
N$^5$-[1-(2-Chloro-3,6-difluoro-benzyl)-pyrrolidin-2-ylmethyl]-2-furan-2-yl-N5-methyl-[1,2,4]triazolo[1,5-a][1,3,5]triazine-5,7-diamine,
N$^5$-[1-(3-Chloro-2-fluoro-6-trifluoromethyl-benzyl)-pyrrolidin-2-ylmethyl]-2-furan-2-yl-[1,2,4]triazolo[1,5-a][1,3,5]triazine-5,7-diamine,
2-Furan-2-yl-N$^5$-(1-quinolin-3-ylmethyl-pyrrolidin-2-ylmethyl)-[1,2,4]triazolo[1,5-a][1,3,5]triazine-5,7-diamine,
2-Furan-2-yl-N$^5$-[1-(5-methyl-isoxazol-3-ylmethyl)-piperidin-3-ylmethyl]-[1,2,4]triazolo[1,5-a][1,3,5]triazine-5,7-diamine,
N$^5$-[1-(3-Chloro-5-trifluoromethyl-benzyl)-pyrrolidin-2-ylmethyl]-2-furan-2-yl-[1,2,4]triazolo[1,5-a][1,3,5]triazine-5,7-diamine,
N$^5$-[1-(4-Fluoro-3-methyl-benzyl)-pyrrolidin-2-ylmethyl]-2-furan-2-yl-[1,2,4]triazolo[1,5-a][1,3,5]triazine-5,7-diamine,
N$^5$-[1-(2-Bromo-5-fluoro-benzyl)-pyrrolidin-2-ylmethyl]-2-furan-2-yl-[1,2,4]triazolo[1,5-a][1,3,5]triazine-5,7-diamine,
N$^5$-[1-(4-Chloro-3-fluoro-benzyl)-pyrrolidin-2-ylmethyl]-2-furan-2-yl-[1,2,4]triazolo[1,5-a][1,3,5]triazine-5,7-diamine,
N$^5$-[1-(2-Fluoro-benzyl)-pyrrolidin-2-ylmethyl]-2-furan-2-yl-N$^5$-methyl-[1,2,4]triazolo[1,5-a][1,3,5]triazine-5,7-diamine,
N$^5$-[1-(3-Chloro-2-fluoro-benzyl)-pyrrolidin-2-ylmethyl]-2-furan-2-yl-[1,2,4]triazolo[1,5-a][1,3,5]triazine-5,7-diamine,
N$^5$-[1-(2-Fluoro-5-trifluoromethyl-benzyl)-pyrrolidin-2-ylmethyl]-2-furan-2-yl-[1,2,4]triazolo[1,5-a][1,3,5]triazine-5,7-diamine,
N$^5$-[1-(2-Fluoro-4-trifluoromethyl-benzyl)-pyrrolidin-2-ylmethyl]-2-furan-2-yl-[1,2,4]triazolo[1,5-a][1,3,5]triazine-5,7-diamine,
2-Furan-2-yl-N$^5$-(1-quinolin-4-ylmethyl-pyrrolidin-2-ylmethyl)-[1,2,4]triazolo[1,5-a][1,3,5]triazine-5,7-diamine,
2-(3-Fluoro-phenyl)-5-(4-quinolin-2-ylmethyl-piperazin-1-yl)-[1,2,4]triazolo[1,5-a][1,3,5]triazin-7-ylamine,
2-(3-Fluoro-phenyl)-5-(4-quinolin-3-ylmethyl-piperazin-1-yl)-[1,2,4]triazolo[1,5-a][1,3,5]triazin-7-ylamine,
2-(3-Fluoro-phenyl)-5-(4-quinolin-4-ylmethyl-piperazin-1-yl)-[1,2,4]triazolo[1,5-a][1,3,5]triazin-7-ylamine,
2-(3-Fluoro-phenyl)-5-(4-pyridin-2-ylmethyl-piperazin-1-yl)-[1,2,4]triazolo[1,5-a][1,3,5]triazin-7-ylamine,
2-(3-Fluoro-phenyl)-5-(4-pyridin-3-ylmethyl-piperazin-1-yl)-[1,2,4]triazolo[1,5-a][1,3,5]triazin-7-ylamine,
2-(3-Fluoro-phenyl)-5-(4-pyridin-4-ylmethyl-piperazin-1-yl)-[1,2,4]triazolo[1,5-a][1,3,5]triazin-7-ylamine,
N$^5$-[1-(3,5-Difluoro-benzyl)-pyrrolidin-2-ylmethyl]-2-furan-2-yl-N5-methyl-[1,2,4]triazolo[1,5-a][1,3,5]triazine-5,7-diamine,
N$^5$-[1-(3-Chloro-2,6-difluoro-benzyl)-pyrrolidin-2-ylmethyl]-2-furan-2-yl-N5-methyl-[1,2,4]triazolo[1,5-a][1,3,5]triazine-5,7-diamine,
N$^5$-[1-(3-Fluoro-benzyl)-pyrrolidin-2-ylmethyl]-2-furan-2-yl-N$^5$-methyl-[1,2,4]triazolo[1,5-a][1,3,5]triazine-5,7-diamine,
2-Furan-2-yl-N$^5$-methyl-N5-[1-(2,3,6-trifluoro-benzyl)-pyrrolidin-2-ylmethyl]-[1,2,4]triazolo[1,5-a][1,3,5]triazine-5,7-diamine,
N$^5$-[1-(2,3-Difluoro-benzyl)-piperidin-3-ylmethyl]-2-furan-2-yl-[1,2,4]triazolo[1,5-a][1,3,5]triazine-5,7-diamine,
2-Furan-2-yl-N$^5$-(1-quinolin-2-ylmethyl-piperidin-3-ylmethyl)-[1,2,4]triazolo[1,5-a][1,3,5]triazine-5,7-diamine,
5-(4-Benzofuran-2-ylmethyl-piperazin-1-yl)-2-furan-2-yl-[1,2,4]triazolo[1,5-a][1,3,5]triazin-7-ylamine,
2-Furan-2-yl-5-(4-thiazol-2-ylmethyl-piperazin-1-yl)-[1,2,4]triazolo[1,5-a][1,3,5]triazin-7-ylamine,
2-Furan-2-yl-5-[4-(1H-indol-5-ylmethyl)-piperazin-1-yl]-[1,2,4]triazolo[1,5-a][1,3,5]triazin-7-ylamine,
2-Furan-2-yl-5-[4-(1-methyl-1H-indol-2-ylmethyl)-piperazin-1-yl]-[1,2,4]triazolo[1,5-a][1,3,5]triazin-7-ylamine,
2-Furan-2-yl-5-[4-(6-methyl-pyridin-2-ylmethyl)-piperazin-1-yl]-[1,2,4]triazolo[1,5-a][1,3,5]triazin-7-ylamine,
5-[4-(2-Chloro-6-methoxy-quinolin-3-ylmethyl)-piperazin-1-yl]-2-furan-2-yl-[1,2,4]triazolo[1,5-a][1,3,5]triazin-7-ylamine,
2-Furan-2-yl-5-[4-(5-methyl-1H-indol-2-ylmethyl)-piperazin-1-yl]-[1,2,4]triazolo[1,5-a][1,3,5]triazin-7-ylamine,
5-[4-(5-Chloro-1H-indol-2-ylmethyl)-piperazin-1-yl]-2-furan-2-yl-[1,2,4]triazolo[1,5-a][1,3,5]triazin-7-ylamine,
N$^5$-(1-Benzofuran-2-ylmethyl-pyrrolidin-2-ylmethyl)-2-furan-2-yl-[1,2,4]triazolo[1,5-a][1,3,5]triazine-5,7-diamine,
N$^5$-[1-(4-Chloro-1-methyl-1H-pyrazol-3-ylmethyl)-pyrrolidin-2-ylmethyl]-2-furan-2-yl-[1,2,4]triazolo[1,5-a][1,3,5]triazine-5,7-diamine,
N$^5$-[1-(4-Bromo-1-methyl-1H-pyrazol-3-ylmethyl)-pyrrolidin-2-ylmethyl]-2-furan-2-yl-[1,2,4]triazolo[1,5-a][1,3,5]triazine-5,7-diamine,
2-[(7-Amino-2-furan-2-yl-[1,2,4]triazolo[1,5-a][1,3,5]triazin-5-ylamino)-methyl]-piperidine-1-carboxylic acid tert-butyl ester,
N$^5$-[1-(3,5-Dichloro-pyridin-4-ylmethyl)-pyrrolidin-2-ylmethyl]-2-furan-2-yl-[1,2,4]triazolo[1,5-a][1,3,5]triazine-5,7-diamine,
2-Furan-2-yl-5-[4-(2-methyl-pyridin-3-ylmethyl)-piperazin-1-yl]-[1,2,4]triazolo[1,5-a][1,3,5]triazin-7-ylamine,
2-Furan-2-yl-N$^5$-[1-(3-methyl-pyridin-2-ylmethyl)-pyrrolidin-2-ylmethyl]-[1,2,4]triazolo[1,5-a][1,3,5]triazine-5,7-diamine,
5-[4-(2,6-Dichloro-5-fluoro-pyridin-3-ylmethyl)-piperazin-1-yl]-2-furan-2-yl-[1,2,4]triazolo[1,5-a][1,3,5]triazin-7-ylamine, N$^5$-[1-(3,6-Dichloro-5-fluoro-pyridin-2-ylmethyl)-pyrrolidin-2-ylmethyl]-2-furan-2-yl-[1,2,4]triazolo[1,5-a][1,3,5]triazine-5,7-diamine, 5-[4-(2,4-Dimethyl-pyridin-3-ylmethyl)-piperazin-1-yl]-2-furan-2-yl-[1,2,4]triazolo[1,5-a][1,3,5]triazin-7-ylamine, N$^5$-[1-(2,4-Dimethyl-pyridin-3-ylmethyl)-pyrrolidin-2-ylmethyl]-2-furan-2-yl-[1,2,4]triazolo[1,5-a][1,3,5]triazine-5,7-diamine, N$^5$-[1-(2,6-Dichloro-benzyl)-piperidin-2-ylmethyl]-2-furan-2-yl-[1,2,4]triazolo[1,5-a][1,3,5]triazine-5,7-diamine, N$^5$-[1-(2-Chloro-6-fluoro-benzyl)-piperidin-2-ylmethyl]-2-furan-2-yl-[1,2,4]triazolo[1,5-a][1,3,S]triazine-5,7-diamine, N$^5$-[1-(2-Fluoro-benzyl)-piperidin-2-ylmethyl]-2-furan-2-yl-[1,2,4]triazolo[1,5-a][1,3,5]triazine-5,7-diamine, N$^5$-[1-(2-Chloro-benzyl)-piperidin-2-ylmethyl]-2-furan-2-yl-[1,2,4]triazolo[1,5-a][1,3,5]triazine-5,7-diamine, N$^5$-[1-(6-Chloro-pyridin-3-ylmethyl)-piperidin-2-ylmethyl]-2-furan-2-yl-[1,2,4]triazolo[1,5-a][1,3,5]triazine-5,7-diamine, 5-[4-(2-Chloro-pyridin-3-ylmethyl)-piperazin-1-yl]-2-furan-2-yl-[1,2,4]triazolo[1,5-a][1,3,5]triazin-7-ylamine, 5-[4-(2,6-Dichloro-pyridin-4-ylmethyl)-piperazin-1-yl]-2-furan-2-yl-[1,2,4]triazolo[1,5-a][1,3,5]triazin-7-ylamine, 2-Furan-2-yl-5-[4-(4-methyl-pyridin-2-ylethyl)-piperazin-1-yl]-[1,2,4]triazolo[1,5-a][1,3,5]triazin-7-ylamine, N$^5$-[1-(3-Chloro-2-fluoro-4-methyl-benzyl)-pyrrolidin-2-ylmethyl]-2-furan-2-yl-[1,2,4]triazolo[1,5-a][1,3,5]triazine-5,7-diamine, N$^5$-[1-(3-Fluoro-5-methyl-benzyl)-pyrrolidin-2-ylmethyl]-2-furan-2-yl-[1,2,4]triazolo[1,5-a][1,3,5]triazine-5,7-diamine, N$^5$-[1-(3-Fluoro-4-methyl-benzyl)-pyrrolidin-2-ylmethyl]-2-furan-2-yl-[1,2,4]triazol[1,5-a][1,3,5]triazine-5,7-diamine, N$^5$-[1-(2-Bromo-4-fluoro-benzyl)-pyrrolidin-2-ylmethyl]-2-furan-2-yl-[1,2,4]triazolo[1,5-a][1,3,5]triazine-5,7-diamine, 2-Furan-2-yl-N$^5$-methyl-N5-[1-(2,4,6-trifluoro-benzyl)-pyrrolidin-2-ylmethyl]-[1,2,4]triazolo[1,5-a][1,3,5]triazine-5,7-diamine, 2-Furan-2-yl-N$^5$-[1-(5-methyl-4-isoxazol-3-ylmethyl)-piperidin-2-ylmethyl]-[1,2,4]triazolo[1,5-a][1,3,5]triazine-5,7-diamine, 2-Furan-2-yl-N$^5$-(1-quinolin-2-ylmethyl-piperidin-2-ylmethyl)-[1,2,4]triazolo[1,5-a][1,3,5]triazine-5,7-diamine, 2-Furan-2-yl-N$^5$-(1-pyridin-2-ylmethyl-piperidin-2-ylmethyl)-[1,2,4]triazolo[1,5-a][1,3,5]triazine-5,7-diamine, N$^5$-[1-(2,6-Dichloro-5-fluoro-pyridin-3-ylmethyl)-piperidin-2-ylmethyl]-2-furan-2-yl-[1,2,4]triazolo[1,5-a][1,3,5]triazine-5,7-diamine, N$^5$-[1-(3,5-Dichloro-pyridinylmethyl)-piperidin-2-ylmethyl]-2-furan-2-yl-[1,2,4]triazolo[1,5-a][1,3,5]triazine-5,7-diamine, 2-Furan-2-yl-N$^5$-methyl-N5-[1-(5-methyl-isoxazol-3-ylmethyl)-piperidin-2-ylmethyl]-[1,2,4]triazolo[1,5-a][1,3,5]triazine-5,7-diamine, N$^2$-(1-Benzyl-pyrrolidin-3-yl)-7-furan-2-yl-pyrazolo[1,5-a][1,3,5]triazine-2,4-diamine, N$^2$-(1-Benzyl-piperidin-4-yl)-7-furan-2-yl-pyrazolo[1,5-a][1,3,5]triazine-2,4-diamine, 7-Furan-2-yl-N$^2$-[1-(5-methyl-isoxazol-3-ylmethyl)-pyrrolidin-3-yl]-pyrazolo[1,5-a][1,3,5]triazine-2,4-diamine, 7-Furan-2-yl-N$^2$-[1-(5-methyl-isoxazol-3-ylmethyl)-pyrrolidin-2-ylmethyl]-pyrazolo[1,5-a][1,3,5]triazine-2,4-diamine, 7-Furan-2-yl-N$^2$-methyl-N2-[1-(5-methyl-isoxazol-3-ylmethyl)-pyrrolidin-2-ylmethyl]-pyrazolo[1,5-a][1,3,5]triazine-2,4-diamine, 7-Furan-2-yl-2-[4-(5-methyl-isoxazol-3-ylmethyl)-piperazin-1-yl]-pyrazolo[1,5-a][1,3,5]triazin-4-ylamine, 2-[4-(3,5-Dimethyl-isoxazol-4-ylmethyl)-[1,4]diazepan-1-yl]-7-furan-2-yl-pyrazolo[1,5-a][1,3,5]triazin-4-ylamine, N$^5$-[1-(3-Chloro-1-methyl-1H-pyrazol-4-ylmethyl)-pyrrolidin-2-ylmethyl]-2-furan-2-yl-[1,2,4]triazolo[1,5-a][1,3,5]triazine-5,7-diamine, N$^5$-[1-(2-Chloro-pyridin-4-ylmethyl)-pyrrolidin-2-ylmethyl]-2-furan-2-yl-[1,2,4]triazolo[1,5-a][1,3,5]triazine-5,7-diamine, N$^5$-{2-[4-(2,4-Difluoro-phenyl)-piperazin-1-yl]-ethyl}-2-furan-2-yl-[1,2,4]triazolo[1,5-a][1,3,5]triazine-5,7-diamine, 2-Furan-2-yl-N$^5$-{2-[4-(2,4,6-trifluoro-phenyl)-piperazin-1-yl]-ethyl}-[1,2,4]triazolo[1,5-a][1,3,5]triazine-5,7-diamine, N$^5$-{2-[4-(2,4-Difluoro-phenyl)-piperazin-1-yl]-ethyl}-2-furan-2-yl-N$^5$-methyl-[1,2,4]triazolo[1,5-a][1,3,5]triazine-5,7-diamine, and 2-Furan-2-yl-N$^5$-methyl-N$^5$-{2-[4-(2,4,6-trifluoro-phenyl)-piperazin-1-yl]-ethyl}-[1,2,4]triazolo[1,5-a][1,3,5]triazine-5,7-diamine.

26. A compound selected from the group consisting of:

2-Furan-2-yl-5-[4-(5-methyl-isoxazol-3-ylmethyl)-piperazin-1-yl]-[1,2,4]triazolo[1,5-a][1,3,5]triazin-7-ylamine, 2-Furan-2-yl-5-(4-pyridin-2-ylmethyl-piperazin-1-yl)-[1,2,4]triazolo[1,5-a][1,3,5]triazin-7-ylamine, 2-Furan-2-yl-5-(4-pyridin-4-ylmethyl-piperazin-1-yl)-[1,2,4]triazolo[1,5-a][1,3,5]triazin-7-ylamine, 2-Furan-2-yl-5-(4-pyridin-3-ylmethyl-piperazin-1-yl)-[1,2,4]triazolo[1,5-a][1,3,5]triazin-7-ylamine, 2-Furan-2-yl-5-[4-(1H-imidazol-4-ylmethyl)-piperazin-1-yl]-[1,2,4]triazolo[1,5-a][1,3,5]triazin-7-ylamine, 2-Furan-2-yl-5-(4-quinolin-4-ylmethyl-piperazin-1-yl)-[1,2,4]triazolo[1,5-a][1,3,5]triazin-7-ylamine, 2-Furan-2-yl-5-(4-furan-2-ylmethyl-piperazin-1-yl)-[1,2,4]triazolo[1,5-a][1,3,5]triazin-7-ylamine, 2-Furan-2-yl-5-(4-quinolin-2-ylethyl-piperazin-1-yl)-[1,2,4]triazolo[1,5-a][1,3,5]triazin-7-ylamine, 5-[4-(3,5-Dimethyl-isoxazol-4-ylmethyl)-piperazin-1-yl]-2-furan-2-yl-[1,2,4]triazolo[1,5-a][1,3,5]triazin-7-ylamine, 5-[4-(2-Chloro-6-methyl-quinolin-3-ylmethyl)-piperazin-1-yl]-2-furan-2-yl-[1,2,4]triazolo[1,5-a][1,3,5]triazin-7-ylamine, 5-[4-(2-Chloro-quinolin-3-ylmethyl)-piperazin-1-yl]-2-furan-2-yl-[1,2,4]triazolo[1,5-a][1,3,5]triazin-7-ylamine, 5-[4-(5-Chloro-1-methyl-3-trifluoromethyl-1H-pyrazol-4-ylmethyl)-piperazin-1-yl]-2-furan-2-yl-[1,2,4]triazolo[1,5-a][1,3,5]triazin-7-ylamine, 5-[4-(4-Chloro-1-methyl-1H-pyrazol-3-ylmethyl)-piperazin-1-yl]-2-furan-2-yl-[1,2,4]triazolo[1,5-a][1,3,5]triazin-7-ylamine, 5-[4-(4-Bromo-1-methyl-1H-pyrazol-3-ylmethyl)-piperazin-1-yl]-2-furan-2-yl-[1,2,4]triazolo[1,5-a][1,3,5]triazin-7-ylamine, 5-(4-Benzofuran-2-ylmethyl-piperazin-1-yl)-2-furan-2-yl-[1,2,4]triazolo[1,5-a][1,3,5]triazin-7-ylamine, 2-Furan-2-yl-5-(4-thiazol-2-ylmethyl-piperazin-1-yl)-[1,2,4]triazolo[1,5-a][1,3,5]triazin-7-ylamine, 5-[4-(3,5-Dichloro-pyridin-4-ylmethyl)-piperazin-1-yl]-2-furan-2-yl-[1,2,4]triazolo[1,5-a][1,3,5]triazin-7-ylamine, 5-[4-(2,4-Dimethyl-pyridin-3-ylmethyl)-piperazin-1-yl]-2-furan-2-yl-[1,2,4]triazolo[1,5-a][1,3,5]triazin-7-ylamine, $N^5$-[1-(2,3-Difluoro-benzyl)-pyrrolidin-2-ylmethyl]-2-furan-2-yl-[1,2,4]triazolo[1,5-a][1,3,5]triazine-5,7-diamine, $N^5$-[1-(2,6-Difluoro-benzyl)-pyrrolidin-2-ylmethyl]-2-furan-2-yl-[1,2,4]triazolo[1,5-a][1,3,5]triazine-5,7-diamine, 2-Furan-2-yl-$N^5$-[1-(2,4,6-trifluoro-benzyl)-pyrrolidin-2-ylmethyl]-[1,2,4]triazolo[1,5-a][1,3,5]triazine-5,7-diamine, $N^5$-[1-(2-Chloro-3,6-difluoro-benzyl)-pyrrolidin-2-ylmethyl]-2-furan-2-yl-[1,2,4]triazolo[1,5-a][1,3,5]triazine-5,7-diamine, $N^5$-[1-(2-Fluoro-5-trifluoromethyl-benzyl)-pyrrolidin-2-ylmethyl]-2-furan-2-yl-[1,2,4]triazolo[1,5-a][1,3,5]triazine-5,7-diamine, $N^5$-[1-(2-Fluoro-4-trifluoromethyl-benzyl)-pyrrolidin-2-ylmethyl]-2-furan-2-yl-[1,2,4]triazolo[1,5-a][1,3,5]triazine-5,7-diamine, 2-Furan-2-yl-$N^5$-[1-(5-methyl-isoxazol-3-ylmethyl)-pyrrolidin-2-ylmethyl]-[1,2,4]triazolo[1,5-a][1,3,5]triazine-5,7-diamine, $N^5$-[1-(5-Chloro-furan-2-ylmethyl)-pyrrolidin-2-ylmethyl]-2-furan-2-yl-[1,2,4]triazolo[1,5-a][1,3,5]triazine-5,7-diamine, $N^5$-[1-(3-Chloro-1-methyl-1H-pyrazol-4-ylmethyl)-pyrrolidin-2-ylmethyl]-2-furan-2-yl-[1,2,4]triazolo[1,5-a][1,3,5]triazine-5,7-diamine, $N^5$-[1-(2-Chloro-pyridin-4-ylmethyl)-pyrrolidin-2-ylmethyl]-2-furan-2-yl-[1,2,4]triazolo[1,5-a][1,3,5]triazine-5,7-diamine, $N^5$-(1-Benzofuran-2-ylmethyl-pyrrolidin-2-ylmethyl)-2-furan-2-yl-[1,2,4]triazolo[1,5-a][1,3,5]triazine-5,7-diamine, $N^5$-{2-[4-(2,4-Difluoro-phenyl)-piperazin-1-yl]-ethyl}-2-furan-2-yl-[1,2,4]triazolo[1,5-a][1,3,5]triazine-5,7-diamine, 2-Furan-2-yl-$N^5$-{2-[4-(2,4,6-trifluoro-phenyl)-piperazin-1-yl]-ethyl}-[1,2,4]triazolo[1,5-a][1,3,5]triazine-5,7-diamine, $N^5$-{2-[4-(2,4-Difluoro-phenyl)-piperazin-1-yl]-ethyl}-2-furan-2-yl-$N^5$-methyl-[1,2,4]triazolo[1,5-a][1,3,5]triazine-5,7-diamine, and 2-Furan-2-yl-$N^5$-methyl-$N^5$-{2-[4-(2,4,6-trifluoro-phenyl)-piperazin-1-yl]-ethyl}-[1,2,4]triazolo[1,5-a][1,3,5]triazine-5,7-diamine.

27. A compound selected from the group consisting of:

5-[4-(5-chloro-1-methyl-3-trifluoromethyl-1H-pyrazol-4-ylmethyl)-piperazin-1-yl]-2-furan-2-yl-[1,2,4]triazolo[1,5-a][1,3,5]triazin-7-ylamine and $N^5$-{2-[4-(2,4-difluoro-phenyl)-piperazin-1-yl]-ethyl}-2-furan-2-yl-$N^5$-methyl-[1,2,4]triazolo[1,5-a][1,3,5]triazine-5,7-diamine.

28. A pharmaceutical composition comprising a compound of claim 1 and a pharmaceutically acceptable carrier.

29. A pharmaceutical composition comprising a compound of claim 25 and a pharmaceutically acceptable carrier.

30. A pharmaceutical composition comprising a compound of claim 26 and a pharmaceutically acceptable carrier.

31. A pharmaceutical composition comprising a compound of claim 27 and a pharmaceutically acceptable carrier.

32. A method of treating Parkinson's disease, the method comprising administering to a subject an effective amount of a compound of claim 1.

33. A pharmaceutical composition comprising a compound of claim 9 and a pharmaceutically acceptable carrier.

34. A pharmaceutical composition comprising a compound of claim 18 and a pharmaceutically acceptable carrier.

35. A method of treating Parkinson's disease, the method comprising administering to a subject an effective amount of a compound of claim 9.

36. A method of Parkinson's disease, the method comprising administering to a subject an effective amount of a compound of claim 18.

* * * * *